United States Patent
Bernardon et al.

(10) Patent No.: US 6,927,228 B2
(45) Date of Patent: *Aug. 9, 2005

(54) BIAROMATIC COMPOUND ACTIVATORS OF PPARγ-TYPE RECEPTORS

(75) Inventors: Jean-Michael Bernardon, Nice (FR); Laurence Clary, La Colle sur Loup (FR)

(73) Assignee: Galderma Research & Development, S.N.C., Valbonne Sophia Antipolis (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/360,615

(22) Filed: Feb. 10, 2003

(65) Prior Publication Data

US 2004/0039038 A1 Feb. 26, 2004

Related U.S. Application Data

(63) Continuation of application No. PCT/FR01/02543, filed on Aug. 3, 2001.

(30) Foreign Application Priority Data

Aug. 8, 2000 (FR) ............................................ 00/10447

(51) Int. Cl.⁷ ..................... A61K 31/425; C07D 277/04
(52) U.S. Cl. ....................................... 514/369; 548/183
(58) Field of Search ........................... 548/183; 574/369

(56) References Cited

U.S. PATENT DOCUMENTS 6,716,862 B2 * 4/2004 Salaski et al. .............. 514/369

OTHER PUBLICATIONS

Ishihara et al., 2000, CAS:133:58799.*

* cited by examiner

*Primary Examiner*—Rita Desai
*Assistant Examiner*—Robert Shiao
(74) *Attorney, Agent, or Firm*—Burns, Doane, Swecker & Mathis, LLP

(57) ABSTRACT

The invention relates to novel biaromatic compounds which correspond to the general formula (I) below:

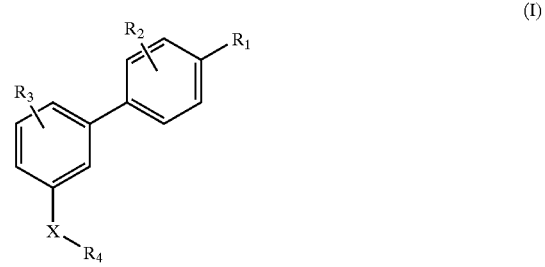

Figure 1:
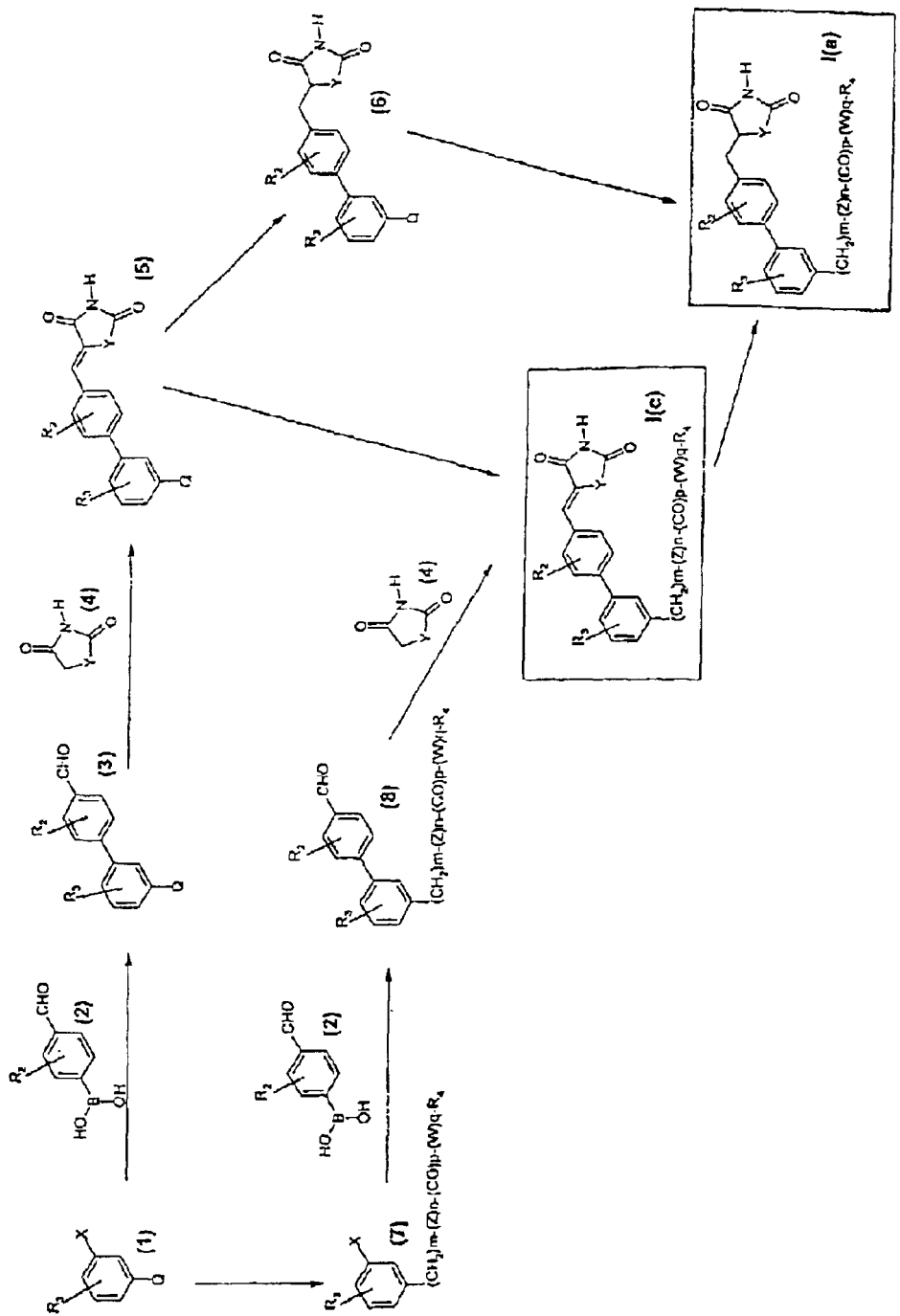

and also to the method for preparing them and their use in pharmaceutical compositions intended for use in human or veterinary medicine (in dermatology, and also in the field of cardiovascular diseases, immune diseases and/or diseases associated with lipid metabolism), or alternatively in cosmetic compositions.

14 Claims, 2 Drawing Sheets

BIAROMATIC COMPOUND ACTIVATORS OF PPARγ-TYPE RECEPTORS

CROSS-REFERENCE TO PRIORITY/PCT APPLICATIONS

This application claims priority under 35 U.S.C. § 119 of FR-00/10447, filed Aug. 8, 2000, and is a continuation of PCT/FR01/02543, filed Aug. 3, 2001 and designating the United States (published in the French language on Feb. 14, 2002 as WO 02/12210 A1; the title and abstract were also published in English), both hereby expressly incorporated by reference.

BACKGROUND OF THE INVENTION

1. Technical Field of the Invention

The invention relates to, as novel and useful industrial products, a novel class of biaromatic compounds which are activators of receptors of Peroxisome Proliferator-Activated Receptor type of sub-type γ (PPAR-γ). The invention also relates to a process for preparing them and to their use in pharmaceutical compositions intended for use in human or veterinary medicine, or alternatively in cosmetic compositions.

2. Description of the Prior Art

The activity of receptors of PPAR type has been the subject of many studies. Mention may be made, as a guide, of the publication entitled "Differential Expression of Peroxisome Proliferator-Activated Receptor Subtypes during the Differentiation of Human Keratinocytes", Michel Rivier et al., J. Invest. Dermatol 111, 1998, pp. 1116–1121, in which is listed a large number of bibliographic references relating to receptors of PPAR type. Mention may also be made, as a guide, of the report entitled "The PPARs: From orphan receptors to Drug Discovery", Timothy M. Willson, Peter J. Brown, Daniel D. Sternbach and Brad R. Henke, J. Med. Chem., 2000, Vol. 43, pp. 527–550.

PPAR receptors activate transcription by binding to elements of DNA sequences, known as peroxisome proliferator response elements (PPRE), in the form of a heterodimer with retinoid X receptors (known as RXRs).

Three sub-types of human PPAR have been identified and described: PPARα, PPARγ and PPAR δ (or NUC1).

PPARα is mainly expressed in the liver, while PPARδ is ubiquitous.

PPARγ is the most extensively studied of the three sub-types. All the references suggest a critical role of PPARs γ in regulating the differentiation of adipocytes, where it is greatly expressed. It also has a key role in systemic lipid homeostasis.

It has been described in particular in patent application WO 96/33724 that PPARγ-selective compounds, such as a prostaglandin-J2 or -D2, are potential active agents for treating obesity and diabetes.

Moreover, the Applicant has already described in patent application FR₉8/02894 the use of PPARγ activator compounds in the preparation of a pharmaceutical composition, the composition being intended to treat skin disorders associated with an anomaly of epidermal cell differentiation.

SUMMARY OF THE INVENTION

One of the aims of the present invention is to propose a novel class of PPARγ activator compounds.

Thus, the present invention relates to compounds corresponding to the following general formula:

in which
$R_1$ represents a radical of formula (a) or (b) below:

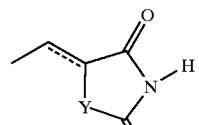

(a)

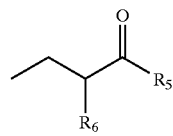

(b)

Y, $R_5$ and $R_6$ having the meanings given below, $R_2$ and $R_3$, which may be identical or different, represent a hydrogen atom, an alkyl radical containing from 1 to 12 carbon atoms, an aryl radical, a halogenatom, a radical —$OR_7$, a polyether radical, a nitro radical or an amino radical which may optionally be substituted with one (or more) alkyl radical(s) containing from 1 to 12 carbon atoms, $R_7$ having the meaning given below, X represents a structural linkage below:

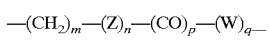

the said structural linkage being able to be read from left to right or vice versa, Z, W, m, n, p and q having the meanings given below, $R_4$ represents an alkyl radical containing from 1 to 12 carbon atoms, an aryl radical, an aralkyl radical, a heteroaryl radical or a 9-fluorenylmethyl radical, Y represents a $CH_2$ radical or a sulfur atom, $R_5$ represents a hydroxyl radical, an alkoxy radical containing from 1 to 6 carbon atoms, an NH—OH radical or a radical $N(R_8)(R_9)$, $R_8$ and $R_9$ having the meanings given below, $R_6$ represents an alkyl radical containing from 1 to 12 carbon atoms, a radical $OR_{10}$, a radical $SR_{10}$ or a radical $(CH_2)_r$—$COR_{11}$, r, $R_{10}$ and $R_{11}$ having the meanings given below, $R_7$ represents a hydrogen atom, an alkyl radical containing from 1 to 12 carbon atoms or an aralkyl radical, Z represents an oxygen or sulfur atom or a radical N—$R_{12}$, $R_{12}$ having the meaning given below, W represents an oxygen or sulfur atom, a radical $NR_{13}$ or a $CH_2$ radical, $R_{13}$ having the meaning given below, m, n, p and q, which may be identical or different, may take the values 0 or 1, it being understood that the sum m+n+p+q is greater than or equal to 2 and that when p takes the value 0 then n or q is equal to 0, $R_8$ represents a hydrogen atom or an alkyl radical containing from 1 to 12 carbon atoms, $R_9$ represents a hydrogen atom, an alkyl radical containing from 1 to 12 carbon atoms or an aryl radical, r represents 0 or 1, $R_{10}$ represents an alkyl radical containing from 1 to 12 carbon atoms, an aryl radical or an aralkyl radical, $R_{11}$ represents a hydroxyl radical, a radical $OR_{14}$ or a radical $N(R_{15})(R_{16})$, $R_{12}$ represents a hydrogen atom or an alkyl radical containing from 1 to 12 carbon atoms, $R_{13}$ represents a hydrogen atom or an alkyl radical containing from 1 to 12 carbon atoms, $R_{14}$ represents an alkyl radical containing from 1 to 12 carbon atoms, an aryl radical or an aralkyl radical, $R_{15}$ represents a hydrogen atom or an alkyl radical containing from 1 to 12 carbon atoms, $R_{16}$ represents a hydrogen atom, an alkyl radical containing from 1 to 12 carbon atoms, an aryl radical, an aralkyl radical or a heteroalkyl radical, and also the salts of the compounds of formula (I) when $R_1$ contains a carboxylic acid function, and also the optical and geometrical isomers of the said compounds of formula (I).

When the compounds according to the invention are in the form of a salt, it is preferably an alkali metal or alkaline-earth metal salt, or alternatively a zinc salt or an organoamine salt.

According to the present invention, the expression "alkyl radical containing from 1 to 12 carbon atoms" means a radical containing 1 to 12 carbon atoms and preferably methyl, ethyl, isopropyl, butyl, tert-butyl, hexyl, octyl, decyl or dodecyl radicals.

The term "polyether radical" means a polyether radical containing from 1 to 6 carbon atoms interrupted with at least one oxygen atom, such as methoxymethoxy, ethoxymethoxy or methoxyethoxymethoxy radicals.

The term "halogen atom" means a fluorine, chlorine or bromine atom.

The expression "alkoxy radical containing from 1 to 6 carbon atoms" means a radical containing from one to six carbon atoms, such as methoxy, ethoxy, isopropyloxy, tert-butoxy or hexyloxy radicals.

The term "aryl radical" means a phenyl radical which may be monosubstituted or disubstituted with a halogen atom, a $CF_3$ radical, an alkyl radical containing from 1 to 12 carbon atoms, an alkoxy radical containing from 1 to 6 carbon atoms, a nitro function, a polyether radical, a hydroxyl radical optionally protected with an acetyl or benzoyl group or an amino function optionally protected with an acetyl or benzoyl group or optionally substituted with at least one alkyl containing from 1 to 12 carbon atoms.

The term "aralkyl radical" means a benzyl or phenethyl radical which may be monosubstituted or disubstituted with a halogen atom, a $CF_3$ radical, an alkyl radical containing from 1 to 12 carbon atoms, a hydroxyl radical, an alkoxy radical containing from 1 to 6 carbon atoms, a nitro function, a polyether radical, a hydroxyl radical optionally protected with an acetyl or benzoyl group or an amino function optionally protected with an acetyl or optionally substituted with at least one alkyl containing from 1 to 12 carbon atoms.

The term "heteroaryl radical" means a pyridyl, furyl, thienyl or isoxazolyl radical optionally substituted with at least one halogen, analkyl containing from 1 to 12 carbon atoms, an alkoxy containing from 1 to 6 carbon atoms, a nitro function, a polyether radical, a hydroxyl optionally protected with an acetyl or benzoyl group or an amino function optionally protected with an acetyl or benzoyl group or optionally substituted with at least one alkyl containing from 1 to 12 carbon atoms.

DETAILED DESCRIPTION OF BEST MODE AND SPECIFIC/PREFERRED EMBODIMENTS OF THE INVENTION

Among the compounds of formula (I) above falling within the context of the present invention, mention may be made in particular of the following (alone or as a mixture):

N-[4'-(2,4-Dioxothiazolidin-5-ylmethyl)biphenyl-3-ylmethyl[-N-methylbenzamide;

5-{3'-[(Methylpyrid-2-ylamino)methyl]biphenyl-4-yl-methyl}thiazolidine-2,4-dione;

N-[4'-(2,4-Dioxothiazolidin-5-ylmethyl)biphenyl-3-ylmethyl]benzamide;

Ethyl 3-{3'-[(Benzoylmethylamino)methyl]biphenyl-4-yl}-2-methylpropionate;

2-Methyl-3-(3'-{[methyl-(1-phenylmethanoyl)amino]-methyl}biphenyl-4-yl)propionic acid;

N-[4'-(2-Carbamoylpropyl)biphenyl-3-ylmethyl]-N-methylbenzamide;

N-Methyl-N-[4'-(2-phenylcarbamoylpropyl)biphenyl-3-ylmethyl]benzamide;

N-[4'-(2-Hydroxycarbamoylpropyl)biphenyl-3-ylmethyl]-N-methylbenzamide;

1-[4'-(2,4-Dioxothiazolidin-5-ylmethyl)biphenyl-3-ylmethyl]-3-phenylurea;

1-[4'-(2,4-Dioxothiazolidin-5-ylmethyl)biphenyl-3-ylmethyl]-1-methyl-3-phenylurea; tert-Butyl [4'-(2,4-Dioxothiazolidin-5-ylmethyl)-biphenyl-3-ylmethyl]methylcarbamate;

N-[4'-(2,4-Dioxothiazolidin-5-ylmethyl)biphenyl-3-ylmethyl]-N-methylnonanamide;

(S)-2-Ethoxy-3-(3'-{[methyl-(1-phenylmethanoyl)amino]-methyl}biphenyl-4-yl)propionic acid;

Monomethyl 2-(3'-{[methyl-(1-phenylmethanoyl)amino]-methyl}biphenyl-4-ylmethyl)malonate;

Dimethyl 2-(3'-{[methyl-(1-phenylmethanoyl)amino]-methyl}biphenyl-4-ylmethyl)malonate;

Methyl 2-(3'-{[methyl-(1-phenylmethanoyl)amino]-methyl}biphenyl-4-ylmethyl)malonamate;

N-[4'-(2,4-Dioxothiazolidin-5-ylmethyl)biphenyl-3-ylmethyl]-N-ethylbenzamide;

N-[4'-(2,4-Dioxothiazolidin-5-ylmethyl)biphenyl-3-ylmethyl]-N-pentylbenzamide;

tert-Butyl [4'-(2,4-dioxothiazolidin-5-ylmethyl)-biphenyl-3-ylmethyl]ethylcarbamate;

tert-Butyl [4'-(2,4-dioxothiazolidin-5-ylmethyl)-biphenyl-3-ylmethyl]propylcarbamate;

9H-Fluoren-9-ylmethyl [4'-(2,4-dioxothiazolidin-5-ylmethyl)biphenyl-3-ylmethyl]methylcarbamate;

N-[4'-(2,4-Dioxothiazolidin-5-ylmethyl)biphenyl-3-ylmethyl]-2,2,N-trimethylpropionamide;

N-Octyl-4'-(2,4-dioxothiazolidin-5-ylmethyl)biphenyl-3-carboxamide;

N-[4'-(2,4-Dioxothiazolidin-5-ylmethyl)biphenyl-3-ylmethyl-N-methyl]-3-phenylpropionamide;

2-[4'-(2,4-Dioxothiazolidin-5-ylmethyl)biphenyl-3-yl]-N-methyl-N-phenylacetamide;

N-[4'-(2,4-Dioxothiazolidin-5-ylidenemethyl)biphenyl-3-ylmethyl]-N-propylbenzamide;

tert-Butyl [4'-(2,4-Dioxothiazolidin-5-ylmethyl)-biphenyl-3-yl]carbamate;

N-[4'-(2,4-Dioxothiazolidin-5-ylmethyl)biphenyl-3-ylmethyl]-3,4-diethoxy-N-methylbenzamide;

2-(3'-{[Methyl-(1-phenylmethanoyl)amino]methyl}-biphenyl-4-ylmethyl)malonamic acid;

N-Benzyl-N-methyl-4'-(2,4-dioxothiazolidin-5-ylmethyl)-biphenyl-3-carboxamide;

N-Benzyl-4'-(2,4-dioxothiazolidin-5-ylmethyl)biphenyl-3-carboxamide;

N-[4'-(2,4-Dioxothiazolidin-5-ylmethyl)biphenyl-3-ylmethyl]-N-methyldecanamide;

N-[4'-(2,4-Dioxothiazolidin-5-ylmethyl)biphenyl-3-yl]-2-phenylacetamide;

N-[4'-(2,4-Dioxothiazolidin-5-ylmethyl)biphenyl-3-ylmethyl]-N-methyloctanamide;

N-[4'-(2,4-Dioxothiazolidin-5-ylmethyl)biphenyl-3-ylmethyl]-N-methylheptanamide;

N-Hydroxy-2-(3'-{[methyl-(1-phenylmethanoyl)amino]-methyl}biphenyl-4-ylmethyl)malonamic acid;

N-[4'-(2,4-Dioxothiazolidin-5-ylmethyl)biphenyl-3-ylmethyl]-N-methyl-2-phenylacetamide;
N-[4'-(2,4-Dioxothiazolidin-5-ylmethyl)biphenyl-3-ylmethyl]-4-methoxy-N-methylbenzamide;
N-[4'-(2,4-Dioxothiazolidin-5-ylmethyl)biphenyl-3-ylmethyl]-3-methoxy-N-methylbenzamide;
N-[4'-(2,4-Dioxothiazolidin-5-ylmethyl)biphenyl-3-ylmethyl]-3,N-dimethylbenzamide;
N-[4'-(2,4-Dioxothiazolidin-5-ylmethyl)biphenyl-3-ylmethyl]-N-methyl-4-propylbenzamide;
N-[4'-(2,4-Dioxothiazolidin-5-ylmethyl)biphenyl-3-ylmethyl]-4,N-dimethylbenzamide;
N-[4'-(2,4-Dioxothiazolidin-5-ylmethyl)biphenyl-3-ylmethyl]-N-methylisoxazole-5-carboxamide;
N-[4'-(2,4-Dioxothiazolidin-5-ylmethyl)biphenyl-3-ylmethyl]-4-ethoxy N-methylbenzamide;
N-[4'-(2,4-Dioxothiazolidin-5-ylmethyl)biphenyl-3-ylmethyl]-4-fluoro-N-methylbenzamide;
4-Dimethylamino-N-[4'-(2,4-dioxothiazolidin-5-ylmethyl)biphenyl-3-ylmethyl]-N-methylbenzamide;
N-[4'-(2,4-Dioxothiazolidin-5-ylmethyl)biphenyl-3-ylmethyl]-N-methylnicotinamide;
3,5-Dichloro-N-[4'-(2,4-dioxothiazolidin-5-ylmethyl)-biphenyl-3-ylmethyl]-N-methylbenzamide;
N-[4'-(2,4-Dioxothiazolidin-5-ylmethyl)biphenyl-3-ylmethyl]-N-methylthiophene-2-carboxamide;
N-[4'-(2,4-Dioxothiazolidin-5-ylmethyl)biphenyl-3-ylmethyl]-N-methylhexanamide;
N-[4'-(2,4-Dioxothiazolidin-5-ylmethyl)biphenyl-3-ylmethyl]-2-methoxy-N-methylbenzamide;
N-[4'-(2,4-Dioxothiazolidin-5-ylmethyl)biphenyl-3-ylmethyl]-N-methylpyridine-2-carboxamide;
N-[4'-(2,4-Dioxothiazolidin-5-ylmethyl)biphenyl-3-ylmethyl]-N-methylfuran-2-carboxamide;
4-Butoxy-N-[4'-(2,4-dioxothiazolidin-5-ylmethyl)biphenyl-3-ylmethyl]-N-methylbenzamide;
N-[4'-(2,4-Dioxothiazolidin-5-ylmethyl)biphenyl-3-ylmethyl]-N-methylthiophene-3-carboxamide;
4-{[4'-(2,4-Dioxothiazolidin-5-ylmethyl)biphenyl-3-ylmethyl]methylcarbamoyl}phenyl acetate;
N-[4'-(2,4-Dioxothiazolidin-5-ylmethyl)biphenyl-3-ylmethyl]-4-hydroxy-N-methylbenzamide;
N-[4'-(2,4-Dioxothiazolidin-5-ylmethyl)biphenyl-3-ylmethyl]-2N-dimethylbenzamide;
2-Butyl-N-[4'-(2,4-dioxothiazolidin-5-ylmethyl)-biphenyl-3-ylmethyl]-N-methyloctanamide;
4-Acetylamino-N-[4'-(2,4-dioxothiazolidin-5-ylmethyl)-biphenyl-3-ylmethyl]-N-methylbenzamide;
Hexyl N-[4'-(2,4-dioxothiazolidin-5-ylmethyl)biphenyl-3-ylmethyl]-N-methylcarbamate;
1-[4'-(2,4-Dioxothiazolidin-5-ylmethyl)biphenyl-3-yl]-3-phenylurea;
N-[4'-(2,4-Dioxothiazolidin-5-ylmethyl)biphenyl-3-yl]-N-methyl-2-phenylacetamide;
1-[4'-(2,4-Dioxothiazolidin-5-ylmethyl)biphenyl-3-yl]-1-methyl-3-phenylurea;
1-[4'-(2,4-Dioxothiazolidin-5-ylmethyl)biphenyl-3-yl]-3-heptyl-1-methylurea;
4-Monomethyl ester of 2-{3'-[(heptanoylmethylamino)-methyl]biphenyl-4-ylmethyl)succinic acid;
2-{3'-[(Methyloctanoylamino)methyl]biphenyl-4-yl-methyl}succinic acid;
N-[4'-(2,5-Dioxopyrrolidin-3-ylmethyl)biphenyl-3-yl-methyl]-N-methylheptanamide;
3-[4'-(2,4-Dioxothiazolidin-5-ylidenemethyl)]biphenyl N-phenylcarbamate;
3-[4'-(2,4-Dioxothiazolidin-5-ylidenemethyl)]biphenyl N-heptylcarbamate;
3-[4'-(2,4-Dioxothiazolidin-5-ylmethyl)]biphenyl phenylacetate;
3-[4'-(2,4-Dioxothiazolidin-5-ylmethyl)]biphenyl nonanoate;
3-[4'-(2,4-Dioxothiazolidin-5-ylmethyl)]biphenyl N-heptylcarbamate;
3-[4'-(2,4-Dioxothiazolidin-5-ylmethyl)]biphenyl N-phenylcarbamate;
N-[6-Benzyloxy-4'-(2,4-dioxothiazolidin-5-ylidene-methyl)biphenyl-3-ylmethyl]-N-methyloctanamide;
N-[4'-(2,4-Dioxothiazolidin-5-ylmethyl)-6-hydroxybiphenyl-3-ylmethyl]-N-methyloctanamide;
N-6-Benzyloxy-4'-(2,4-dioxothiazolidin-5-ylidene-methyl)biphenyl-3-ylmethyl]-N-methyloctanamide;
N-[4''-(2,4-Dioxothiazolidin-5-ylmethyl)-[1,1';3',1''] terphenyl-5'-ylmethyl]-N-methyloctanamide;
N-[4'-(2,4-Dioxothiazolidin-5-ylmethyl)-2'-methylbiphenyl-3-ylmethyl]-N-methyloctanamide;
N-[4'-(2,4-Dioxothiazolidin-5-ylmethyl)-3'-methylbiphenyl-3-ylmethyl]-N-methyloctanamide;
(S)-2-Ethoxy-3-{3'-[(methyloctanoylamino)methyl]-biphenyl-4-yl}propionic acid;
1-[4'-(2,4-Dioxothiazolidin-5-ylmethyl)biphenyl-3-yl]-1-ethyl-3-phenylurea;
N-[4'-(2,4-Dioxothiazolidin-5-ylmethyl)biphenyl-3-yl]-N-methyldecanamide;
N-[4'-(2,4-Dioxothiazolidin-5-ylmethyl)biphenyl-3-yl]-N-methylnonanamide;
N-[4'-(2,4-Dioxothiazolidin-5-ylmethyl)biphenyl-3-yl]-N-methyl-2-(4-butoxyphenyl)acetamide;
N-[4'-(2,4-Dioxothiazolidin-5-ylmethyl)biphenyl-3-yl]-N-methyl-2-(4-methoxyphenyl)acetamide;
N-[4'-(2,4-Dioxothiazolidin-5-ylmethyl)biphenyl-3-yl]-N-methyl-2-(4-ethoxyphenyl)acetamide;
N-[4'-(2,4-Dioxothiazolidin-5-ylmethyl)biphenyl-3-yl]-N-methyl-2-(4-hydroxy phenyl)acetamide;
1-[4'-(2,4-Dioxothiazolidin-5-ylmethyl)biphenyl-3-yl]-1-methyl-3-(4-butoxyphenyl)urea;
1-[4'-(2,4-Dioxothiazolidin-5-ylmethyl)biphenyl-3-yl]-1-methyl-3-(4-methoxyphenyl)urea;
1-[4'-(2,4-Dioxothiazolidin-5-ylmethyl)biphenyl-3-yl]-1-methyl-3-(4-ethoxyphenyl)urea;
1-[4'-(2,4-Dioxothiazolidin-5-ylmethyl)biphenyl-3-yl]-1-methyl-3-(4-hydroxy phenyl)urea;
(S)-2-Ethoxy-3-(3'-{[methyl-(1-(4-butoxy)phenyl-methanoyl) amino]methyl}biphenyl-4-yl)propionic acid;
(S)-2-Ethoxy-3-(3'-{[methyl-(1-(4-methoxy)phenyl-methanoyl)amino]methyl}biphenyl-4-yl)propionic acid;
(S)-2-Ethoxy-3-(3'-{[methyl-(1-(4-ethoxyphenyl)-methanoyl) amino]methyl}biphenyl-4-yl)propionic acid;
(S)-2-Ethoxy-3-(3'-{[methyl-(1-(4-hydroxy phenyl)-methanoyl) amino]methyl}biphenyl-4-yl)propionic acid;
(S)-2-Phenoxy-3-(3'-{[methyl-(1-(4-butoxyphenyl)-methanoyl) amino]methyl}biphenyl-4-yl)propionic acid;
(S)-2-Phenoxy-3-(3'-{[methyl-(1-(4-methoxyphenyl)-methanoyl) amino]methyl}biphenyl-4-yl)propionic acid;
(S)-2-Phenoxy-3-(3'-{[methyl-(1-(4-ethoxyphenyl)-methanoyl)amino]methyl}biphenyl-4-yl)propionic acid;
(S)-2-Phenoxy-3-(3'-{[methyl-(1-(4-hydroxy phenyl)-methanoyl) amino]methyl}biphenyl-4-yl)propionic acid;
(S)-2-Phenoxy-3-(3'-{[methyl-(1-phenylmethanoyl)amino]-methyl}biphenyl-4-yl)propionic acid;
(S)-2-Phenoxy-3-{3'-[(methyloctanoylamino)methyl]-biphenyl-4-yl}propionic acid;
5-{3'-[Methyl-(2-oxo-2-phenyl ethyl)amino]biphenyl-4-ylmethyl}thiazolidine-2,4-dione;
5-[3'-(Methylphenethylamino)biphenyl-4-ylmethyl]-thiazolidine-2,4-dione;

Phenyl [4'-(2,4-dioxothiazolidin-5-ylmethyl)biphenyl-3-yl] methylcarbamate; and tert-Butyl [4'-(2,4-dioxothiazolidin-5-ylmethyl)-biphenyl-3-yl]methylcarbamate.

According to the present invention, the compounds of formula (I) that are more particularly preferred are those which have at least one of the following characteristics:

$R_1$ represents the radical of formula (a) or the radical of formula (b) in which $R_5$ represents a hydroxyl radical and $R_6$ represents a radical $OR_{10}$, X represents a structural linkage chosen from —$CH_2$—N($R_{12}$)—CO—, —$NR_{12}$—(CO)—$NR_{13}$ or $NR_{12}$—(CO)—$CH_2$—, these linkages being read from left to right or vice versa.

Figure 2:
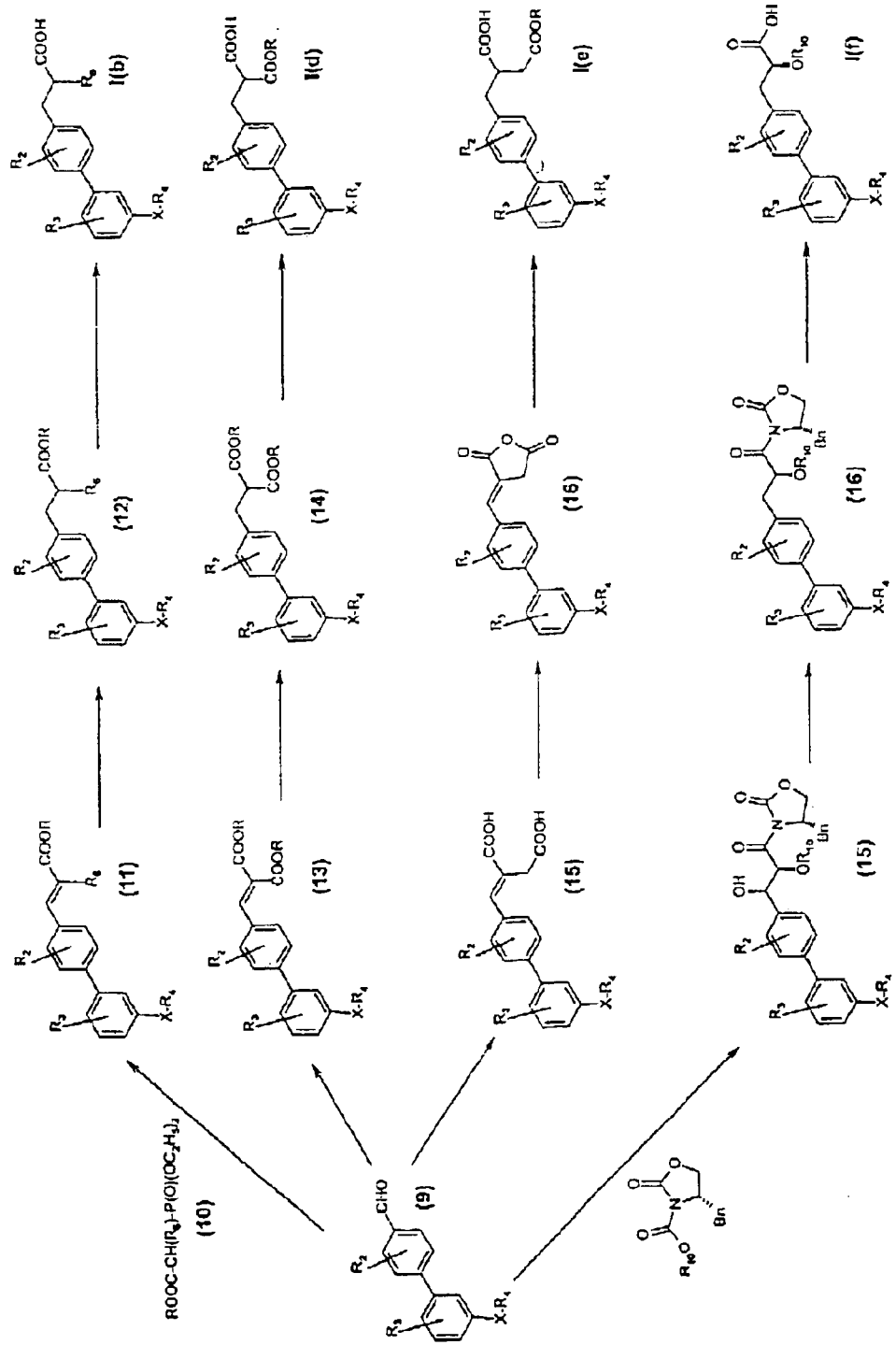

A subject of the present invention is also processes for preparing the compounds of formula (I), in particular according to the reaction schemes given in FIGS. 1 and 2.

The derivatives of formula (Ia) may be obtained (FIG. 1) from the derivatives (Ic) by hydrogenation in the presence of palladium-on-charcoal in a solvent such as dioxane, ethyl acetate, DMF or ethanol.

The derivatives of formula (Ia) may also be obtained (FIG. 1) from the thiazolidine-2,4-dione derivatives (6):

when Q represents —$(CH_2)_m$—ZH by reaction with an acyl halide of formula Cl—CO—(W)$_q$—$R_4$ in the presence of abase such as triethylamine in a solvent such as THF or dichloromethane or by reaction with an isocyanate of formula O=C=N—$R_4$;

when Q represents —$(CH_2)_m$—COOH, by reacting, in anhydrous medium in an organic solvent, preferably THF or dichloromethane and the presence of a tertiary amine (for example triethylamine or pyridine), an activated form of the acid function, for example an acid chloride, with an amine, hydroxyl or thiol derivative of formula HW—$R_4$.

The derivatives of formula (6) may be obtained (FIG. 1) from the derivatives of formula (5) by hydrogenation in the presence of palladium-on-charcoal in a solvent such as dioxane, ethyl acetate, DMF or ethanol.

The compounds (5) and (Ic) may be obtained, respectively, (FIG. 1) from the compounds (3) and (8) by reaction with 2,4-thiazolidine dione in the presence of piperidine acetate in an alcoholic solvent such as ethanol or in toluene. The compounds (3) and (8) may be obtained, respectively, (FIG. 1) from halo derivatives (1) and (7), preferably iodo or bromo derivatives, by a Suzuki-type coupling reaction with a boronic acid (2). This reaction is carried out in the presence of a palladium catalyst, for example tetrakis(triphenylphosphine)palladium under the conditions described by N. Miyaura et al., Synthetic Communications (1981) 11(7), 513–519.

The boronic derivatives (2) which may be obtained from the corresponding halo derivatives (preferably iodo or bromo) by first protecting the aldehyde function in the form of acetal and then converting into the lithium reagent, reacting with trimethyl borate and hydrolysis.

The derivatives of formula (Ib) may be obtained (FIG. 2) from aldehyde derivatives (9), according to Horne-type reaction with a lithium or sodium derivative of a phosphonate (10), followed by hydrogenation in the presence of palladium-on-charcoal and saponification of the ester to acid.

The derivatives of formula (Id) may be obtained (FIG. 2) by a sequence of reactions under the conditions described by S. Doulut et al., J. Med. Chem. (1993) 36, 1369–1379.

The derivatives of formula (Ie) may be obtained (FIG. 2) by a sequence of reactions under the conditions described by H. Shinkai et al., J. Med. Chem. (1998) 41, 1927–1933.

The derivatives of formula (If) may be obtained (FIG. 2) by a sequence of reactions under the conditions described by B. Hulin et al., J. Med. Chem. (1996) 39, 3987–3907.

When $R_1$ comprises an acid function, the compounds are prepared by protecting $R_1$ with a protecting group of alkyl type containing from 1 to 12 carbon atoms or of allylic, benzylic or tert-butyl type.

Conversion to the free form may be carried out:

in the case of an alkyl protecting group containing from 1 to 12 carbon atoms, using sodium hydroxide or lithium hydroxide in an alcoholic solvent such as methanol or in THF;

in the case of an allylic protecting group, using a catalyst such as certain transition metal complexes in the presence of a secondary amine such as morpholine;

in the case of a benzylic protecting group, by debenzylation in the presence of hydrogen using a catalyst such as palladium-on-charcoal;

in the case of a protecting group of tert-butyl type, using trimethylsilyl iodide.

The compounds according to the invention have activation properties on PPARγ-type receptors.

According to the invention, the expression "activator of PPARγ-type receptors" means any compound which shows, at a concentration of 1 $\mu$M in a transactivation test, as described in Kliewer et al., Nature 358, 771–774, 1992, a percentage of activation of PPARγ receptors of at least 20%, calculated relative to a reference compound, SB 219994, which gives 100% activation of PPARγs.

Preferably, the activator of PPARγ-type receptors shows a percentage of activation of greater than or equal to 40% and advantageously greater than or equal to 70%.

Preferably, the activator of PPARγ-type receptors is specific, i.e., it has a ratio of the percentage of activation of PPARγ receptors to the percentage of activation of PPARα receptors (calculated relative to a reference compound, Wy 14643, which gives 100% activation of PPARαs) of greater than or equal to 3. Preferably, this ratio is greater than or equal to and more advantageously greater than or equal to 10.

The affinity of the PPAR derivatives for the human PPARγ receptor has also been determined in a binding test, by competition of the binding of a reference agonist, tritiated BRL 49,653. The technique of adsorption on hydroxyapatite gel was used to separate the receptor-bound ligand from the free ligand. The human PPARγ receptor was prepared from Sf9 insect cells infected with a recombinant baculovirus. The results are expressed as a Kd value (nM) which represents the equilibrium dissociation constant obtained for each compound. The expression "PPARγ receptor ligand" means any compound according to the invention having a Kd value of less than 10 000 nM. Preferably, the compounds according to the invention have a Kd value of less than 1 000 nM and advantageously less than 100 nM.

A subject of the present invention is also, as medicinal products, the compounds of formula (I) as described above.

The compounds according to the invention are particularly suitable in the following fields of treatment, namely, regimes or regimens:

1) for treating dermatological complaints associated with a keratinization disorder relating to differentiation and to proliferation, in particular for treating common acne, comedones, polymorphs, rosacea, nodulokystic acne, acne conglobata, senile acne and secondary acne such as solar, medicinal or occupational acne, 2) for treating other types of keratinization disorder, in particular ichthyosis, ichthyosiform conditions, Darrier's disease, palmoplantar keratoderma, leukoplakia and leukoplakiform conditions, and cutaneous or mucous (oral) lichen, 3) for treating other dermatological complaints with an inflammatory immuno-allergic component, with or without a cellular proliferation disorder, and in particular all forms of psoriasis, whether cutaneous, mucous or ungual psoriasis, and even arthropathia psoriatica, or alternatively cutaneous atopy such as eczema, or respiratory atopy or gingival hypertrophy, 4) for treating all dermal or epidermal proliferations, whether benign or malignant, whether or not of viral origin, such as common warts, flat warts and epidermodysplasia verruciformis, oral or florid papillomatoses, T lymphoma and proliferations which may be induced by ultraviolet light, in particular in the case of basal cell and prickle cell epithelioma, and also any precancerous skin lesion such as keratoacanthomas, 5) for treating other dermatological disorders such as immune dermatitides, such as lupus erythematosus, bullous immune diseases and collagen diseases, such as Scleroderma, 6) in the treatment of dermatological or systemic complaints with an immunological component, 7) in the treatment of skin disorders due to exposure to UV radiation, and also for repairing or combating aging of the skin, whether light-induced or chronological aging, or for reducing actinic keratoses and pigmentations, or any pathology associated with chronological or actinic aging, such as xerosis, 8) for combating sebaceous function disorders such as hyperseborrhoea of acne or simple seborrhoea, 9) for preventing or treating cicatrization disorders of for preventing or repairing stretch marks, 10) in the treatment of pigmentation disorders, such as hyperpigmentation, melasma, hypopigmentation or vitiligo, 11) in the treatment of lipid metabolism complaints, such as obesity, hyperlipidaemia or non-insulin-dependent diabetes, 12) in the treatment of inflammatory complaints such as arthritis, 13) in the treatment or prevention of cancerous or precancerous conditions, 14) in the prevention or treatment of alopecia of various origins, in particular alopecia caused by chemotherapy or radiation, 15) in the treatment of immune system disorders, such as asthma, type I sugar diabetes, multiple sclerosis or other selective dysfunctions of the immune system, 16) in the treatment of complaints of the cardiovascular system, such as arteriosclerosis or hypertension.

A subject of the present invention is also a pharmaceutical or cosmetic composition comprising, in an physiologically acceptable medium, at least one compound of formula (I) as defined above.

A subject of the present invention is also the use of the compounds of formula (I) to manufacture a composition for treating the above-mentioned complaints, in particular for regulating and/or restoring the metabolism of skin lipids.

The composition according to the invention may be administered enterally, parenterally, topically or ocularly. The pharmaceutical composition is preferably packaged in a form which is suitable for topical application.

Via the enteral route, the composition, more particularly the pharmaceutical composition, may be in the form of tablets, gel capsules, sugar-coated tablets, syrups, suspensions, solutions, powders, granules, emulsions or lipid or polymer vesicles or nanospheres or microspheres to allow controlled release. Via the parenteral route, the composition may be in the form of solutions or suspensions for infusion or for injection.

The compounds according to the invention are generally administered at a daily dose of about 0.001 mg/kg to 100 mg/kg of body weight in 1 to 3 dosage intakes.

The compounds are used systemically at a concentration generally of between 0.001% to 10% by weight and preferably between 0.01% to 1% by weight relative to the weight of the composition.

Via the topical route, the pharmaceutical composition according to the invention is more particularly intended for treating the skin and mucous membranes and may be in the form of ointments, creams, milks, salves, powders, impregnated pads, solutions, gels, sprays, lotions or suspensions. It may also be in the form of lipid or polymer vesicles or nanospheres or microspheres or polymer patches and hydrogels to allow controlled release. This topical-route composition maybe in anhydrous form, in aqueous form or in the form of an emulsion.

The compounds are used topically at a concentration generally of between 0.001% to 10% by weight, preferably between 0.01% to 1% by weight relative to the total weight of the composition.

The compounds of formula (I) according to the invention also find an application in the cosmetic field, in particular in body and hair hygiene and more particularly for regulating and/or restoring skin lipid metabolism. Compared with the products known previously, these compounds of formula (I) have the advantage of also having other advantageous properties, in particular anti-inflammatory or soothing properties, which makes these compounds less irritant and thus better tolerated.

A subject of the invention is also the cosmetic use of a composition comprising, in a physiologically acceptable support, at least one of the compounds of formula (I) for body or hair hygiene.

The cosmetic composition according to the invention containing, in a cosmetically acceptable support, at least one compound of formula (I) or an optical or geometrical isomer thereof or a salt thereof, may usually be in the form of a cream, a milk, a lotion, a gel, lipid or polymer vesicles or nanospheres or microspheres, a soap or a shampoo.

The concentration of compound of formula (I)in the cosmetic composition is between 0.001% to 3% by weight relative to the total weight of the composition.

The compositions as described above may, of course, also contain inert or even pharmacodynamically active additives or combinations of these additives, and in particular: wetting agents; depigmenting agents such as hydroquinone, azelaic acid, caffeic acid or kojic acid; emollients; moisturizers such as glycerol, PEG-400, thiamorpholinone and its derivatives or urea; anti-seborrhoeic or anti-acne agents, such as S-carboxymethylcysteine, S-benzylcysteamine, salts thereof or derivatives thereof, or benzoyl peroxide; antifungal agents such as ketoconazole or poly(4,5-methylene-3-isothiazolidones); antibacterial agents, carotenoids and in particular β-carotene; anti-psoriatic agents such as anthralin and its derivatives; eicosa-5,8,11,14-tetraynoic acid and eicosa-5,8,11-triynoic acid, and esters and amides thereof, and finally retinoids. The compounds of formula (I) may also be combined with D vitamins or derivatives thereof, with corticosteroids, with free-radical scavengers, α-hydroxy or α-keto acids or derivatives thereof, or alternatively with ion-channel blockers.

These compositions may also contain flavor enhancers, preserving agents such as para-hydroxybenzoic acid esters, stabilizers, moisture regulators, pH regulators, osmotic pressure modifiers, emulsifiers, UV-A and UV-B screening agents, and antioxidants, such as α-tocopherol, butylhydroxyanisole or butylhydroxytoluene.

Needless to say, a person skilled in the art will take care to select the optional compound(s) to be added to these compositions such that the advantageous properties intrinsically associated with the present invention are not, or are not substantially, adversely affected by the addition envisaged.

Several examples of the production of active compounds of formula (I) according to the invention, and also results of biological activity of such compounds and various concrete formulations based on these compounds, will be given by way of illustration and with no limiting nature.

EXAMPLE 1

N-[4'-(2,4-Dioxothiazolidin-5-ylmethyl)biphenyl-3-ylmethyl]-N-methylbenzamide (a) tert-Butyl (3-bromo benzyl)carbamate 15 g (67 mmol) of 3-bromobenzylaminehydrochloride, 9.4 ml of triethylamine (67 mmol) and 150 ml of dichloromethane are introduced into a round-bottomed flask under a stream of nitrogen. 15.5 ml (67 mmol) of di-tert-butyl dicarbonate are added portionwise at room temperature and the mixture is stirred for three hours. The reaction medium is poured into ice-cold water and extracted with dichloromethane, and the organic phase is separated out after settling of the phases has taken place, dried over magnesium sulfate and evaporated. 19.3 g (100%) of the expected product are collected.

(b) tert-Butyl (3-bromo benzyl)-N-methylcarbamate 19.3 g (67 mmol) of tert-butyl (3-bromo benzyl)carbamate and 200 ml of THF are introduced into a round-bottomed flask under a stream of nitrogen. 3 g (74 mmol) of sodium hydride (60% in oil) are added portionwise and the mixture is stirred until the evolution of gas has ceased. 4.6 ml (74 mmol) of methyl iodide are then added and the mixture is stirred for one hour. The reaction medium is poured into ice-cold water and extracted with ethyl acetate, and the organic phase is separated out after settling of the phases has taken place, dried over magnesium sulfate and evaporated. 20.4 g (100%) of the expected product are collected.

(c) (3-Bromo benzyl)methylamine 20.2 g (67 mmol) of tert-butyl (3-bromo-benzyl)-N-methylcarbamate are introduced into 100 ml of dichloromethane in a round-bottomed flask under a stream of nitrogen, and 26 ml (335 mmol) of trifluoroacetic acid are added. The reaction medium is stirred at room temperature for 8 hours and hydrolyzed with saturated potassium carbonate solution. The mixture is extracted with dichloromethane and the organic phase is separated out after settling of the phases has taken place, washed with water, dried over magnesium sulfate and evaporated. The residue obtained is purified by chromatography on a column of silica eluded with a mixture of dichloromethane and methanol (50/50). After evaporation of the solvents, 9 g (67%) of the expected product are collected.

(d) N-(3-Bromo benzyl)-N-methylbenzamide 9 g (45 mmol) of (3-bromo benzyl)methylamine, 90 ml of THF and 6.9 ml (50 mmol) of triethylamine are introduced into a round-bottomed flask under a stream of nitrogen. 5.7 ml (50 mmol) of benzoyl chloride are added dropwise and the mixture is stirred for one hour. The reaction medium is poured into water and extracted with dichloromethane, and the organic phase is separated out after settling of the phases has taken place, washed with water, dried over magnesium sulfate and evaporated. The residue obtained is purified by chromatography on a column of silica eluded with a mixture of ethyl acetate and heptane (15/85). After evaporation of the solvents, 13.7 g (64%) of the expected product are collected.

(e) N-(4'-Formylbiphenyl-3-ylmethyl)-N-methylbenzamide 8.8 g (29 mmol) of N-(3-bromo benzyl)-N-methylbenzamide, 8.7 g (58 mmol) of 4-formylbenzeneboronic acid and 125 ml of toluene are introduced into a three-necked flask under argon. 36 ml (72 mmol) of aqueous potassium carbonate solution (2M) are added dropwise, the reaction medium is degassed with argon and 1 g of tetrakis(triphenylphosphine)palladium(0) chloride is added with heating at 90° C. for 24 hours. The reaction medium is poured into water and extracted with dichloromethane, and the organic phase is separated out after settling of the phases has taken place, dried over magnesium sulfate and evaporated. The residue obtained is purified by chromatography on a column of silica eluded with a mixture of heptane and ethyl acetate (50/50). After evaporation of the solvents, 7.2 g (75%) of the expected product are collected.

(f) N-[4'-(2,4-Dioxothiazolidin-5-ylidenemethyl)-biphenyl-3-ylmethyl]-N-methylbenzamide 1.6 g (4.6 mmol) of N-(4'-Formylbiphenyl-3-ylmethyl)-N-methylbenzamide, 610 mg (4.6 mmol) of 2,4-thiazolidine dione, 137 mg of piperidine acetate and 60 ml of toluene are introduced into a round-bottomed flask under a stream of nitrogen. The mixture is refluxed for five hours and the water formed is separated out using Dean-Stark apparatus. The reaction medium is cooled and the precipitate formed is filtered off and purified on a column of silica with an fluent mixture of heptane and ethyl acetate (70/30). After evaporation of the solvents, 1.4 g (70%) of the expected product are collected.

(g) N-[4'-(2,4-Dioxothiazolidin-5-ylmethyl)-biphenyl-3-ylmethyl]-N-methylbenzamide 1.4 g (3.3 mmol) of N-[4'-(2,4-dioxo-thiazolidin-5-ylidenemethyl)biphenyl-3-ylmethyl]-N-methylbenzamide, 30 ml of DMF and 25 ml of ethyl acetate are introduced into a three-necked flask. The reaction medium is degassed, 1.4 g of palladium-on-charcoal (10%) are introduced and the mixture is hydrogenated under atmospheric pressure at 60° C. The reaction medium is filtered and evaporated, and the residue obtained is purified by chromatography on a column of silica eluded with a mixture of dichloromethane and methanol (99/1). After evaporation of the solvents, 300 mg (21%) of N-[4'-(2,4-dioxo-thiazolidin-5-ylmethyl)biphenyl-3-ylmethyl]-N-methylbenzamide with a melting point of 70–71° C., are collected.

EXAMPLE 2

5-{3'-[(Methylpyrid-2-ylamino)methyl]biphenyl-4-ylmethyl}thiazolidine-2,4-dione (a) (3-Bromo benzyl)methylpyrid-2-ylamine 1.5 g (7.5 mmol) of (3-bromo benzyl)-methylamine and 15 ml of 2-fluoropyridine are introduced into a round-bottomed flask under a stream of nitrogen. The reaction medium is refluxed for 8 hours and evaporated to dryness.

The residue obtained is purified by chromatography on a column of silica eluded with a mixture of heptane and ethyl acetate (80/20). After evaporation of the solvents, 1 g (50%) of expected product is collected.

(b) 3'-[(Methylpyrid-2-ylamino)methyl]biphenyl-4-carbaldehyde

In a manner similar to that of Example 1(e), by reacting 475 mg (1.7 mmol) of (3-bromo benzyl)methyl-pyrid-2-ylamine with 386 mg (2.6 mmol) of 4-formylbenzene boronic acid, 310 mg (60%) of expected product are obtained.

(c) 5-{3'-[(Methylpyrid-2-ylamino)methyl]-biphenyl-4-ylmethylene}thiazolidine-2,4-dione In a manner similar to that of Example 1(f), by reacting 610 mg (1.85 mmol) of 3'-[(methylpyrid-2-ylamino)methyl]biphenyl-4-carbaldehyde with 216 mg (1.85 mmol) of 2,4-thiazolidine dione, 640 mg (81%) of expected product are obtained.

(d) 5-{3'-[(Methylpyrid-2-ylamino)methyl]-biphenyl-4-ylmethyl}thiazolidine-2,4-dione In a manner similar to that of Example 1(g), starting with 310 mg (0.8 mmol) of 5-{3'-[(methylpyrid-2-ylamino)methyl]biphenyl-4-ylmethylene}thiazolidine-2,4-dione, 80 mg (26%) of 5-{3'-[(methylpyrid-2-ylamino)methyl]biphenyl-4-ylmethyl}thiazolidine-2,4-dione, with a melting point of 135–136° C., are obtained.

EXAMPLE 3

N-[4'-(2,4-Dioxothiazolidin-5-ylmethyl)biphenyl-3-ylmethyl]benzamide (a) N-(3-Bromo benzyl)benzamide In a manner similar to that of Example 1(d), 15 by reacting 7 g (32 mmol) of 3-bromobenzylamine with 4 ml (35 mmol) of benzoyl chloride, 9.1 g (100%) of expected product are obtained.

(b) N-(4'-Formylbiphenyl-3-ylmethyl)benzamide

In a manner similar to that of Example 1(e), by reacting 2 g (6.9 mmol) of N-(3-bromo benzyl)-benzamide with 1.6 g (10.3 mmol) of 4-formylbenzene-boronic acid, 1.4 g (65%) of expected product are obtained.

(c) N-[4'-(2,4-Dioxothiazolidin-5-ylidenemethyl)-biphenyl-3-ylmethyl]benzamide

In a manner similar to that of Example 1(f), by reacting 1 g (3.2 mmol) of N-(4'-formylbiphenyl-3-ylmethyl)benzamide with 370 mg (3.2 mmol) of 2,4-thiazolidine dione, 1.2 g (93%) of expected product are obtained.

(d) N-[4'-(2,4-Dioxothiazolidin-5-ylmethyl)-biphenyl-3-ylmethyl]benzamide

In a manner similar to that of Example 1(g), starting with 600 g (1.45 mmol) of N-[4'-(2,4-dioxothiazolidin-5-ylidenemethyl)biphenyl-3-ylmethyl]-benzamide, 200 mg (33%) of N-[4'-(2,4-dioxothiazolidin-5-ylmethyl)biphenyl-3-ylmethyl]benzamide, with a melting point of 225–226° C., are obtained.

EXAMPLE 4

Ethyl 3-{3'-[(benzoylmethylamino)methyl]biphenyl-4-yl}-2-methylpropionate (a) Ethyl (E)-2-methyl-3-(3'-{[(1-phenyl-methanoyl)amino]methyl}biphenyl-4-yl)acrylate 440 mg (11 mmol) of sodium hydride (80% in oil) and 10 ml of THF are introduced into a three-necked flask under a stream of nitrogen. A solution of 2.2 ml of triethyl 2-phosphonopropionate in 10 ml of THF is added dropwise, followed by a solution of 3 g (9.1 mmol) of N-(4'-formylbiphenyl-3-ylmethyl)-N-methylbenzamide (prepared in Example 1(e)), and the mixture is stirred at room temperature for 3 hours. The reaction medium is poured into water and extracted with dichloromethane, and the organic phase is separated out after settling of the phases has taken place, dried over magnesium sulfate and evaporated. The residue obtained is purified by chromatography on a column of silica eluded with a mixture of heptane and ethyl acetate (70/30). After evaporation of the solvents, 3 g (80%) of ethyl (E)-2-methyl-3-(3'-{[(1-phenyl-methanoyl)amino]methyl}biphenyl-4-yl)acrylate are collected in the form of an oil.

(b) Ethyl 3-{3'-[(benzoylmethylamino)-methyl]biphenyl-4-yl}-2-methylpropionate 2.2 g (5.3 mmol) of ethyl (E)-2-methyl-3-(3'-{[(1-phenylmethanoyl)amino]methyl}biphenyl-4-yl)acrylate and 100 ml of ethyl acetate are introduced into a three-necked flask. The reaction medium is degassed, 450 mg of palladium-on-charcoal (10%) are added and the mixture is hydrogenated under atmospheric pressure for two hours. The reaction medium is filtered and evaporated, and the residue obtained is purified by chromatography on a column of silica eluded with a mixture of heptane and ethyl acetate (80/20). After evaporation of the solvents, 1.45 g (64%) of ethyl 3-{3'-[(benzoylmethylamino)methyl]biphenyl-4-yl}-2-methylpropionate are collected in the form of an oil.

EXAMPLE 5

2-Methyl-3-(3'-{[methyl-(1-phenylmethanoyl)amino]-methyl}biphenyl-4-yl)propionic acid 1.25 g (3 mmol) of ethyl 3-{3'-[(benzoyl-methylamino)methyl]biphenyl-4-yl}-2-methylpropionate, 3 ml of sodium hydroxide (10N), 32 ml of THF and 2 ml of methanol are introduced into a round-bottomed flask. The reaction medium is refluxed for 8 hours, poured into water, acidified to pH 4 with 1N hydrochloric acid and extracted with dichloromethane, and the organic phase is separated out after settling of the phases has taken place, dried over magnesium sulfate and evaporated. The residue obtained is purified by chromatography on a column of silica eluded with a mixture of heptane and ethyl acetate (60/40). 900 mg (90%) of 2-methyl-3-(3'-{[methyl-(1-phenylmethanoyl)-amino]methyl}biphenyl-4-yl)propionic acid, with a melting point of 60–61° C., are obtained.

EXAMPLE 6

N-[4'-(2-Carbamoylpropyl)biphenyl-3-ylmethyl]-N-methylbenzamide (a) 3-(3'-{[Methyl-(1-phenylmethanoyl)amino]-methyl}biphenyl-4-yl)propionyl chloride By reacting 1.6 g (4.1 mmol) of 2-methyl-3-(3'-{[methyl-(1-phenylmethanoyl)amino]methyl}biphenyl-4-yl)propionic acid with 390 µl (4.5 mmol) of oxalyl chloride in dichloromethane, and after evaporation, 1.7 g (100%) of 3-(3'-{[methyl-(1-phenylmethanoyl)-amino]methyl}biphenyl-4-yl)propionyl chloride are obtained.

(b) N-[4'-(2-Carbamoylpropyl)biphenyl-3-ylmethyl]-N-methylbenzamide

By reacting a solution of 1.7 g (4.1 mmol) of 3-(3'-{[methyl-(1-phenylmethanoyl)amino]-methyl}biphenyl-4-yl)propionyl chloride in 5 ml of THF with 10 ml of aqueous ammonia, and after purification by chromatography on a column of silica, 200 mg (32%) of N-[4'-(2-carbamoylpropyl)biphenyl-3-ylmethyl]-N-methylbenzamide, with a melting point of 47–48° C., are obtained.

EXAMPLE 7

N-Methyl-N-[4'-(2-phenylcarbamoylpropyl) biphenyl-3-ylmethyl]benzamide

By reacting a solution of 637 mg (1.6 mmol) of 3-(3'-{[methyl-(1-phenylmethanoyl)amino]-methyl}biphenyl-4-yl)propionyl chloride in 5 ml of THF with 146 μl (1.6 mmol) of benzylamine in the presence of 250 μl (1.8 mmol) of triethylamine (1.6 mmol), and after purification by chromatography on a column of silica, 370 mg (50%) of N-methyl-N-[4'-(2-phenyl-carbamoylpropyl)biphenyl-3-ylmethyl] benzamide, with a melting point of 68–69° C., are obtained.

EXAMPLE 8

N-[4'-(2-Hydroxycarbamoylpropyl)biphenyl-3-yl-methyl]-N-methylbenzamide

By reacting a solution of 669 mg (1.65 mmol) of 3-(3'-{[methyl-(1-phenylmethanoyl)amino]-methyl}biphenyl-4-yl)propionyl chloride in 6 ml of THF with 243 mg (1.65 mmol) of O-(tert-butyldimethyl-silyl) hydroxylamine in the presence of 250 μl (1.8 mmol) of triethylamine, followed by deprotection with 530 μl of tetrabutylammonium fluoride solution (1N in THF), and after purification by chromatography on a column of silica, 350 mg (42%) of N-[4'-(2-hydroxy-carbamoylpropyl)biphenyl-3-ylmethyl]-N-methylbenzamide, with a melting point of 65–66° C., are obtained.

EXAMPLE 9

1-[4'-(2,4-Dioxothiazolidin-5-ylmethyl)biphenyl-3-ylmethyl]-3-phenylurea (a) 1-(4'-Bromobiphenyl-3-ylmethyl)-3-phenylurea 2.9 g (14.5 mmol) of 3-bromobenzylamine and 90 ml of dichloromethane are introduced into a round-bottomed flask and 1.73 ml (16 mmol) of phenyl isocyanate are added dropwise. The reaction medium is stirred at room temperature for eight hours, poured into water and extracted with dichloromethane, and the organic phase is separated out after settling of the phases has taken place, dried over magnesium sulfate and evaporated. The residue obtained is purified by chromatography on a column of silica eluded with a mixture of heptane and ethyl acetate (70/30). 3.7 g (80%) of the expected product are obtained.

(b) 1-(4'-Formylbiphenyl-3-ylmethyl)-3-phenylurea.

In a manner similar to that of Example 1(e), by reacting 2.5 g (8.2 mmol) of 1-(4'-bromobiphenyl-3-ylmethyl)-3-phenylurea with 1.8 g (12.3 mmol) of 4-formylbenzene boronic acid, 2.1 g (77%) of the expected product are obtained.

(c) 1-[4'-(2,4-Dioxothiazolidin-5-ylidene-methyl) biphenyl-3-ylmethyl]-3-phenylurea In a manner similar to that of Example 1(f), by reacting 2.1 g (6.4 mmol) of 1-(4'-formylbiphenyl-3-ylmethyl)-3-phenylurea with 750 mg (6.4 mmol) of 2,4-thiazolidine dione, 1.4 g (53%) of the expected product are obtained.

(d) 1-[4'-(2,4-Dioxothiazolidin-5-yl-methyl)biphenyl-3-ylmethyl]-3-phenylurea

In a manner similar to that of Example 1(g), starting with 1.4 g (3.3 mmol) of 1-(4'-(2,4-dioxothiazolidin-5-ylidenemethyl)biphenyl-3-ylmethyl]-3-phenylurea, 300 mg (21%) of 1-(4'-(2,4-dioxothiazolidin-5-ylmethyl)biphenyl-3-ylmethyl]-3-phenylurea, with a melting point of 70–71° C., are obtained.

EXAMPLE 10

1-[4'-(2,4-Dioxothiazolidin-5-ylmethyl)biphenyl-3-ylmethyl]-1-methyl-3-phenylurea (a) tert-Butyl (4'-formylbiphenyl-3-ylmethyl)-methylcarbamate In a manner similar to that of Example 1(e) by reacting 13.7 g (45 mmol) of tert-butyl (3-bromo benzyl)-N-methylcarbamate (prepared in Example 1(b)) with 10 g (67 mmol) of 4-formylbenzene-boronic acid, 11 g (76%) of the expected are obtained.

(b) tert-Butyl [4'-(2,4-dioxothiazolidin-5-ylidenemethyl) biphenyl-3-ylmethyl]methylcarbamate In a manner similar to that of Example 1(f), by reacting 8 g (25 mmol) of tert-butyl (4'-formyl-biphenyl-3-ylmethyl) methylcarbamate with 2.9 g (25 mmol) of 2,4-thiazolidine dione, 8.6 g (81%) of the expected product are obtained.

(c) 5-(3'-Methylaminomethylbiphenyl-4-ylidene-methyl) thiazolidine-2,4-dione 2 g (4.7 mmol) of tert-butyl [4'-(2,4-dioxo-thiazolidin-5-ylidenemethyl)biphenyl-3-ylmethyl]methyl-carbamate and 20 ml of dichloromethane are introduced into a round-bottomed flask. 2.2 ml (28.2 mmol) of trifluoroacetic acid are added and the mixture is stirred at room temperature for four hours. The reaction medium is poured into aqueous bicarbonate solution and extracted with dichloromethane, and the organic phase is separated out after settling of the phases has taken place, dried over magnesium sulfate and evaporated. 1.3 g (85%) of the expected product are obtained.

(d) 1-[4'-(2,4-Dioxothiazolidin-5-ylidene-methyl) biphenyl-3-ylmethyl]-1-methyl-3-phenylurea In a manner similar to that of Example 9(a) by reacting 300 mg (0.9 mmol) of 5-(3'-methylaminomethylbiphenyl-4-ylmethylene)thiazolidine-2,4-dione with 190 μl (1.8 mmol) of phenyl isocyanate, 450 mg (98%) of the expected product are obtained.

(e) 1-[4'-(2,4-Dioxothiazolidin-5-ylmethyl)-biphenyl-3-ylmethyl]-1-methyl-3-phenylurea In a manner similar to that of Example 1(g), starting with 450 mg (0.8 mmol) of 1-[4'-(2,4-dioxo-thiazolidin-5-ylidenemethyl)biphenyl-3-ylmethyl]-1-methyl-3-phenylurea, 100 mg (28%) of 1-[4'-(2,4-dioxo-thiazolidin-5-ylmethyl)biphenyl-3-ylmethyl]-1-methyl-3-phenylurea, with a melting point of 70–71° C., are obtained.

EXAMPLE 11 tert-Butyl [4'-(2,4-dioxothiazolidin-5-ylmethyl) biphenyl-3-ylmethyl]methylcarbamate In a manner similar to that of Example 1(g), starting with 500 mg (1.2 mmol) of tert-butyl [4'-(2,4-dioxothiazolidin-5-ylidenemethyl)biphenyl-3-ylmethyl]methylcarbamate (prepared in Example 10(b)), 250 mg (49%) of tert-butyl [4'-(2,4-dioxothiazolidin-5-ylmethyl)biphenyl-3-ylmethyl] methylcarbamate, with a melting point of 45–46° C., are obtained.

EXAMPLE 12

N-[4'[2,4-dioxothiazolidin-5-ylmethyl)biphenyl-3-ylmethyl]-N-methylnonanamide (a) N-[4'[2,4-Dioxothiazolidin-5-ylidene-methyl) biphenyl-3-ylmethyl]-N-methylnonanamide In a manner similar to that of Example 1(d) by reacting 500 mg (0.9 mmol) of 5-(3'-methylaminomethylbiphenyl-4-ylmethylene)thiazolidine-2,4-dione with 330 µl (1.8 mmol) of nonanoyl chloride, 350 mg (66%) of the expected product are obtained.

(b) N-[4'-(2,4-Dioxothiazolidin-5-ylmethyl)-biphenyl-3-ylmethyl]-N-methylnonanamide In a manner similar to that of Example 1(g), starting with 330 mg (0.7 mmol) of N-[4'[2,4-dioxothiazolidin-5-ylidenemethyl)biphenyl-3-ylmethyl]-N-methylnonanamide, 70 mg (21%) of N-[4'-(2,4-dioxothiazolidin-5-ylmethyl) biphenyl-3-ylmethyl]-N-methylnonanamide are obtained.

EXAMPLE 13

(S)-2-Ethoxy-3-(3'-{[methyl-(1-phenylmethanoyl)-amino]methyl}biphenyl-4-yl)propionic acid (a) N-{4'-[(1R,2S)-3-((S)-4-Benzyl-2-oxo-oxazolidin-3-yl)-2-ethoxy-1-hydroxy-3-oxopropyl]biphenyl-3-ylmethyl}-N-methylbenzamide 1.8 g (6.7 mmol) of (S)-4-benzyl-3-(2-ethoxy-ethanoyl) oxazolidin-2-one amd 15 ml of dichloromethane are introduced into a three-necked flask under argon. 7.3 ml (8 mmol) of dibutylborane trifluoromethane-sulfonate and 1.3 ml (8 mmol) of diisopropylethylamineare successively added dropwise at 0° C., and the mixture is stirred for one hour. At −78° C., a solution of 2 g (6 mmol) of N-(4'-formylbiphenyl-3-ylmethyl)-N-methylbenzamide (prepared in Example 1(e)) in 25 ml of dichloromethane is added and the mixture is stirred for one hour. The mixture is allowed to warm to 0° C. and is treated with a pH 7 buffer solution (16 ml) in 45 ml of methanol and then with aqueous hydrogen peroxide solution (16 ml) in 45 ml of methanol and stirred for one hour at 0° C. The reaction medium is poured into water and extracted with dichloromethane, and the organic phase is separated out after settling of the phases has taken place, dried over magnesium sulfate and evaporated. The residue obtained is purified by chromatography on a column of silica eluted with a mixture of heptane and ethyl acetate (60/40). 1.7 g (48%) of N-{4'-[(1R,2S)-3-((S)-4-benzyl-2-oxo-oxazolidin-3-yl)-2-ethoxy-1-hydroxy-3-oxopropyl] biphenyl-3-ylmethyl}-N-methylbenzamide are obtained.

(b) N-{4'-[(S)-3-((S)-4-Benzyl-2-oxooxazolidin-3-yl)-2-ethoxy-3-oxopropyl]biphenyl-3-ylmethyl}-N-methylbenzamide 320 µl (2.6 mmol) of boron trifluoride etherate and 5 ml of dichloromethane are introduced into a three-necked flask under a stream of nitrogen. At 0° C., 800 µl (5 mmol) of trimethylsilyl hydride are added dropwise, followed by portionwise addition of 380 mg (0.64 mmol) of N-{4'-[(1R, 2S)-3-((S)-4-benzyl-2-oxooxazolidin-3-yl)-2-ethoxy-1-hydroxy-3-oxopropyl]biphenyl-3-ylmethyl}-N-methylbenzamide. After one hour at room temperature, the mixture is heated at 50° C. for 20 hours. The reaction medium is poured into water and extracted with ethyl acetate, and the organic phase is separated out after settling of the phases has taken place, dried over magnesium sulfate and evaporated. The residue obtained is purified by chromatography on a column of silica eluted with a mixture of heptane and ethyl acetate (70/30). 280 mg (76%) of the expected product are obtained.

(c) (S)-2-Ethoxy-3-(3'-{[methyl-(1-phenylmethanoyl) amino]methyl}biphenyl-4-yl)propionic acid 600 mg (1 mmol) of N-{4'-[(S)-3-((S)-4-benzyl-2-oxooxazolidin-3-yl)-2-ethoxy-3-oxopropyl]biphenyl-3-ylmethyl}-N-methylbenzamide and 10 ml of THF are introduced into a round-bottomed flask. At 0° C., 4.2 ml (2 mmol) of an aqueous lithium hydroxide solution (0.5M) are added and the mixture is stirred for one hour. The reaction medium is poured into water, acidified to pH 1 and extracted with ethyl acetate, and the organic phase is separated out after settling of the phases has taken place, dried over magnesium sulfate and evaporated. The residue obtained is purified by chromatography on a column of silica eluted with a mixture of heptane and ethyl acetate (50/50). 200 mg (47%) of (S)-2-ethoxy-3-(3'-{[methyl-(1-phenylmethanoyl)amino] methyl}biphenyl-4-yl)propionic acid, with a melting point of 53–54° C., are obtained.

EXAMPLE 14

Monomethyl 2-(3'-{[methyl-(1-phenylmethanoyl)-amino]methyl}biphenyl-4-ylmethyl)malonate (a) Diethyl 2-(3'-{[methyl-(1-phenylmethanoyl)-amino] methyl}biphenyl-4-ylmethylene)malonate 600 mg (1.8 mmol) of N-(4'-formylbiphenyl-3-ylmethyl)-N-methylbenzamide (prepared as in Example 1(e)), 10 ml of toluene, 300 µl (1.8 mmol) of diethyl malonate and 50 mg (0.35 mmol) of piperidine acetate are introduced into a three-necked flask under a stream of nitrogen. This mixture is refluxed for 6 hours, while separating out the water formed using Dean-Stark apparatus. The reaction medium is cooled, extracted with ethyl acetate and washed with water. The organic phase is separated out after settling has taken place, dried over magnesium sulfate and evaporated. The crude product is purified by chromatography on a column of silica eluted with a mixture of heptane and ethyl acetate (75/25). After evaporation of the solvents, 700 mg (84%) of expected product are collected.

(b) Diethyl 2-(3'-{[methyl-(1-phenylmethanoyl)-amino] methyl}biphenyl-4-ylmethyl)malonate 700 mg (1.5 mmol) of diethyl 2-(3'-{[methyl-(1-phenylmethanoyl)amino]methyl}biphenyl-4-ylmethylene) malonate, 7 ml of THF and 1 ml of methanol are introduced into a three-necked flask under a stream of nitrogen. The reaction medium is degassed, 80 mg of palladium-on-charcoal (5%) are introduced and the mixture is hydrogenated under atmospheric pressure at room temperature for 20 hours. The reaction medium is filtered through Celite and evaporated. The residue obtained is purified by chromatography on a column of silica eluted with a mixture of heptane and ethyl acetate (80/20). After evaporation of the solvents, 450 mg (63%) of the desired product are collected.

(c) Monomethyl 2-(3'-{[methyl-(1-phenyl-methanoyl) amino]methyl}biphenyl-4-ylmethyl)malonate 400 mg (0.85 mmol) of diethyl 2-(3'-{[methyl-(1-phenylmethanoyl)amino]methyl}biphenyl-4-yl-methylene) malonate, 5 ml of methanol and 100 mg of potassium carbonate are placed in a round-bottomed flask. This mixture is stirred at room temperature for 18 hours, acidified to pH 3 with sulfuric acid and extracted with ethyl acetate. The organic phase is dried over magnesium sulfate and evaporated. The residue obtained is purified by chromatography on a column of silica eluted with a mixture of heptane and ethyl acetate (70/30). After evaporation of the solvents, 160 mg (44%) of the desired product, with a melting point of 67° C., are collected.

EXAMPLE 15

Dimethyl 2-(3'-{[methyl-(1-phenylmethanoyl)-amino]methyl}biphenyl-4-ylmethyl)malonate (a) Dimethyl 2-(3'-{[methyl-(1-phenylmethanoyl)-amino]methyl}biphenyl-4-ylmethylene)malonate 1.4 g (4.25 mmol) of N-(4'-formylbiphenyl-3-ylmethyl)-N-methylbenzamide (prepared as in Example 1(e)), 20 ml of toluene, 560 mg (4.25 mmol) of dimethyl malonate and 125 mg (0.85 mmol) of piperidine acetate are introduced into a three-necked flask under a stream of nitrogen. The mixture is refluxed for 6 hours, while separating out the water formed using Dean-Stark apparatus. The reaction medium is cooled, extracted with ethyl acetate and washed with water. The organic phase is separated out after settling of the phases has taken place, dried over magnesium sulfate and evaporated. The crude product is purified by chromatography on a column of silica eluted with admixture of heptane and ethyl acetate (70/30). After evaporation of the solvents, 1.4 g (75%) of the expected product are collected.

(b) Dimethyl 2-(3'-{[methyl-(11-phenylmethanoyl)-amino]methyl}biphenyl-4-ylmethyl)malonate 1.3 g (2.9 mmol) of dimethyl 2-(3'-{[methyl-(1-phenylmethanoyl)amino]methyl}biphenyl-4-yl-methylene)malonate, 10 ml of dioxane and 2 ml of methanol are introduced into a three-necked flask under a stream of nitrogen. The reaction medium is degassed, 80 mg of palladium-on-charcoal (5%) are introduced and the mixture is hydrogenated under atmospheric pressure at room temperature for 8 hours. The reaction medium is filtered through Celite and evaporated. The residue obtained is purified by chromatography on a column of silica eluted with a mixture of heptane and ethyl acetate (60/40). After evaporation of the solvents, 1 g (78%) of the desired product are collected in the form of an oil.

EXAMPLE 16

Methyl 2-(3'-{[methyl-(1-phenylmethanoyl)-amino]methyl}biphenyl-4-ylmethyl)malonamate (a) Dimethyl 2-(3'-{[methyl-(1-phenylmethanoyl)-amino]methyl}biphenyl-4-ylmethylene)malonate 1.54 g (4.25 mmol) of N-(4'-formylbiphenyl-3-ylmethyl)-N-methylbenzamide (prepared as in Example 1(e)), 20 ml of toluene, 0.56 g (4.25 mmol)) of dimethyl malonate and 123 mg (0.85 mmol) of piperidine acetate are introduced into a three-necked flask under a stream of nitrogen. The mixture is refluxed for 5 hours, while separating off the water formed using Dean-Stark apparatus. The reaction medium is cooled, extracted with ethyl acetate and washed with water. The organic phase is separated out after settling of the phases has taken place, dried over magnesium sulfate and evaporated. The crude product is purified by chromatography on a column of silica eluted with a mixture of heptane and ethyl acetate (70/30). After evaporation of the solvents, 1.4 g (75%) of the expected product are collected.

(b) Dimethyl 2-(3'-{[methyl-(1-phenylmethanoyl)-amino]methyl}biphenyl-4-ylmethyl)malonate 1.3 g (2.9 mmol) of dimethyl 2-(3'-{[methyl-(1-phenylmethanoyl)amino]methyl}biphenyl-4-yl-methylene) malonate, 10 ml of dioxane and 2 ml of methanol are introduced into a three-necked flask under a stream of nitrogen. 76 mg of palladium-on-charcoal (5%) are added and the mixture is hydrogenated under atmospheric pressure for 8 hours. The reaction medium is filtered through Celite and evaporated. The residue obtained is purified by chromatography on a column of silica eluted with a mixture of heptane and ethyl acetate (60/40). 1 g (78%) of the desired product is obtained.

(c) Monomethyl 2-(3'-{[methyl-(1-phenyl-methanoyl)amino]methyl}biphenyl-4-ylmethyl)malonate 920 mg (2 mmol) of dimethyl 2-(3'-{[methyl-(1-phenylmethanoyl)amino]methyl}biphenyl-4-ylmethyl)-malonate (prepared in Example 15(b)), 4 ml of tetrahydrofuran and 8 ml of methanol are introduced into a round-bottomed flask. At 0° C., 0.24 ml (2.1 mmol) of aqueous 35% sodium hydroxide solution is added dropwise. The reaction medium is stirred for 18 hours, poured into water, acidified to pH 4–5 with 1N hydrochloric acid solution and extracted with ethyl acetate. After separation of the phases once settling has taken place, the organic phase is dried over magnesium sulfate, filtered and evaporated. 820 mg 10 (92%) of the desired product are obtained.

(d) Methyl 2-(3'-{[methyl-)1-phenylmethanoyl)-amino]methyl}biphenyl-4-ylmethyl malonamate 780 mg (1.8 mmol) of monomethyl 2-(3'-{[methyl-(1-phenylmethanoyl)amino]methyl}biphenyl-4-yl-methyl) malonate and 8 ml of dichloromethane are introduced into a three-necked flask under a stream of nitrogen. At 0° C., 180 μl (2 mmol) of oxalyl chloride are added dropwise, followed by stirring for 4 hours. The reaction medium is evaporated to dryness and the residue is placed in 2 ml of acetone and 1 ml of 32% aqueous ammonia solution. This reaction medium is stirred at room temperature for 2 hours, immersed in water, acidified to Ph and extracted with ethyl acetate. The organic phase is dried over magnesium sulfate, filtered and evaporated. The residue obtained is washed with a mixture of heptane and ether (50/50). 400 mg (52%) of the desired product, with a melting point of 62° C., are obtained.

EXAMPLE 17

N-[4'-(2,4-Dioxothiazolidin-5-ylmethyl)biphenyl-3-ylmethyl]-N-ethylbenzamide (a) N-(3-Bromo benzyl)benzamide 7 g (31.6 mmol) of 3-bromobenzylamine, 100 ml of THF and 9.6 ml (69.2 mmol) of triethylamine are placed in a three-necked flask under a stream of nitrogen. 4 ml (34.6 mmol) of benzoyl chloride are added dropwise and the mixture is stirred for 1 hour at room temperature. The reaction medium is extracted with ethyl acetate, washed with water, dried over magnesium sulfate, filtered and evaporated. 9.2 g (100%) of the desired product are obtained.

(b) N-(4'-Formylbiphenyl-3-ylmethyl)benzamide

In a manner similar to that of Example 1(e), by reacting 7.4 g (25.4 mmol) of N-(3-bromo benzyl)-benzamide with 5.7 g (38.2 mmol) of 4-formylbenzene-boronic acid, 4 g (50%) of the expected product are obtained.

(c) N-(4'-[1,3]Dioxolan-2-ylbiphenyl-3-yl-methyl) benzamide 3.2 g (10 mmol) of N-(4-formylbiphenyl-3-yl-methyl) benzamide, 50 ml of toluene, 2.8 ml (50 mmol) of ethylene glycol and 38 mg (0.2 mmol) of para-toluenesulfonic acid are introduced into a three-necked flask under a stream of nitrogen. The reaction medium is refluxed for 3 hours and the water formed is separated off using Dean-stark apparatus. The reaction medium is extracted with dichloromethane and washed with water, and the organic phase is separated out after settling of the phases has taken place. The organic phase is dried over magnesium sulfate and filtered. 3.7 g (100%) of the desired product are obtained.

(d) N-(4'-[1,3]Dioxolan-2-ylbiphenyl-3-ylmethyl)-N-ethylbenzamide 600 mg (1.7 mmol) of N-(4'-[1,3]dioxolan-2-ylbiphenyl-3-ylmethyl)benzamide, 5 ml of THF and 206 mg (1.85 mmol) of potassium tert-butoxide are introduced into a three-necked flask under nitrogen. 300 µl 15 (3.7 mmol) of iodoethane are added dropwise. The reaction mixture is stirred at room temperature for 3 hours, extracted with ethyl acetate, washed with water, dried over magnesium sulfate, filtered and evaporated. The residue obtained is purified by chromatography on a column of silica eluted with a mixture of heptane and ethyl acetate (70/30). 400 mg (64%) of the desired product are obtained.

(e) N-Ethyl-N-(4'-formylbiphenyl-3-ylmethyl)-benzamide 400 mg (1 mmol) of N-(4'-[1,3]dioxolan-2-yl-biphenyl-3-ylmethyl)-N-ethylbenzamide, 5 ml of methanol, 2 g of silica and a few drops of sulfuric acid are introduced into a round-bottomed flask. The mixture is stirred at room temperature for 24 hours. The reaction medium is poured into water and extracted with dichloromethane, and the organic phase is separated out after settling of the phases has taken place, dried over magnesium sulfate and evaporated. 320 mg (91%) of the desired product are obtained.

(f) N-[4'-(2,4-Dioxothiazolidin-5-ylidenemethyl)-biphenyl-3-ylmethyl]-N-ethylbenzamide In a manner similar to that of Example 1(f), by reacting 300 mg (0.9 mmol) of N-ethyl-N-(4'-formyl-biphenyl-3-ylmethyl)benzamide with 100 mg (0.9 mmol) of 2,4-thiazolidine dione, 340 mg (88%) of the expected product are obtained.

(g) N-[4'-(2,4-Dioxothiazolidin-5-ylmethyl)-biphenyl-3-ylmethyl-N-ethylbenzamide In a manner similar to that of Example 1(g), starting with 300 mg (0.7 mmol) of N-[4'-(2,4-dioxothiazolidin-5-ylidenemethyl)biphenyl-3-ylmethyl]-N-ethylbenzamide in 10 ml THF, 150 mg (50%) of N-[4'-(2,4-dioxothiazolidin-5-ylmethyl)biphenyl-3-ylmethyl-N-ethylbenzamide, with a melting point of 157° C., are obtained.

EXAMPLE 18

N-[4'-(2,4-Dioxothiazolidin-5-ylmethyl)biphenyl-3-ylmethyl]-N-pentylbenzamide (a) N-(4'-[1,3]Dioxolan-2-ylbiphenyl-3-ylmethyl)-N-pentylbenzamide In a manner similar to that of Example 17(d), starting with 1 g (2.8 mmol) of N-(4'-[1,3]dioxolan-2-ylbiphenyl-3-ylmethyl)benzamide (prepared in Example 17(c)) and 2.4 ml (18.3 mmol) of iodopentane, 600 mg (50%) of N-(4'-[1,3]dioxolan-2-ylbiphenyl-3-ylmethyl)-N-pentylbenzamide are obtained.

(b) N-(4'-Formylbiphenyl-3-ylmethyl)-N-pentylbenzamide

In a manner similar to that of Example 17(e), starting with 550 mg (1.2 mmol) of N-(4'-[1,3]dioxolan-2-ylbiphenyl-3-ylmethyl)-N-pentylbenzamide, 400 mg (82%) of N-(4'-formylbiphenyl-3-ylmethyl)-N-pentylbenzamide are obtained.

(c) N-[4'-(2,4-Dioxothiazolidin-5-ylidene-methyl)biphenyl-3-ylmethyl)-N-pentylbenzamide In a manner similar to that of Example 1(f), by reacting 320 mg (0.8 mmol) of N-(4'-formylbiphenyl-3-ylmethyl)benzamide with 100 mg (0.8 mmol) of 2,4-thiazolidine dione, 350 mg (87%) of the expected product are obtained.

(d) N-[4'-(2,4-Dioxothiazolidin-5-ylmethyl)-biphenyl-3-ylmethyl)-N-pentylbenzamide In a manner similar to that of Example 1(g), starting with 330 mg (0.7 mmol) of N-[4'-(2,4-dioxothiazolidin-5-ylidenemethyl)biphenyl-3-ylmethyl)-N-pentylbenzamide in 10 ml of ethyl acetate and 10 ml of ethanol, 220 mg (65%) of N-[4'-(2,4-dioxothiazolidin-5-ylmethyl)biphenyl-3-ylmethyl)-N-pentylbenzamide, with a melting point of 57° C., are obtained.

EXAMPLE 19 tert-Butyl [4'-(2,4-dioxothiazolidin-5-ylmethyl)-biphenyl-3-ylmethyl]ethylcarbamate (a) tert-Butyl (3-bromo benzyl)ethylcarbamate In a manner similar to that of Example 17(d), starting with 3 g (10.5 mol) of tert-butyl (3-bromo benzyl)carbamate (prepared as in Example 1(a)) and 4.2 ml (52.5 mmol) of iodoethane, 3.2 g (97%) of the desired product are obtained.

(b) tert-Butyl ethyl-(4'-formylbiphenyl-3-yl-methyl) carbamate

In a manner similar to that of Example 1(e), by reacting 3.2 g (10 mmol) of tert-butyl (3-bromo benzyl) ethylcarbamate with 2.3 g (15 mmol) of 4-formylbenzene boronic acid, 1.4 g (41%) of the expected product are obtained.

(c) tert-Butyl [4'-(2,4-dioxothiazolidin-5-ylidenemethyl) biphenyl-3-ylmethyl]ethylcarbamate In a manner similar to that of Example 1(f), by reacting 1.35 g (4 mmol) of tert-butyl ethyl(4'-formylbiphenyl-3-ylmethyl)carbamate with 470 mg (4 mmol) of 2,4-thiazolidine dione, 1.6 g (92%) of the expected product are obtained.

(d) tert-Butyl [4'-(2,4-dioxothiazolidin-5-yl-methyl) biphenyl-3-ylmethyl]ethylcarbamate In a manner similar to that of Example 1(g), starting with 500 mg (1.15 mmol) of tert-butyl [4'-(2,4-dioxothiazolidin-5-ylidenemethyl)biphenyl-3-ylmethyl]ethylcarbamate in 5 ml of ethyl acetate, 100 mg (20%) of the desired product with a melting point of 103° C. are obtained.

EXAMPLE 20 tert-Butyl [4'-(2,4-dioxothiazolidin-5-yl-methyl) biphenyl-3-ylmethyl]propylcarbamate (a) tert-Butyl [4'-(2,4-dioxothiazolidin-5-ylidenemethyl) biphenyl-3-ylmethyl]carbamate In a manner similar to that of Example 1(f) by reacting 7.4 g (24 mmol) of tert-butyl (4'-formyl-biphenyl-3-ylmethyl) carbamate (prepared as in Example 1(e) from tert-butyl (3-bromo benzyl)carbamate)with 2.8 g (24 mmol) of 2,4-thiazolidine dione, 9 g (95%) of the expected product are obtained.

(b) tert-Butyl [4'-(2,4-dioxothiazolidin-5-ylidenemethyl) biphenyl-3-ylmethyl]propylcarbamate In a manner similar to that of Example 17(d), starting with 700 mg (1.7 mmol) of tert-butyl [4'-(2,4-dioxothiazolidin-5-ylidenemethyl)biphenyl-3-ylmethyl]carbamate and 350 µl (3.8 mmol) of 1-bromopropane, 600 mg (78%) of the desired product are obtained.

(c) tert-Butyl [4'-(2,4-dioxothiazolidin-5-ylmethyl) biphenyl-3-ylmethyl]propylcarbamate In a manner similar to that of Example 1(g), starting with 600 mg (1.3 mmol) of tert-butyl [4'-(2,4-dioxothiazolidin-5-ylidenemethyl)biphenyl-3-ylmethyl]-propylcarbamate in 7 ml of ethyl acetate and 7 ml of dimethylformamide, 50 mg (10%) of the desired product are obtained.

EXAMPLE 21

9H-Fluoren-9-ylmethyl [4'-(2,4-dioxothiazolidin-5-ylmethyl)biphenyl-3-ylmethyl]methylcarbamate (a) 9H-Fluoren-9-ylmethyl [4'-(2,4-dioxo-thiazolidin-5-ylidenemethyl)biphenyl-3-ylmethyl]-methylcarbamate 500 mg (0.9 mmol) of 5-(3'-methylaminomethyl-biphenyl-4-ylmethylene)thiazolidine-2,4-dione (prepared in Example 12(c)) in 12 ml of aqueous 10% sodium carbonate solution are introduced into a round-bottomed flask. At 0° C., 240 mg of 9H-fluoren-9-ylmethyl chloride in 5 ml of dioxane are added dropwise. The mixture is stirred from 0° C. to room temperature for 4 hours. The reaction medium is immersed in water and extracted with ethyl acetate, after acidification to pH 4. The organic phase is dried over magnesium sulfate, filtered and evaporated. 490 mg (100%) of the expected product are obtained.

(b) 9H-Fluoren-9-ylmethyl [4'-(2,4-dioxo-thiazolidin-5-ylmethyl)biphenyl-3-ylmethyl]-methylcarbamate In a manner similar to that of Example 1(g), starting with 500 mg (0.9 mmol) of 9H-fluoren-9-ylmethyl [4'-(2,4-dioxothiazolidin-5-ylidenemethyl)biphenyl-3-ylmethyl] methylcarbamate in 10 ml of dioxane, 200 mg (40%) of the desired product, with a melting point of 94° C., are obtained.

EXAMPLE 22

N-[4'-(2,4-Dioxothiazolidin-5-ylmethyl)biphenyl-3-ylmethyl]-2,2,N-trimethylpropionamide (a) N-[4'-(2,4-Dioxothiazolidin-5-ylidenemethyl)-biphenyl-3-ylmethyl]-2,2,N-trimethylpropionamide In a manner similar to that of Example 1(d), by reacting 500 mg (0.9 mmol) of 5-(3'-methylaminomethylbiphenyl-4-ylmethylene)thiazolidine-2,4-dione (prepared in Example 12(c)) with 0.3 ml (2.3 mmol) of 2,2-dimethylpropionyl chloride, 240 mg (65%) of the expected product are obtained.

(b) N-[4'-(2,4-Dioxothiazolidin-5-ylmethyl)-biphenyl-3-ylmethyl]-2,2, N-trimethylpropionamide In a manner similar to that of Example 1(g), starting with 240 mg (0.6 mmol) of N-[4'-(2,4-dioxothiazolidin-5-ylidenemethyl)biphenyl-3-ylmethyl]-2,2-N-trimethylpropionamide in 20 ml of tetrahydrofuran, 100 mg (40%) of the desired product, with a melting point of 78° C., are obtained.

EXAMPLE 23

N-Octyl-4'-(2,4-dioxothiazolidin-5-ylmethyl)-biphenyl-3-carboxamide (a) Ethyl 4'-formylbiphenyl-3-carboxylate In a manner similar to that of Example 1(e), by reacting 12.6 ml (79 mmol) of ethyl 3-bromobenzoate with 15 g (100 mmol) of 4-formylbenzene boronic acid, 12 g (60%) of the expected product are obtained.

(b) Ethyl 4'-(2,4-dioxothiazolidin-5-ylidenemethyl) biphenyl-3-carboxylate

In a manner similar to that of Example 1(f), by reacting 11.7 g (46 mmol) of ethyl 4'-formylbiphenyl-3-carboxylate with 5.4 g (46 mmol) of 2,4-thiazolidine dione, 13 g (83%) of the expected product are obtained.

(c) 4'-(2,4-Dioxothiazolidin-5-ylidene-methyl)biphenyl-3-carboxylic acid 12.6 g (37 mmol) of ethyl 4'-(2,4-dioxo-thiazolidin-5-ylidenemethyl)biphenyl-3-carboxylate, 150 ml of tetrahydrofuran, 15 ml of methanol, a few drops of water and 7.4 g (186 mmol) of sodium hydroxide pellets are introduced into a round-bottomed flask. The mixed is refluxed for 18 hours. The reaction medium is placed in water, acidified to pH 2 and extracted with ethyl acetate. The organic phase is dried over magnesium sulfate, filtered and evaporated. 11.4 g (94%) of the desired product are obtained.

(d) N-Octyl-4'-(2,4-dioxothiazolidin-5-ylidene-methyl) biphenyl-3-carboxamide 1 g (3.1 mmol) of 4'-(2,4-dioxothiazolidin-5-ylidenemethyl)biphenyl-3-carboxylic acid, 15 ml of dimethylformamide, 460 mg (3.4 mmol) of 1-hydroxybenzotriazole and 500 µl (3.1 mmol) of n-octylamine are introduced into a three-necked flask under a stream of nitrogen. At 0° C., 0.59 g (3.4 mmol) of 1-(3-dimethylaminopropyl)-3-ethylcarbodiimide hydrochloride is added portionwise. The mixture is stirred for three days while allowing the temperature to rise. The reaction medium is poured into water and extracted with ethyl acetate, dried over magnesium sulfate, filtered and evaporated. 450 mg (33%) of the desired product are obtained.

(e) N-Octyl-4'-(2,4-dioxothiazolidin-5-ylmethyl)-biphenyl-3-carboxamide 150 mg (0.35 mmol) of N-octyl-4'-(2,4-dioxo-thiazolidin-5-ylidenemethyl)biphenyl-3-carboxamide, 20 ml of dimethylformamide and 150 mg of palladium-on-charcoal (10%) are introduced into a reactor under a stream of nitrogen. The medium is heated at 80° C. and hydrogenated under a pressure of 3 atm for 5 hours. The reaction medium is filtered through Celite. The filtrate is placed in water, extracted with ethyl acetate and washed thoroughly with water. The organic phase is dried over magnesium sulfate, filtered and evaporated. The residue is chromatographed on a column of silica, eluted with a mixture of heptane and ethyl acetate (30/70). 100 mg (65%) of the expected product, with a melting point of 137–138° C., are obtained.

EXAMPLE 24

N-[4'-(2,4-Dioxothiazolidin-5-ylmethyl)biphenyl-3-ylmethyl]-N-methyl-3-phenylpropionamide (a) N-[4'-(2,4-Dioxothiazolidin-5-ylidene-methyl) biphenyl-3-ylmethyl]-N-methyl-3-phenyl-propionamide In a manner similar to that of Example 1(d), by reacting 500 mg (0.9 mmol) of 5-(3'-methylaminomethylbiphenyl-4-ylmethylene)thiazolidine-2,4-dione (prepared in Example 10(c)) with 0.35 ml (2.3 mmol) of 3-phenylpropionyl chloride, 220 mg (54%) of the expected product are obtained.

(b) N-[4'-(2,4-Dioxothiazolidin-5-ylmethyl)-biphenyl-3-ylmethyl]-N-methyl-3-phenylpropionamide In a manner similar to that of Example 1(g), starting with 210 mg (0.45 mmol) of N-[4'-(2,4-dioxothiazolidin-5-ylidenemethyl)biphenyl-3-ylmethyl]-N-methyl-3-phenylpropionamide in 15 ml of tetrahydrofuran, 95 mg (45%) of the desired product, with a melting point of 325° C., are obtained.

EXAMPLE 25

2-[4'-(2,4-Dioxothiazolidin-5-ylmethyl)biphenyl-3-yl]-N-methyl-3-phenylacetamide (a) 2-(3-Bromophenyl)-N-methyl-N-phenylacetamide 6 g (28 mmol) of (3-bromophenyl)acetic acid in 50 ml of dichloromethane are introduced into a three-necked flask under a stream of nitrogen. At 0° C., 2.7 ml (28 mmol) of oxalyl chloride are added dropwise and the mixture is then stirred at room temperature for 18 hours. The reaction medium is evaporated to dryness and the residue is placed in 10 ml of tetrahydrofuran and added dropwise to a mixture of 3.2 g (28 mmol) of N-methylaniline, 50 ml of tetrahydrofuran and 4.6 ml (33 mmol) of triethylamine. The reaction medium is stirred at room temperature overnight, immersed in water and extracted with ethyl acetate. After separation of the phases once settling has taken place, the organic phase is dried over magnesium sulfate, filtered and evaporated. 5.7 g (67%) of the desired product, with a melting point of 60° C., are obtained.

(b) 2-(4'-Acetylbiphenyl-3-yl)-N-methyl-N-phenylacetamide

In a manner similar to that of Example 1(e), by reacting 2.9 g (9.5 mmol) of 2-(3-bromophenyl)-N-methyl-N-phenylacetamide with 2.2 g (14.2 mmol) of 4-formylbenzene boronic acid, 2.25 g (95%) of the expected product are obtained.

(c) 2-[4'-(2,4-Dioxothiazolidin-5-ylidene-methyl) biphenyl-3-yl]-N-methyl-N-phenylacetamide In a manner similar to that of Example 1(f), by reacting 1 g (4 mmol) of 2-(4'-acetylbiphenyl-3-yl)-N-methyl-N-phenylacetamide with 460 mg (4 mmol) of 2,4-thiazolidine dione, 1.2 g (71%) of the expected product are obtained.

(d) 2-[4'-(2,4-Dioxothiazolidin-5-ylmethyl)-biphenyl-3-yl)-N-methyl-N-phenylacetamide In a manner similar to that of Example 1(g), starting with 1.1 g (2.6 mmol) of 2-[4'-(2,4-dioxothiazolidin-5-ylidenemethyl)biphenyl-3-yl]-N-methyl-N-phenylacetamide in 20 ml of ethyl acetate and 20 ml of ethanol, 660 mg (60%) of the desired product, with a melting point of 158° C., are obtained.

EXAMPLE 26

N-[4'-(2,4-Dioxothiazolidin-5-ylidenemethyl)-biphenyl-3-ylmethyl]-N-propylbenzamide (a) tert-Butyl (3-bromo benzyl)propylcarbamate In a manner similar to that of Example 17(d), starting with 3 g (10.5 mmol) of tert-butyl (3-bromo-benzyl) carbamate and 1.15 ml (11.5 mmol) of iodopropane, 3.35 g (97%) of the desired product are obtained.

(b) (3-Bromo benzyl)propylamine

In a manner similar to that of Example 10(c), starting with 2 g (6 mmol) of tert-butyl (3-bromo-benzyl) propylcarbamate, 1.3 g (92%) of the desired product are obtained.

(c) N-(3-Bromo benzyl)-N-propylbenzamide

In a manner similar to that of Example 1(d), by reacting 1.3 g (5.6 mmol) of (3-bromo benzyl)propylamine with 700 μl (6.2 mmol) of benzoyl chloride, 1.4 g (74%) of the expected product are obtained.

(d) N-(4'-Formylbiphenyl-3-ylmethyl)-N-propylbenzamide

In a manner similar to that of Example 1(e), by reacting 1.4 g (4.2 mmol) of N-(3-bromo benzyl)-N-propylbenzamide with 940 mg (6.2 mmol) of 4-formylbenzene boronic acid, 780 mg (53%) of the expected product are obtained.

(e) N-[4'-(2,4-Dioxothiazolidin-5-ylidenemethyl)-biphenyl-3-ylmethyl]-N-propylbenzamide In a manner similar to that of Example 1(f), by reacting 580 mg (1.6 mmol) of N-(4'-formylbiphenyl-3-ylmethyl)-N-propylbenzamide with 190 mg (1.6 mmol) of 2,4-thiazolidine dione, 530 mg (72%) of the expected product, with a melting point of 250–251° C., are obtained.

EXAMPLE 27 tert-Butyl [4'-(2,4-dioxothiazolidin-5-ylmethyl)-biphenyl-3-yl]carbamate (a) tert-Butyl (3-bromophenyl)carbamate ml of 3-bromoaniline in 300 ml of tetrahydrofuran are introduced into a three-necked flask under a stream of nitrogen. 8.4 g (209 mmol) of sodium hydride (60% in oil) are added portionwise and the mixture is stirred until the evolution of gas has ceased. 38 g (174.5 mmol) of di-tert-butyl dicarbonate are then added dropwise. The mixture is refluxed for 36 hours. The reaction medium is immersed in water and extracted with ethyl acetate. After separation of the phases once settling has taken place, the organic phase is dried over magnesium sulfate, filtered and evaporated. 43 g (92%) of the desired product are obtained.

(b) tert-Butyl (4'-formylbiphenyl-3-yl)carbamate

In a manner similar to that of Example 1(e), 20 by reacting 19.3 g (71 mmol) of tert-butyl (3-bromo-phenyl) carbamate with 16 g (107 mmol) of 4-formylbenzene boronic acid, 21 g (63%) of the expected product are obtained.

(c) tert-Butyl [4'-(2,4-dioxothiazolidin-5-ylidenemethyl) biphenyl-3-yl]carbamate In a manner similar to that of Example 1(f), by reacting 9.5 g (32 mmol) of tert-butyl (4'-formyl-biphenyl-3-yl) carbamate with 3.8 g (32 mmol) of 2,4-thiazolidine dione, 12.7 g (91%) of the expected product are obtained.

(d) tert-Butyl [4'-(2,4-dioxothiazolidin-5-yl-methyl) biphenyl-3-yl]carbamate

In a manner similar to that of Example 1(g), starting with 700 mg (1.8 mmol) of tert-butyl [4'-(2,4-dioxothiazolidin-5-ylidenemethyl)biphenyl-3-yl]carbamate in 10 ml of dioxane, 700 mg (60%) of the desired product, with a melting point of 158° C., are obtained.

EXAMPLE 28

N-[4'-(2,4-Dioxothiazolidin-5-ylmethyl)biphenyl-3-ylmethyl]-3,4-diethoxy-N-methylbenzamide (a) N-[4'-(2,4-Dioxothiazolidin-5-ylidene-methyl) biphenyl-3-ylmethyl]-3,4-diethoxy-N-methylbenzamide In a manner similar to that of Example 1(d), by reacting 500 mg (0.9 mmol) of 5-(3'-methylamino-methylbiphenyl-4-ylmethylene)thiazolidine-2,4-dione (prepared in Example 10(c)) with 520 mg (2.3 mmol) of 3,4-diethoxybenzoyl chloride, 370 mg (80%) of the expected product are obtained.

(b) N-[4'-(2,4-Dioxothiazolidin-5-ylmethyl)-biphenyl-3-ylmethyl]-3,4-diethoxy-N-methylbenzamide In a manner similar to that of Example 1(g), starting with 360 mg (0.7 mmol) of N-[4'-(2,4-dioxothiazolidin-5-ylidenemethyl)biphenyl-3-ylmethyl]-3,4-diethoxy-N-methylbenzamide in 15 ml of methanol, 150 mg (40%) of the desired product, with a melting point of 66° C., are obtained.

EXAMPLE 29

2-(3'-{[ethyl-(1-phenylmethanoyl)amino]methyl}-biphenyl-4-ylmethyl)malonamic acid 180 mg (0.4 mmol) of methyl 2-(3'-{[methyl-(1-phenylmethanoyl)amino]methyl}biphenyl-4-ylmethyl)malonamate (prepared in Example 16(d)) in 2 ml of methanol, 2 ml of tetrahydrofuran and 250 µl (0.5 mmol) of aqueous 2N sodium hydroxide solution are introduced [lacuna]. The reaction medium is stirred at room temperature for 36 hours, acidified to pH 3 with hydrochloric acid solution and extracted with ethyl acetate. The organic phase is dried over magnesium sulfate, filtered and evaporated. 80 mg (46%) of the desired product, with a melting point of 117° C., are obtained.

EXAMPLE 30

N-Benzyl-N-methyl-4'-(2,4-dioxothiazolidin-5-ylmethyl)biphenyl-3-carboxamide (a) N-Benzyl-N-methyl-4'-(2,4-dioxothiazolidin-5-ylidenemethyl)biphenyl-3-carboxamide 500 mg (1.54 mmol) of 4'-(2,4-dioxothiazolidin-5-ylidenemethyl)biphenyl-3-carboxylic acid (prepared in Example 23(c)), 5 ml of dimethylformamide, 230 mg (1.7 mmol) of 1-hydroxybenzotriazole and 200 µl (1.5 mmol) of benzylmethylamine are introduced into at three-necked flask under a stream of nitrogen. At 0° C., 350 mg (1.7 mmol) of dicyclohexylcarbodiimide are added portionwise. The mixture is stirred for 18 hours while allowing the temperature to rise. The reaction medium is immersed in water, extracted with ethyl acetate, dried over magnesium sulfate, filtered and evaporated. The residue obtained is washed with dichloromethane and filtered. 400 mg (61%) of the desired product are obtained.

(b) N-Benzyl-N-methyl-4'-(2,4-dioxothiazolidin-5-ylmethyl)biphenyl-3-carboxamide In a manner similar to that of Example 1(g), starting with 400 mg (0.9 mmol) of N-benzyl-N-methyl-4'-(2,4-dioxothiazolidin-5-ylidenemethyl)biphenyl-3-carboxamide in 5 ml of dioxane, 170 mg (43%) of the desired product, with a melting point of 66° C., are obtained.

EXAMPLE 31

N-Benzyl-4'-(2,4-dioxothiazolidin-5-ylmethyl)-biphenyl-3-carboxamide (a) N-Benzyl-4'-(2,4-dioxothiazolidin-5-ylidene-methyl)biphenyl-3-carboxamide 600 mg (1.84 mmol) of 4'-(2,4-dioxo-thiazolidin-5-ylidenemethyl)biphenyl-3-carboxylic acid (prepared in Example 23(c)), 5 ml of dimethylformamide, 340 mg (2.5 mmol) of 1-hydroxybenzotriazole and 250 µl (2.3 mmol) of benzylamine are introduced into a three-necked flask under a stream of nitrogen. At 0° C., 480 mg (2.5 mmol) of 1-(3-dimethylaminopropyl)-3-ethyl-carbodiimide hydrochloride are added portionwise. The mixture is stirred for 24 hours while allowing the temperature to rise. The reaction medium is immersed in water, extracted with ethyl acetate, dried over magnesium sulfate, filtered and evaporated. The residue obtained is washed with dichloromethane and filtered. 460 mg (60%) of the desired product are obtained.

(b) N-Benzyl-4'-(2,4-dioxothiazolidin-5-yl-methyl)biphenyl-3-carboxamide

In a manner similar to that of Example 1(g), starting with 430 mg (1 mmol) of N-benzyl-4'-(2,4-dioxothiazolidin-5-ylidenemethyl)biphenyl-3-carboxamide in 7 ml of dimethylformamide, 100 mg (23%) of the desired product, with a melting point of 148° C., are obtained.

EXAMPLE 32

N-[4'-(2,4-Dioxothiazolidin-5-ylmethyl)biphenyl-3-ylmethyl]-N-methyldecanamide (a) N-[4'-(2,4-Dioxothiazolidin-5-ylidenemethyl)-biphenyl-3-ylmethyl]-N-methyldecanamide In a manner similar to that of Example 1(d), by reacting 1 g (1.8 mmol) of 5-(3'-methylaminomethylbiphenyl-4-ylidenemethyl)thiazolidine-2,4-dione (prepared in Example 10(c)) with 410 µl (2 mmol) of decanoyl chloride, 500 mg (60%) of the expected product are obtained.

(b) N-[4'-(2,4-Dioxothiazolidin-5-ylmethyl)-biphenyl-3-ylmethyl]-N-methyldecanamide In a manner similar to that of Example 1(g), starting with 460 mg (1 mmol) of N-[4'-(2,4-dioxothiazolidin-5-ylidenemethyl)biphenyl-3-ylmethyl]-N-methyldecanamide in 8 ml of dioxane, 300 mg (65%) of the desired product are obtained in the form of a film.

EXAMPLE 33

N-[4'-(2,4-Dioxothiazolidin-5-ylmethyl)biphenyl-3-yl]-2-phenylacetamide (a) 5-(3'-Aminobiphenyl-4-ylmethylene)-thiazolidine-2,4-dione In a manner similar to that of Example 10c, starting with 5 g (13 mmol) of tert-butyl [4'-(2,4-dioxothiazolidin-5-ylidenemethyl)biphenyl-3-yl]carbamate (prepared in Example 27(c)), 5.2 g (100%) of the expected product are obtained.

(b) N-[4'-(2,4-Dioxothiazolidin-5-ylidenemethyl)-biphenyl-3-yl]-2-phenylacetamide In a manner similar to that of Example 1(d), by reacting 1.2 g (2.3 mmol) of 5-(3'-aminobiphenyl-4-ylmethylene)thiazolidine-2,4-dione with 430 µl (3 mmol) of phenylacetyl chloride, 920 mg (97%) of the expected product are obtained.

(c) N-[4'-(2,4-Dioxothiazolidin-5-ylidenemethyl)-biphenyl-3-yl]-2-phenylacetamide In a manner similar to that of Example 1(g), starting with 580 mg (1.4 mmol) of N-[4'-(2,4-dioxothiazolidin-5-ylidenemethyl)biphenyl-3-yl]-2-phenylacetamide in 10 ml of a dioxane/methanol mixture (50/50) under 3 atm, 140 mg (15%) of the desired product, with a melting point of 165° C., are obtained.

EXAMPLE 34

N-[4'-(2,4-Dioxothiazolidin-5-ylmethyl)biphenyl-3-ylmethyl]-N-methyloctanamide (a) N-[4'-(2,4-Dioxothiazolidin-5-ylidenemethyl)-biphenyl-3-ylmethyl]-N-methyloctanamide In a manner similar to that of Example 1(d), by reacting 500 mg (0.9 mmol) of 5-(3'-methylamino-methylbiphenyl-4-ylidenemethyl)thiazolidine-2,4-dione prepared in Example 10c with 170 µl (1 mmol) of octanoyl chloride, 250 mg (62%) of the expected product are obtained.

(b) N-[4'-(2,4-Dioxothiazolidin-5-ylmethyl)-biphenyl-3-ylmethyl]-N-methyloctanamide In a manner similar to that of Example 1(g), starting with 220 mg (0.5 mmol) of N-[4'-(2,4-dioxothiazolidin-5-

29 ylidenemethyl)biphenyl-3-ylmethyl]-N-methyloctanamide in 10 ml of dioxane, 120 mg (53%) of the desired product, with a melting point of 36° C., are obtained.

EXAMPLE 35

N-[4'-(2,4-Dioxothiazolidin-5-ylmethyl)biphenyl-3-ylmethyl]-N-methylheptanamide (a) N-[4'-(2,4-Dioxothiazolidin-5-ylidenemethyl)-biphenyl-3-ylmethyl]-N-methylheptanamide In a manner similar to that of Example 1(d), by reacting 1 g (1.8 mmol) of 5-(3'-methylaminomethyl-biphenyl-4-ylidenemethyl)thiazolidine-2,4-dione (prepared in Example 10(c)) with 300 μl (2 mmol) of heptanoyl chloride, 450 mg (57%) of the expected product are obtained.

(b) N-[4'-(2,4-Dioxothiazolidin-5-ylmethyl)-biphenyl-3-ylmethyl]-N-methylheptanamide In a manner similar to that of Example 1(g), starting with 360 mg (0.8 mmol) of N-[4'-(2,4-dioxothiazolidin-5-ylidenemethyl)biphenyl-3-ylmethyl]-N-methylheptanamide in 15 ml of dioxane, under 3 atm, 230 mg (66%) of the desired product are obtained in the form of a colorless film.

EXAMPLE 36

N-Hydroxy-2-(3'-{[methyl-(1-phenylmethanoyl)-amino]methyl}biphenyl-4-ylmethyl)malonamic acid A mixture of 130 mg (0.3 mmol) of dimethyl 2-(3'{[methyl-(1-phenylmethanoyl)amino]methyl}biphenyl-4-ylmethyl)malonate (prepared in Example 15(b)), 2 ml of methanol, 2 ml of tetrahydrofuran, 480 mg of sodium carbonate (4.5 mmol) and 200 mg (1.5 mmol) of hydroxylamine hydrochloride is heated at 60° C. for 18 hours. The reaction medium is neutralized to pH 6–7 with hydrochloric acid solution and extracted with ethyl acetate. The organic phase is dried over magnesium sulfate, filtered and evaporated. The residue obtained is purified by chromatography on a column of silica, eluted with a mixture of heptane and ethyl acetate (75/25). 90 mg (72%) of the desired product, with a melting point of 60° C., are obtained.

EXAMPLE 37

N-[4'-(2,4-Dioxothiazolidin-5-ylmethyl)biphenyl-3-ylmethyl]-N-methyl-2-phenylacetamide (a) tert-Butyl (4'-formylbiphenyl-3-ylmethyl)-methylcarbamate In a manner similar to that of Example 1(e), starting with 125 g (410 mmol) of tert-butyl (3-bromo benzyl)-N-methylcarbamate (prepared in Example 1(b)) and 82 g (510 mmol) of 4-formylbenzene boronic acid, 90 g (67%) of the desired product are obtained.

(b) tert-Butyl [4'-(2,4-Dioxothiazolidin-5-ylidenemethyl) biphenyl-3-ylmethyl]methylcarbamate In a manner similar to that of Example 1(f), starting with 75 g (230 mmol) of tert-butyl (4'-formylbiphenyl-3-ylmethyl)methylcarbamate and 35 g (275 mmol) of 2,4-thiazolidine dione, 84 g (86%) of the expected product are obtained.

(c) tert-Butyl (4'-(2,4-dioxothiazolidin-5-ylmethyl) biphenyl-3-ylmethyl]methylcarbamate 30 g (71 mmol) of tert-butyl [4'-(2,4-dioxothiazolidin-5-ylidenemethyl)biphenyl-3-ylmethyl]methylcarbamate in 500 ml of dioxane are placed in a reactor. The reaction medium is degassed, followed by addition of g (1 equivalent by mass) of 10% palladium-on-charcoal. The system is placed under 3 bar of hydrogen and heated at 50° C. for seven hours. The reaction medium is filtered through Celite and evaporated, and the residue obtained is purified by chromatography on a column of silica with an fluent mixture of dichloromethane and methanol (98/2). After evaporation of the solvents, 18 g (60%) of the expected product are collected.

(d) 5-(3'-Methylaminomethylbiphenyl-4-yl-methyl) thiazolidine-2,4-dione 16 ml (210 mmol) of trifluoroacetic acid are added to a solution of 18 g (42 mmol) of tert-butyl 4'-(2,4-dioxothiazolidin-5-ylmethyl)biphenyl-3-ylmethyl]-methylcarbamate in 250 ml of dichloromethane. The reaction medium is stirred at room temperature for 18 hours and is then evaporated to dryness. The residue obtained is washed with ethyl acetate and dried. 14 g (78%) of product in the form of the trifluoroacetate are collected.

(e) N-[4'-(2,4-Dioxothiazolidin-5-ylmethyl)-biphenyl-3-ylmethyl]-N-methyl-2-phenylacetamide 500 mg (1.1 mmol) of 5-(3'-methylaminomethyl-biphenyl-4-ylmethyl)thiazolidine-2,4-dione trifluoroacetate, 2 ml of tetrahydrofuran and 500 μl (3.3 mmol) of triethylamine are introduced into a round-bottomed flask under a stream of nitrogen. 230 μl of phenylacetyl chloride are added dropwise and the mixture is stirred at room temperature for one hour. The reaction medium is poured into water and extracted with ethyl acetate, and the organic phase is separated out after settling of the phases has taken place, washed with water, dried over magnesium sulfate and evaporated. The residue obtained is purified by chromatography on a column of silica eluted with a mixture of dichloromethane and methanol (97/3). 360 mg(72%) of N-[4'-(2,4-dioxothiazolidin-5-ylmethyl)-biphenyl-3-ylmethyl]-N-methyl-2-phenylacetamide are obtained in the form of a white solid with a melting point of 73° C.

EXAMPLE 38

N-[4'-(2,4-Dioxothiazolidin-5-ylmethyl)biphenyl-3-ylmethyl]-4-methoxy-N-methylbenzamide In a manner similar to that of Example 37(e), by reacting 500 mg (1.1 mmol) of 5-(3'-methylaminomethylbiphenyl-4-ylmethyl)thiazolidine-2,4-dione trifluoroacetate with 170 μl (1.25 mmol) of 4-methoxybenzoyl chloride, and after purification, 300 mg (50%) of N-[4'-(2,4-dioxothiazolidin-5-ylmethyl)-biphenyl-3-ylmethyl]-4-methoxy-N-methylbenzamide are obtained in the form of a white solid with a melting point of 170° C.

EXAMPLE 39

N-[4'-(2,4-Dioxothiazolidin-5-ylmethyl)biphenyl-3-ylmethyl]-3-methoxy-N-methylbenzamide In a manner similar to that of Example 37(e), by reacting 540 mg (1.2 mmol) of 5-(3'-methylaminomethylbiphenyl-4-ylmethyl)thiazolidine-2,4-dione trifluoroacetate with 300 μl (2 mmol) of 3-methoxybenzoyl chloride, and after purification, 400 mg (70%) of N-[4'-(2,4-dioxothiazolidin-5-ylmethyl)-biphenyl-3-ylmethyl]-3-methoxy-N-methylbenzamide are obtained in the form of a white solid with a melting point of 173° C.

EXAMPLE 40

N-[4'-(2,4-Dioxothiazolidin-5-ylmethyl)biphenyl-3-ylmethyl]-3-N-dimethylbenzamide In a manner similar to that of Example 37(e), by reacting 500 mg (1.1 mmol) of 5-(3'-methylaminomethylbiphenyl- 4-ylmethyl)thiazolidine-2,4-dione trifluoroacetate with 170 µl (1.25 mmol) of 3-methylbenzoyl chloride, and after purification, 350 mg (70%) of N-[4'-(2,4-dioxothiazolidin-5-ylmethyl)biphenyl-3-ylmethyl]-3-N-dimethylbenzamide are obtained in the form of a white solid with a melting point of 98° C.

EXAMPLE 41

N-[4'-(2,4-Dioxothiazolidin-5-ylmethyl)biphenyl-3-ylmethyl]-N-methyl-4-propylbenzamide In a manner similar to that of Example 37(e), by reacting 500 mg (1.1 mmol) of 5-(3'-methylaminomethylbiphenyl-4-ylmethyl)thiazolidine-2,4-dione trifluoroacetate with 210 µl (1.2 mmol) of 4-propylbenzoyl chloride and after purification, 300 mg (55%) of N-[4'-(2,4-dioxothiazolidin-5-ylmethyl)-biphenyl-3-ylmethyl]-N-methyl-4-propylbenzamide, with a melting point of 280° C., are obtained.

EXAMPLE 42

N-[4'-(2,4-Dioxothiazolidin-5-ylmethyl)biphenyl-3-ylmethyl]-4,N-dimethylbenzamide In a manner similar to that of Example 37(e), by reacting 500 mg (1.1 mmol) of 5-(3'-methylaminomethylbiphenyl-4-ylmethyl)thiazolidine-2,4-dione trifluoroacetate with 170 µl (1.25 mmol) of 4-methylbenzoyl chloride, and after purification, 350 mg (70%) of N-[4'-(2,4-dioxothiazolidin-5-ylmethyl)biphenyl-3-ylmethyl]-4, N-dimethylbenzamide are obtained in the form of a white solid with a melting point of 198° C.

EXAMPLE 43

N-[4'-(2,4-Dioxothiazolidin-5-ylmethyl)biphenyl-3-ylmethyl]-N-methylisoxazole-5-carboxamide In a manner similar to that of Example 37(e), by reacting 500 mg (1.1 mmol) of 5-(3'-methylaminomethylbiphenyl-4-ylmethyl)thiazolidine-2,4-dione trifluoroacetate with 170 mg (1.3 mmol) of 5-isoxazolecarboxylic acid chloride, and after purification, 120 mg (26%) of N-[4'-(2,4-dioxothiazolidin-5-ylmethyl)biphenyl-3-ylmethyl]-N-methylisoxazole-5-carboxamide are obtained in the form of a white solid with a melting point of 160° C.

EXAMPLE 44

N-[4'-(2,4-Dioxothiazolidin-5-ylmethyl)biphenyl-3-ylmethyl]-4-ethoxy-N-methylbenzamide In a manner similar to that of Example 37(e), by reacting 1 g (2.2 mmol) of 5-(3'-methylaminomethyl-biphenyl-4-ylmethyl)thiazolidine-2,4-dione trifluoro-acetate with 460 mg (2.5 mmol) of 4-ethoxybenzoyl chloride, and after purification, 960 mg (88%) of N-[4'-(2,4-dioxothiazolidin-5-ylmethyl)biphenyl-3-ylmethyl]-4-ethoxy-N-methylbenzamide are obtained in the form of a white solid with a melting point of 182° C.

EXAMPLE 45

N-[4'-(2,4-Dioxothiazolidin-5-ylmethyl)biphenyl-3-ylmethyl]-4-fluoro-N-methylbenzamide In a manner similar to that of Example 37(e), by reacting 1 g (2.2 mmol) of 5-(3'-methylaminomethyl-biphenyl-4-ylmethyl)thiazolidine-2,4-dione trifluoro-acetate with 290 µl (2.5 mmol) of 4-fluorobenzoyl chloride, and after purification, 1 g (98%) of N-[4'-(2,4-dioxothiazolidin-5-ylmethyl)biphenyl-3-ylmethyl]-4-fluoro-N-methylbenzamide, with a melting point of 212° C., is obtained.

EXAMPLE 46

4-Dimethylamino-N-[4'-(2,4-dioxothiazolidin-5-ylmethyl)biphenyl-3-ylmethyl]-N-methylbenzamide In a manner similar to that of Example 37(e), by reacting 1 g (2.2 mmol) of 5-(3'-methylaminomethyl-biphenyl-4-ylmethyl)thiazolidine-2,4-dione trifluoro-acetate with 500 mg (3 mmol) of 4-dimethylaminobenzoyl chloride, and after purification, 200 mg (20%) of 4-dimethylamino-N-[4'-(2,4-dioxothiazolidin-5-ylmethyl)-biphenyl-3-ylmethyl]-N-methylbenzamide, with a melting point of 100° C., are obtained.

EXAMPLE 47

N-[4'-(2,4-Dioxothiazolidin-5-ylmethyl)biphenyl-3-ylmethyl]-N-methylnicotinamide In a manner similar to that of Example 37(e), by reacting 1 g (2.2 mmol) of 5-(3'-methylaminomethyl-biphenyl-4-ylmethyl)thiazolidine-2,4-dione trifluoro-acetate with 450 mg (2.5 mmol) of nicotinoyl chloride, and after purification, 400 mg (40%) of N-[4'-(2,4-dioxothiazolidin-5-ylmethyl)biphenyl-3-ylmethyl]-N-methylnicotinamide are obtained in the form of a white solid with a melting point of 115° C.

EXAMPLE 48

3,5-Dichloro-N-[4'-(2,4-dioxothiazolidin-5-ylmethyl)biphenyl-3-ylmethyl]-N-methylbenzamide In a manner similar to that of Example 37(e), by reacting 1 g (2.2 mmol) of 5-(3'-methylaminomethyl-biphenyl-4-ylmethyl)thiazolidine-2,4-dione trifluoro-acetate with 350 µl (2.5 mmol) of 3,5-dichlorobenzoyl chloride, and after purification, 400 mg (50%) of 3,5-dichloro-N-[4'-(2,4-dioxothiazolidin-5-ylmethyl)-biphenyl-3-ylmethyl]-N-methylbenzamide are obtained in the form of a white solid with a melting point of 106° C.

EXAMPLE 49

N-[4'-(2,4-dioxothiazolidin-5-ylmethyl)biphenyl-3-ylmethyl]-N-methylthiophene-2-carboxamide In a manner similar to that of Example 37(e), by reacting 1 g (2.2 mmol) of 5-(3'-methylaminomethyl-biphenyl-4-ylmethyl)thiazolidine-2,4-dione trifluoro-acetate with 200 µl (2.5 mmol) of 2-thiophenecarboxylic acid chloride, and after purification, 500 mg (50%) of N-[4'-(2,4-dioxothiazolidin-5-ylmethyl)biphenyl-3-ylmethyl]-N-methylthiophene-2-carboxamide are obtained in the form of a white solid with a melting point of 160° C.

EXAMPLE 50

N-[4'-(2,4-dioxothiazolidin-5-ylmethyl)biphenyl-3-ylmethyl]-N-methylhexanamide

In a manner similar to that of Example 37(e), by reacting 500 mg (1.5 mmol) of 5-(3'-methylaminomethylbiphenyl-4-ylmethyl)thiazolidine-2,4-dione with 220 µl (1.6 mmol) of hexanoyl chloride, and after purification, 430 mg (66%) of N-[4'-(2,4-dioxothiazolidin-5-ylmethyl)biphenyl-3-ylmethyl]-N-methylhexanamide, with a melting point of 45° C., are obtained.

EXAMPLE 51

N-[4'-(2,4-Dioxothiazolidin-5-ylmethyl)biphenyl-3-ylmethyl]-2-methoxy-N-methylbenzamide In a manner similar to that of Example 37(e), by reacting 500 mg (1.5 mmol) of 5-(3'-methylaminomethylbiphenyl-4-ylmethyl)thiazolidine-2,4-dione with 230 μl (1.5 mmol) of 2-methoxybenzoyl chloride, and after purification, 500 mg (70%) of N-[4'-(2,4-dioxothiazolidin-5-ylmethyl)biphenyl-3-ylmethyl]-2-methoxy-N-methylbenzamide are obtained in the form of a white solid with a melting point of 96° C.

EXAMPLE 52

N-[4'-(2,4-Dioxothiazolidin-5-ylmethyl)biphenyl-3-ylmethyl]-N-methylpyridine-2-carboxamide Preparation of picolinic acid chloride:

800 μl (4.1 mmol) of dicyclohexylamine are added to 500 mg (4.1 mmol) of picolinic acid placed in 9 ml of dichloromethane, and the solution is stirred at room temperature for minutes. 300 μl (4.1 mmol) of thionyl chloride are then added and this mixture is stirred at room temperature for 2 hours. The reaction medium is diluted with ethyl ether. The precipitate is filtered off and rinsed with ethyl ether. Concentration of the filtrate gives the expected acid chloride. In a manner similar to that of Example 37(e), by reacting 500 mg (1.5 mmol) of 5-(3'-methylaminomethylbiphenyl-4-ylmethyl)thiazolidine-2,4-dione with 220 mg (1.6 mmol) of the above acid chloride, and after purification, 330 mg (50%) of N-[4'-(2,4-dioxothiazolidin-5-ylmethyl)biphenyl-3-ylmethyl]-N-methylpyridine-2-carboxamide are obtained in the form of a colorless oil.

EXAMPLE 53

N-[4'-(2,4-Dioxothiazolidin-5-ylmethyl)biphenyl-3-ylmethyl]-N-methylfuran-2-carboxamide Preparation of 2-furoyl chloride:

900 μl (4.5 mmol) of dicyclohexylamine are added to 500 mg (4.5 mmol) of 2-furoic acid placed in 5 ml of dichloromethane, and the solution is stirred at room temperature for minutes. 300 μl (4.5 mmol) of thionyl chloride are then added and this mixture is stirred at room temperature for 2 hours. The reaction medium is diluted with ethyl ether. The precipitate is filtered off and rinsed with ethyl ether. Concentration of the filtrate gives the 2-furoyl chloride.

In a manner similar to that of Example 37(e), by reacting 500 mg (1.5 mmol) of 5-(3'-methylaminomethylbiphenyl-4-ylmethyl)thiazolidine-2,4-dione with 200 mg (1.5 mmol) of 2-furoyl chloride, and after purification, 350 mg (50%) of N-[4'-(2,4-dioxo-thiazolidin-5-ylmethyl)biphenyl-3-ylmethyl]-N-methylfuran-2-carboxamide are obtained in the form of a white solid with a melting point of 150° C.

EXAMPLE 54

4-Butoxy-N-[4'-(2,4-dioxothiazolidin-5-ylmethyl)-biphenyl-3-ylmethyl]-N-methylbenzamide In a manner similar to that of Example 37(e), by reacting 500 mg (1.5 mmol) of 5-(3'-methylaminomethylbiphenyl-4-ylmethyl)thiazolidine-2,4-dione with 290 μl (1.5 mmol) of 4-butoxybenzoyl chloride, and after purification, 550 mg (83%) of 4–20 butoxy-N-[4'-(2,4-dioxothiazolidin-5-ylmethyl)biphenyl-3-ylmethyl]-N-methylbenzamide are obtained in the form of a white solid with a melting point of 116° C.

EXAMPLE 55

N-[4'-(2,4-Dioxothiazolidin-5-ylmethyl)biphenyl-3-ylmethyl]-N-methylthiophene-3-carboxamide Preparation of 3-thiophenecarboxylic acid chloride:

800 μl (3.9 mmol) of dicyclohexylamine are added to 500 mg (3.9 mmol) of 3-thiophenecarboxylic acid placed in 5 ml of dichloromethane, and the solution is stirred at room temperature for minutes. 300 μl (3.9 mmol) of thionyl chloride are then added and this mixture is stirred at room temperature for 2 hours. The reaction medium is diluted with ethyl ether. The precipitate is filtered off and rinsed with ethyl ether. Concentration of the filtrate gives the expected acid chloride.

In a manner similar to that of Example 37(e), by reacting 500 mg (1.5 mmol) of 5-(3'-methylaminomethylbiphenyl-4-ylmethyl)thiazolidine-2,4-dione with 200 mg (1.5 mmol) of 3-thiophenecarboxylic acid chloride, and after purification, 450 mg (68%) of N-[4'-(2,4-dioxothiazolidin-5-ylmethyl)biphenyl-3-ylmethyl]-N-methylthiophene-3-carboxamide are obtained in the form of a white powder with a melting point of 150° C.

EXAMPLE 56

4-{[4'-(2,4-Dioxothiazolidin-5-ylmethyl)biphenyl-3-ylmethyl]methylcarbamoyl}phenyl acetate Preparation of 4-acetoxybenzoyl chloride:

1.1 ml (5.6 mmol) of dicyclohexylamine are added to 1 g (5.6 mmol) of 4-acetoxybenzoic acid placed in 10 ml of dichloromethane, and the solution is stirred at room temperature for minutes. 400 μl (5.6 mmol) of thionyl chloride are added and this mixture is stirred at room temperature for 2 hours. The reaction medium is diluted with ethyl ether. The precipitate is filtered off and rinsed with ethyl ether. Concentration of the filtrate gives the 4-acetoxybenzoyl chloride.

In a manner similar to that of Example 37(e), by reacting 1 g (3 mmol) of 5-(3'-methylaminomethyl-biphenyl-4-ylmethyl)thiazolidine-2,4-dione with 600 mg (3 mmol) of 4-acetoxybenzoyl chloride, and after purification, 1.3 g (90%) of 4-{[4'-(2,4-dioxo-thiazolidin-5-ylmethyl)biphenyl-3-ylmethyl]-methylcarbamoyl}phenyl acetate are obtained in the form of a white powder with a melting point of 167° C.

EXAMPLE 57

N-[4'-(2,4-Dioxothiazolidin-5-ylmethyl)biphenyl-3-ylmethyl]-4-hydroxy-N-methylbenzamide 110 mg (1.3 mmol) of sodium hydrogen carbonate are added to 350 mg (6.7 mmol) of 4-{[4'-(2,4-dioxothiazolidin-5-ylmethyl)biphenyl-3-ylmethyl]methylcarbamoyl}phenyl acetate (obtained in Example 56) in 5 ml of tetrahydrofuran and 500 μl of water. The reaction medium is stirred at room temperature for 48 hours and then diluted in ethylacetate and acidified to pH 3–4 with 1N hydrochloric acid solution. The organic phase is separated out after settling of the phases has taken place, dried over sodium sulfate, filtered and evaporated. The residue obtained is purified by chromatography on a column of silica eluted with a 99/1 dichloromethane/methanol mixture. After evaporation of the solvents, 250 mg (83%) of N-[4'(2,4-dioxothiazolidin-5-ylmethyl)-biphenyl-3-ylmethyl]-4-hydroxy-N-methylbenzamide are collected in the form of a white powder with a melting point of 110° C.

EXAMPLE 58

N-[4'-(2,4-Dioxothiazolidin-5-ylmethyl)biphenyl-3-ylmethyl]-2N-dimethylbenzamide In a manner similar to that of Example 37(e), by reacting 400 mg (1.2 mmol) of 5-(3'-methylaminomethylbiphenyl-4-ylmethyl)thiazolidine-2,4-dione with 160 μl (1.2 mmol) of 2-methylbenzoyl chloride, and after purification, 500 mg (94%) of N-[4'-(2,4-dioxothiazolidin-5-ylmethyl)biphenyl-3-ylmethyl]-2N-dimethylbenzamide are obtained in the form of a white powder with a melting point of 78° C.

EXAMPLE 59

2-Butyl-N-[4'-(2,4-dioxothiazolidin-5-ylmethyl)-biphenyl-3-ylmethyl]-N-methyloctanamide Preparation of 2-butyloctanoyl chloride:

500 μl (2.5 mmol) of dicyclohexylamine are added to 500 mg (2.5 mmol) of 2-butyloctanoic acid placed in 5 ml of dichloromethane, and the solution is stirred at room temperature for minutes. 200 μl (2.5 mmol) of thionyl chloride are then added and this mixture is stirred at room temperature for 2 hours. The reaction is diluted with ethyl ether. The precipitate is filtered off and rinsed with ethyl ether. Concentration of the filtrate gives the 2-butyloctanoyl chloride.

In a manner similar to that of Example 37(e), by reacting 500 mg (1.5 mmol) of 5-(3'-methylaminomethylbiphenyl-4-ylmethyl)thiazolidine-2,4-dione with 340 mg (1.5 mmol) of 2-butyloctanoyl chloride, and after purification, 430 mg (55%) of 2-butyl-N-[4'-(2,4-dioxothiazolidin-5-ylmethyl)-biphenyl-3-ylmethyl]-N-methyloctanamide are obtained in the form of a colorless oil.

EXAMPLE 60

4-Acetylamino-N-[4'-(2,4-dioxothiazolidin-5-ylmethyl)biphenyl-3-ylmethyl]-N-methylbenzamide 320 mg (1.7 mmol) of 1-(3-dimethylamino-propyl)-3-ethylcarbodiimide hydrochloride are added portionwise, at 0° C., to a solution of 270 mg (1.5 mmol) of 4-acetamidobenzoic acid, 230 μl (1.6 mmol) of triethylamine, 230 mg (1.7 mmol) of 1-hydroxybenzotriazole and 500 mg (1.5 mmol) of 5-(3'-methylaminomethylbiphenyl-4-ylmethyl)thiazolidine-2,4-dione in 5 ml of dichloromethane. The reaction medium is stirred at from 0° C. to room temperature for 18 hours, washed with saturated sodium hydrogen carbonate solution and extracted with dichloromethane. The organic phase is separated out after settling of the phases has taken place, dried over magnesium sulfate, filtered and evaporated. The residue obtained is purified by chromatography on a column of silica eluted with a 99/1 dichloromethane/methanol mixture. After evaporation of the solvents, 600 mg (80%) of 4-acetylamino-N-[4'-(2,4-dioxothiazolidin-5-ylmethyl)biphenyl-3-ylmethyl]-N-methylbenzamide are obtained in the form of a white solid with a melting point of 207° C.

EXAMPLE 61

Hexyl N-[4'-(2,4-dioxothiazolidin-5-ylmethyl)-biphenyl-3-ylmethyl]-N-methylcarbamate A solution of 400 μl (2.5 mmol) of hexyl chloroformate in 5 ml of dichloromethane is added dropwise to a solution of 1 g (2.3 mmol) of 5-(3'-methylaminomethylbiphenyl-4-ylmethyl)-thiazolidine-2,4-dione trifluoroacetate and 1 ml (7.0 mmol) of triethylamine in 15 ml of dichloromethane. The reaction medium is stirred at room temperature for 3 hours, placed in water and extracted with ethyl acetate. The organic phase is separated out after settling of the phases has taken place, dried over magnesium sulfate, filtered and evaporated. The residue obtained is purified by chromatography on a column of silica eluted with a mixture of heptane and ethyl acetate (8/2). After evaporation of the solvents, 300 mg (30%) of hexyl N-[4'-(2,4-dioxothiazolidin-5-ylmethyl)biphenyl-3-ylmethyl]-N-methylcarbamate are obtained in the form of a colorless oil.

EXAMPLE 62

1-[4'-(2,4-Dioxothiazolidin-5-ylmethyl)biphenyl-3-yl]-3-phenylurea (a) 1-[4'-(2,4-Dioxothiazolidin-5-ylidenemethyl)-biphenyl-3-yl]-3-phenylurea 500 μl (4.6 mmol) of phenyl isocyanate are added dropwise to a solution of 1.2 g (2.3 mmol) of 5-(3'-aminobiphenyl-4-ylmethylene)thiazolidine-2,4-dione prepared as in Example 33(a) and 0.9 ml (6.4 mmol) of triethylamine in 12 ml of dichloromethane. The reaction medium is stirred at room temperature for 2 hours. It is extracted with dichloromethane and washed with water, and the organic phase is separated out after settling of the phases has taken place. The organic phase is evaporated and the residue obtained is washed with dichloromethane and dried. 950 mg (50%) of the expected product are collected.

(b) 1-[4'-(2,4-Dioxothiazolidin-5-ylmethyl)-biphenyl-3-yl]-3-phenylurea 460 mg (1.1 mmol) of 1-[4'-(2,4-dioxo-thiazolidin-5-ylidenemethyl)biphenyl-3-yl]-3-phenylurea in 20 ml of a methanol/dioxane mixture (1/1) are placed in a reactor. The reaction medium is degassed and 560 mg (1.2 equivalents by mass) of 10% palladium-on-charcoal are then added. The system is placed under 3 bar of hydrogen and heated at 50° C. for hours. The reaction medium is filtered through Celite and evaporated, and the residue obtained is purified by chromatography on a column of silica with a gradual increase in the polarity of a 9/1 mixture of heptane and ethyl acetate to a 4/6 mixture of heptane and ethylacetate. After evaporation of the solvents, 150 mg (33%) of 1-[4'-(2,4-dioxothiazolidin-5-ylmethyl)-biphenyl-3-yl]-3-phenylurea are obtained in the form of a white solid with a melting point of 185° C.

EXAMPLE 63

N-[4'-(2,4-Dioxothiazolidin-5-ylmethyl)biphenyl-3-yl]-N-methyl-2-phenylacetamide (a) (3-Bromophenyl)methylamine 10 g (58 mmol) of 3-bromoaniline and 34 ml (203 mmol) of triethylorthoformate are introduced into a three-necked flask under nitrogen. The reaction medium is stirred and refluxed for 7 hours. The excess triethyl orthoformate is evaporated off, the reaction medium is cooled to 0° C. and 100 ml of ethanol and 5 g (130 mmol) of sodium borohydride are added. The reaction medium is stirred at room temperature for 20 hours. The ethanol is evaporated off, water is added and the mixture is extracted with ethyl acetate. The organic phase is washed with saturated sodium chloride solution, dried over magnesium sulfate, filtered and evaporated. The residue obtained is purified by chromatography on a column of silica eluted with a mixture of heptane and ethyl acetate (90/10). After evaporation of the solvents, 5 g (46%) of the expected product are collected.

(b) 3'-Methylaminobiphenyl-4-carboxaldehyde

In a manner similar to that of Example 1(e), by reacting 4.3 g (23.2 mmol) of (3-bromophenyl)-methylamine with 5.2 g (34.8 mmol) of 4-formylbenzene-boronic acid, 2.9 g (60%) of the expected product are obtained.

(c) 5-(3'-Methylaminobiphenyl-4-ylmethylene)-thiazolidine-2,4,dione

In a manner similar to that of Example 1(f), starting with 2.9 g (13.7 mmol) of 3'-methylaminobiphenyl-4-carboxaldehyde and 1.6 g (13.7 mmol) of 2,4-thiazolidine dione, 3.9 g (91%) of the expected product are obtained.

(d) N-[4'-(2,4-Dioxothiazolidin-5-ylidenemethyl)-biphenyl-3-yl]-N-methyl-2-phenylacetamide In a manner similar to that of Example 37(e), by reacting 1 g (3.2 mmol) of 5-(3'-methylaminobiphenyl-4-ylmethylene)thiazolidine-2,4,dione with 470 µl (3.5 mmol) of phenylacetyl chloride, and after purification, 1.4 g (50%) of N-[4'-(2,4-dioxothiazolidin-5-ylidenemethyl)biphenyl-3-yl]-N-methyl-2-phenylacetamide are obtained.

(e) N-[4'-(2,4-Dioxothiazolidin-5-ylmethyl)-biphenyl-3-yl]-N-methyl-2-phenylacetamide In a manner similar to that of Example 62(b), starting with 660 mg (1.5 mmol) of N-[4'-(2,4-dioxothiazolidin-5-ylidenemethyl)biphenyl-3-yl]-N-methyl-2-phenylacetamide, 360 mg (54%) of N-[4'-(2,4-dioxothiazolidin-5-ylmethyl)biphenyl-3-yl]-N-methyl-2-phenylacetamide are obtained in the form of a white solid with a melting point of 138° C.

EXAMPLE 64

1-[4'-(2,4-Dioxothiazolidin-5-ylmethyl)biphenyl-3-yl]-1-methyl-3-phenylurea (a) 1-[4'-(2,4-Dioxothiazolidin-5-ylidenemethyl)-biphenyl-3-yl]-1-methyl-3-phenylurea In a manner similar to that of Example 62(a), starting with 1 g (3.2 mmol) of 5-(3'-methylamino-biphenyl-4-ylmethylene)thiazolidine-2,4-dione and 700 µl (6.4 mmol) of phenyl isocyanate, 1.2 g (86%) of the expected product are obtained.

(b) 1-[4'-(2,4-Dioxothiazolidin-5-ylmethyl)-biphenyl-3-yl]-1-methyl-3-phenylurea In a manner similar to that of Example 62(b), starting with 1.2 g (2.8 mmol) of 1-[4'-(2,4-dioxothiazolidin-5-ylidenemethyl)biphenyl-3-yl]-1-methyl-3-phenylurea, 700 mg (56%) of 1-[4'-(2,4-dioxothiazolidin-5-ylmethyl)biphenyl-3-yl]-1-methyl-3-phenylurea are obtained in the form of a white solid with a melting point of 183° C.

EXAMPLE 65

1-[4'-(2,4-Dioxothiazolidin-5-ylmethyl)biphenyl-3-yl]-3-heptyl-1-methylurea (a) 1-[4'-(2,4-Dioxothiazolidin-5-ylidene-methyl)biphenyl-3-yl]-3-heptyl-1-methylurea In a manner similar to that of Example 62(a), starting with 500 mg (1.6 mmol) of 5-(3'-methylamino-methylbiphenyl-4-ylmethylene)thiazolidine-2,4-dione and 500 µl (3.2 mmol) of heptyl isocyanate, 500 mg (71%) of the expected product are obtained.

(b) 1-[4'-(2,4-Dioxothiazolidin-5-yl-methyl)biphenyl-3-yl]-3-heptyl-1-methylurea In a manner similar to that of Example 62(b), starting with 500 mg (1.1 mmol) of 1-[4'-(2,4-dioxothiazolidin-5-ylidenemethyl)biphenyl-3-yl]-3-heptyl-1-methylurea, 300 mg (56%) of 1-[4'-(2,4-dioxothiazolidin-5-ylmethyl)biphenyl-3-yl]-3-heptyl-1-methylurea are obtained in the form of a white solid with a melting point of 55° C.

EXAMPLE 66

4-Momomethyl ester of 2-{3'-[(heptanoyl-methylamino)methyl]biphenyl-4-ylmethyl}succinic acid (a) 4-Monomethyl ester of 2-{3'-[(tert-butoxy-carbonylmethylamino) methyl]biphenyl-4-ylmethylene}-succinic acid 3.5 ml (18.5 mmol) of a 30% solution of sodium methoxide in methanol are added to 2.6 ml (15.4 mmol) of ethyl succinate in ml of methanol in a round-bottomed flask under a stream of nitrogen. The reaction medium is stirred for 15 minutes, followed by dropwise addition of 5 g (15.4 mmol) of tert-butyl(4'-formylbiphenyl-3-ylmethyl)methylcarbamate obtained in Example 37(a). The reaction medium is heated at 60° C. overnight. It is extracted with ethyl acetate and washed with water, and the organic phase is separated out after settling of the phases has taken place. The organic phase is dried over magnesium sulfate, filtered and evaporated. The residue obtained is purified by chromatography on a column of silica eluted with a 50/50 mixture of heptane and ethyl acetate. After evaporation of the solvents, 2.8 g (41%) of the expected product are collected.

(b) Methyl ethyl 2-[3'[(tert-butoxycarbonyl-methylamiono) methylbiphenyl-4-ylmethylene}succinate 1.10 ml (13 mmol) of ethyl iodide and 1.88 g (13.6 mmol) of potassium carbonate are added to 2.75 g (6.0 mmol) of 4-monomethyl ester of 2-{3'-[(tert-butyoxycarbonylmethylamino)methyl]biphenyl-4-ylmethylene}succinic acid in ml of 2-butanone. The reaction medium is refluxed for 1 hour and then filtered. The residue obtained is purified by chromatography on a column of silica eluted with a 75/25 mixture of heptane and ethyl acetate. 2.1 g (75%) of the expected product are obtained.

(c) Methyl ethyl 2-(3'-methylaminomethylbiphenyl-4-ylmethylene)succinate 2.8 ml (36.8 mmol) of trifluoroacetic acid are added to 2.1 g (4.5 mmol) of methyl ethyl 2-{3'-[(tert-butoxycarbonylmethylamiono)methyl]biphenyl-4-ylmethylene}succinate in 25 ml of dichloromethane. The reaction medium is stirred at room temperature for 18 hours, washed with saturated sodium carbonate solution and extracted with dichloromethane. The organic phase is dried over magnesium sulfate, filtered and evaporated. 1.5 g (95%) of the expected product are obtained.

(d) Methyl ethyl 2-{3'-[(heptanoylmethylamino)-methyl]biphenyl-4-ylmethylene}succinate In a manner similar to that of Example 37(e), by reacting 1.5 g (4.2 mmol) of methyl ethyl 2-(3'-methylaminomethylbiphenyl-4-ylmethylene)succinate with 740 µl (4.8 mmol) of heptanoyl chloride, and after purification, 1.8 g (89%) of the expected product are obtained.

(e) Methyl ethyl 2-{3'-[(heptanoylmethylamino)-methyl]biphenyl-4-ylmethyl}succinate In a manner similar to that of Example 1(g), starting with 1.70 g (3.5 mmol) of methyl ethyl 2-{3'-[(heptanoylmethylamino)methyl]biphenyl-4-ylmethylene}succinate and 170 mg (10% by mass) of 10% palladium-on-charcoal in 20 ml of ethyl acetate, 1.30 g (77%) of the expected product are obtained.

(f) 4-Monomethyl ester of 2-{3'-[(heptanoyl-methylamino) methyl]biphenyl-4-methyl}succinic acid 300 µl (0.7 mmol) of aqueous 2M sodium hydroxide solution are added, at 0° C., to 0.3 g (0.6 mmol) of methyl ethyl 2-{3'-[(heptanoylmethyl-amino)methyl]biphenyl-4-ylmethyl}succinate in 3 ml of methanol and 1.5 ml of tetrahydrofuran. The reaction medium is stirred at room temperature for 18 hours, acidified to Ph and extracted with ethyl acetate. The organic phase is dried over magnesium sulfate, filtered and evaporated. The residue obtained is purified by chromatography on a column of silica eluted with 99/1 dichloromethane/methanol mixture. After evaporation of the solvents, 130 mg (46%) of the 4-monomethyl ester of 2-{3'-[(heptanoylmethyl-amino)methyl]biphenyl-4-methyl}succinic acid are collected in the form of a colorless film.

EXAMPLE 67

2-{3'-[4Methyloctanoylamino)methyl]biphenyl-4-ylmethyl}succinic acid 2.4 ml (5.6 mmol) of aqueous 2N sodium hydroxide solution are added to 900 mg (1.9 mmol) of methyl ethyl 2-{3'-[(heptanoylmethylamino)methyl]-biphenyl-4-ylmethyl}succinate obtained in Example 66(e) in 9 ml of methanol and 4.5 ml of tetrahydrofuran. The reaction medium is stirred at room temperature for 36 hours and then at 50° C. for 3 hours, acidified to pH 5 and extracted with ethyl acetate. The organic phase is dried over magnesium sulfate, filtered and evaporated. The residue obtained is purified by chromatography on a column of silica eluted with a 99/1 dichloromethane/methanol mixture. After evaporation of the solvents, 300 mg (35%) of 2-{3'-[(methyloctanoyl-amino)methyl]biphenyl-4-ylmethyl}succinic acid are collected in the form of a white solid with a melting point of 57° C.

EXAMPLE 68

N-[4'-(2,5-Dioxopyrrolidin-3-ylmethyl)biphenyl-5 3-ylmethyl]-N-methylheptanamide 180 mg (3 mmol) of urea are added to 420 mg (0.97 mmol) of 2-{3'-[(methyloctanoylamino)methyl]-biphenyl-4-ylmethyl}succinic acid obtained in Example 67. The reaction medium is heated at 180° C. for 4 hours and then cooled. The residue obtained is purified by chromatography on a column of silica eluted with a 99/1 dichloromethane/methanol mixture. After evaporation of the solvents, 220 mg (55%) of N-[4'-(2,5-dioxopyrrolidin-3-ylmethyl)biphenyl-3-ylmethyl]-N-methylheptanamide are collected in the form of a colorless film.

EXAMPLE 69

3-[4'-(2,4-Dioxothiazolidin-5-ylidenemethyl)]-20 biphenyl N-phenylcarbamate (a) 3'-Hydroxybiphenyl-4-carbaldehyde In a manner similar to that of Example 1(e), starting with 20 g (115 mmol) of 3-bromophenol and 26 g (173 mmol) of 4-formylbenzene boronic acid, 15 g (65%) of the expected product are obtained.

(b) 5-(3'-Hydroxybiphenyl-4-ylmethylene)-thiazolidine-2,4-dione

In a manner similar to that of Example 1(f), starting with 15 g (75.7 mmol) of 3'-hydroxybiphenyl-4-carbaldehyde and 8.85 g (75.7 mmol) of 2,4-thiazolidine dione, 22.5 g (100%) of the expected product are obtained.

(c) 3-[4'-(2,4-Dioxothiazolidin-5-ylidene-methyl)]biphenyl N-phenylcarbamate

In a manner similar to that of Example 9(a), starting with 1.5 g (5 mmol) of 5-(3'-hydroxybiphenyl-4-ylmethylene)thiazolidine-2,4-dione and 1.1 ml (10.1 mmol) of phenyl isocyanate in 800 µl of pyridine and 10 ml of THF, 750 mg (36%) of 3-[4'-(2,4-dioxo-thiazolidin-5-ylidenemethyl)]biphenyl N-phenylcarbamate are obtained.

EXAMPLE 70

3-[4'-(2,4-Dioxothiazolidin-5-ylidenemethyl)]-biphenyl N-heptylcarbamate 1.3 ml (8.1 mmol) of heptyl isocyanate are added to 2 g (6.7 mmol) of 5-(3'-hydroxybiphenyl-4-ylmethylene)thiazolidine-2,4-dione (prepared in Example 69(b)) placed in ml of acetonitrile and 5 ml of triethylamine, and the mixture is heated at 40° C. for 5 hours. 480 mg (3.9 mmol) of 4-(dimethylamino)pyridine are then added and the mixture is refluxed for 24 hours. The reaction medium is poured into water and extracted with ether. The organic phase is evaporated. The residue obtained is washed with an 80/20 ethyl acetate/methanol mixture and dried. 1.3 g (44%) of 0.99 3-[4'-(2,4-dioxothiazolidin-5-ylidenemethyl)]biphenyl N-heptylcarbamate are collected in the form of a yellow solid with a melting point of 316° C.

EXAMPLE 71

3-[4'-(2,4-Dioxothiazolidin-5-ymethyl)]biphenyl phenylacetate (a) 3-[4'-(2,4-Dioxothiazolidin-5-ylidenemethyl)-biphenyl phenylacetate In a manner similar to that of Example 37(e), by reacting 2 g (6.7 mmol) of 5-(3'-hydroxybiphenyl-4-ylmethylene)thiazolidine-2,4-dione (prepared in Example 69(b)) with 1 ml (7.4 mmol) of phenylacetyl chloride, 2.1 g (75%) of the expected product are obtained in the form of a yellow solid.

(b) 3-[4'-(2,4-Dioxothiazolidin-5-ylmethyl)-biphenyl phenylacetate

In a manner similar to that of Example 1(g), starting with 2.1 g (5 mmol) of 3-[4'-(2,4-dioxothiazolidin-5-ylidenemethyl)]biphenyl phenylacetate in 40 ml of a dioxane/methanol mixture (50/50), and after purification by chromatography on a column of silica eluted with a heptane/ethyl acetate mixture (8/2), 810 mg (38%) of 3-[4'-(2,4-dioxothiazolidin-5-ylmethyl)biphenyl phenylacetate are obtained in the form of a yellow solid with a melting point of 147° C.

EXAMPLE 72

3-[4'-(2,4-Dioxothiazolidin-5-ylmethyl)biphenyl nonanoate (a) 5-(3'-Hydroxybiphenyl-4-ylmethyl)-thiazolidine-2,4-dione In a manner similar to that of Example 1(g), starting with 3 g (10.1 mmol) of 5-(3'-hydroxybiphenyl-4-ylmethylene)

thiazolidine-2,4-dione in a dioxane/methanol mixture (50/50), and after purification by chromatography on a column of silica eluted with a heptane/ethyl acetate mixture (7/3), 800 mg (27%) of the expected product are obtained.

(b) 3-[4'-(2,4-Dioxothiazolidin-5-ylmethyl)]-biphenyl nonanoate

In a manner similar to that of Example 37(e), by reacting 600 mg (2 mmol) of 5-(3'-hydroxybiphenyl-4-ylmethyl) thiazolidine-2,4-dione with 400 µl (2.2 mmol) of nonanoyl chloride and 50 mg (0.4 mmol) of 4-(dimethylamino) pyridine, 780 mg (89%) of 3-[4'-(2,4-dioxothiazolidin-5-ylmethyl)biphenyl nonanoate are obtained in the form of a white solid with a melting point of 70° C.

EXAMPLE 73

3-[4'-(2,4-Dioxothiazolidin-5-ylmethyl)]biphenylN-heptylcarbamate

In a manner similar to that of Example 1(g), starting with 950 mg (2.2 mmol) of 3-[4'-(2,4-dioxothiazolidin-5-ylidenemethyl)]biphenyl N-heptylcarbamate (obtained in Example 70) in a dioxane/methanol mixture (50/50) under 3 atm of hydrogen, 130 mg (13%) of 3-[4'-(2,4-dioxothiazolidin-5-ylmethyl)]biphenyl N-heptylcarbamate are obtained in the form of a white solid with a melting point of 315° C.

EXAMPLE 74

3-[4'-(2,4-Dioxothiazolidin-5-ylmethyl]biphenyl N-phenylcarbamate

In a manner similar to that of Example 1(g), starting with 740 mg (1.78 mmol) of 3-[4'-(2,4-dioxothiazolidin-5-ylidenemethyl]biphenyl N-phenylcarbamate (obtained in Example 69), in 25 ml of dioxane under 3 atm of hydrogen, 310 mg (42%) of 3-[4'-(2,4-dioxothiazolidin-5-ylmethyl] biphenyl N-phenylcarbamate are obtained in the form of a white solid with a melting point of 142° C.

EXAMPLE 75

N-[6-Benzyloxy-4'-(2,4-dioxothiazolidin-5-ylidene-methyl)biphenyl-3-ylmethyl]-N-methyloctanamide (a) 4-Benzyloxy-3-bromobenzaldehydeg (124 mmol) of 3-bromo-4-hydroxy-benzaldehyde, 250 ml of 2-butanone, 14.8 ml (124 mmol) of benzyl bromide and 42.8 g (310 mmol) of potassium carbonate are introduced into a round-bottomed flask under a stream of nitrogen. The reaction medium is refluxed for 4 hours, filtered and evaporated. The residue is taken up in diisopropyl ether and then filtered and dried. 28 g (77%) of the expected product are obtained in the form of a beige-colored powder with a melting point of 93° C.

(b) N-(4-Benzyloxy-3-bromo benzyl)-N-methylamine 25 g (86 mmol) of 4-benzyloxy-3-bromo-benzaldehyde, 500 ml of methanol, 29 g (430 mmol) of methylamine hydrochloride and 8 g (127 mmol) of sodium cyanoborohydride are introduced into a round-bottomed flask under a stream of nitrogen. The reaction medium is stirred for 48 hours at room temperature. The methanol is evaporated off. The residue is taken up in ethyl acetate and water and then acidified. After separation of the phases once settling has taken place, the aqueous phase is returned to basic pH with sodium hydroxide and extracted with ethyl acetate. The organic phase is dried over magnesium sulfate, filtered and then evaporated. The residue is purified by chromatography on a column of silica eluted with a dichloromethane/ethanol mixture (9/1). 9.9 g (38%) of the expected product are obtained in the form of a colorless oil.

(c) N-(4-Benzyloxy-3-bromo benzyl)-N-methyl-octanamide

In a manner similar to that of Example 37(e), by reacting 9.9 g (32 mmol) of N-(4-benzyloxy-3-bromo benzyl)-N-methylamine with 5.3 g (32 mmol) of octanoyl chloride in 90 ml of dichloromethane, 13.6 g (97%) of the expected product are obtained in the form of a colorless oil.

(d) N-(6-Benzyloxy-4'-formylbiphenyl-3-ylmethyl)-N-methyloctanamide

In a manner similar to that of Example 1(e), by reacting 13.6 g (31 mmol) of N-(4-benzyloxy-3-bromo benzyl)-N-methyloctanamide and 6.1 g (40 mmol) of 4-formylbenzene boronic acid, 11.5 g (69%) of the expected product are obtained in the form of a yellow oil.

(e) N-[6-Benzyloxy-4'-(2,4-dioxothiazolidin-5-ylidenemethyl)biphenyl-3-ylmethyl]-N-methyloctanamide In a manner similar to that of Example 1(f), by reacting 11.5 g (22 mmol) of N-(6-benzyloxy-4'-formylbiphenyl-3-ylmethyl)-N-methyloctanamide and 2.5 g (22 mmol) of 2,4-thiazolidine dione, the expected product is obtained in the form of a pale yellow powder with a melting point of 162° C.

EXAMPLE 76

N-[4'-(2,4-Dioxothiazolidin-5-ylmethyl)-6-hydroxybiphenyl-3-ylmethyl]-N-methyloctanamide (a) N-[6-Benzyloxy-4'-(2,4-dioxothiazolidin-5-ylmethyl) biphenyl-3-ylmethyl]-N-methyloctanamide In a manner similar to that of Example 1(g), starting with 1 g (1.8 mmol) of N-[6-benzyloxy-4'-(2,4-dioxothiazolidin-5-ylidenemethyl)biphenyl-3-ylmethyl]-N-methyloctanamide (obtained in Example 75) in ml of dioxane and 1 ml of triethylamine under 3 atm of hydrogen, 270 mg (27%) of the expected product are obtained in the form of a yellow oil.

(b) N-[4'-(2,4-Dioxothiazolidin-5-ylmethyl)-6-hydroxybiphenyl-3-ylmethyl]-N-methyloctanamide 250 mg (0.45 mmol) of N-[6-benzyloxy-4'-(2,4-dioxothiazolidin-5-ylmethyl)biphenyl-3-ylmethyl]-N-methyloctanamide, 4 ml of acetonitrile and 130 mg (0.65 mmol) of iodotrimethylsilane are introduced into a round-bottomed flask under a stream of nitrogen. The reaction medium is heated, at 50° C. for 3 hours. At room temperature, 450 µl of 1N hydrochloric acid and 450 µl of tetrabutylammonium fluoride are added. The medium is then diluted with ethyl acetate and washed with sodium thiosulfate solution. After separation of the phases once settling has taken place, the organic phase is dried over magnesium sulfate, filtered and evaporated. The residue obtained is purified by chromatography on a column of silica eluted with an ethyl acetate/heptane mixture (6/4). 150 mg (72%) of N-[4'-(2,4-dioxo-thiazolidin-5-ylmethyl)-6-hydroxybiphenyl-3-ylmethyl]-N-methyloctanamide are obtained in the form of a yellowish foam.

EXAMPLE 77

N-[4-Benzyloxy-4'-(2,4-dioxothiazolidin-5-ylidenemethyl)biphenyl-3-ylmethyl-N-methyloctanamide (a) 2-Benzyloxy-5-bromobenzaldehyde In a manner similar to that of Example 75(a), by reacting g (150 mmol) of 5-bromo-2-hydroxy-benzaldehyde and 17.8 ml (150 mmol) of benzyl bromide in 300 ml of acetone, and after purification by chromatography on a column of silica eluted with a heptane/ethyl acetate mixture (8/2), 22.8 g (52%) of the expected product are obtained in the form of a yellow solid.

(b) N-(2-Benzyloxy-5-bromo benzyl)-N-methylamine

In a manner similar to that of Example 75(b), by reacting 22.5 g (77 mmol) of 2-benzyloxy-5-bromobenzaldehyde, 26.1 g (386 mmol) of methylamine hydrochloride and 7.3 g (116 mmol) of sodium cyanoborohydride, and after purification by chromatography on a column of silica eluted with a dichloromethane/methanol mixture (9/1) and 0.5% isopropylamine, 12.2 g (51%) of the expected product are obtained in the form of a pale yellow oil.

(c) N-(2-Benzyloxy-5-bromo benzyl)-N-methyl-octanamide

In a manner similar to that of Example 37(e), by reacting 6 g (19.6 mmol) of N-(2-benzyloxy-5-bromo benzyl)-N-methylamine with 3.4 ml (19.6 mmol) of octanoyl chloride, and after purification by chromatography on a column of silica eluted with a heptane/ethyl acetate mixture (8/2), 8 g (95%) of the expected product are obtained in the form of a colorless oil.

(d) N-(4-Benzyloxy-4'-formylbiphenyl-3-ylmethyl)-N-methyloctanamide

In a manner similar to that of Example 1(e), by reacting 8 g (18.5 mmol) of N-(2-benzyloxy-5-bromo benzyl)-N-methyloctanamide and 3.6 g (24 mmol) of 4-formylbenzene boronic acid, and after purification by chromatography on a column of silica eluted with a heptane/ethyl acetate mixture (8/2), 5.8 g (69%) of the expected product are obtained in the form of a white solid.

(e) N-[4-Benzyloxy-4'-(2,4-dioxothiazolidin-5-ylidenemethyl)biphenyl-3-ylmethyl]-N-methyloctanamide In a manner similar to that of Example 1(f), by reacting 5.8 g (13 mmol) of N-(4-benzyloxy-4'-formylbiphenyl-3-ylmethyl)-N-methyloctanamide and 1.5 g (13 mmol) of 2,4-thiazolidenedione, 5.2 g (74%) of N-[4-benzyloxy-4'-(2,4-dioxothiazolidin-5-ylidene-methyl)biphenyl-3-ylmethyl]-N-methyloctanamide are obtained in the form of a bright yellow powder with a melting point of 158° C.

EXAMPLE 78

N-[4"-(2,4-Dioxothiazolidin-5-ylmethyl)-[1,1';3',1"]terphenyl-5'-ylmethyl]-N-methyloctanamide (a) 3-Bromo-5-iodo-N-methylbenzamide 37.5 g (115 mmol) of 3-bromo-5-iodobenzoic acid in 300 ml of dimethylformamide are introduced into a round-bottomed flask under a stream of nitrogen. 17.6 ml (127 mmol) of triethylamine, 17 g (126 mmol) of 1-hydroxybenzotriazole and 7.75 g (115 mmol) of methylamine hydrochloride are added. The reaction medium is cooled to 0° C., followed by portionwise addition of 24.2 g (126 mmol) of 1-[3-(dimethyl-amino)propyl]-3-ethylcarbodiimide hydrochloride. The medium is allowed to warm to room temperature and is stirred for 18 hours. It is then poured into water and the precipitate obtained is filtered off, washed with heptane and then dried. 37.3 g (96%) of the expected product are obtained in the form of a beige-colored powder with a melting point of 205° C.

(b) 5-Bromo-N-methyl-3-biphenylcarboxamide

In a manner similar to that of Example 1(e), by reacting 4.9 g (14 mmol) of 3-bromo-5-iodo-N-methyl-benzamide and 1.93 g (15.8 mmol) of phenylboronic acid, and after purification by chromatography on a column of silica eluted with a heptane/ethyl acetate mixture(8/2), 2.1 g (50%) of the expected product are obtained in the form of a white solid with a melting point of 132° C.

(c) 4"-Formyl-N-methyl[1,1';3',1"]terphenyl-5'-carboxamide

In a manner similar to that of Example 1(e), by reacting 2 g (7 mmol) of 5-bromo-N-methyl-3-biphenylcarboxamide and 1.4 g (9.3 mmol) of 4-formylbenzene boronic acid, and after purification by recrystallization from acetonitrile, 1.4 g (63%) of the expected product are obtained in the form of a beige-colored solid.

(d) (5'-Methylaminomethyl[1,1';3',1"]terphenyl-4"-yl)methanol 1 g (26 mmol) of lithium aluminum hydride in 20 ml of tetrahydrofuran are introduced into a round-bottomed flask under a stream of nitrogen. The medium is cooled to 0° C. and a solution of 1.4 g (4.4 mmol) of 4"-formyl-N-methyl [1,1';3',1"]terphenyl-5'-carboxamide in 30 ml of tetrahydrofuran is added dropwise. The reaction medium is refluxed for 48 hours. It is then allowed to cool to room temperature and aqueous sodium sulfate solution is added dropwise. After 30 minutes, the medium is acidified to pH 5 and extracted with ethyl acetate. The organic phase is dried over magnesium sulfate, filtered and then evaporated. The residue is purified by chromatography on a column of silica eluted with a dichloromethane/ethanol mixture (9/1) and 660 mg (49%) of the expected product are obtained in the form of a white solid.

(e) 5'-Methylaminomethyl [1,1'; 3',1"]terphenyl-4"-carbaldehyde 660 mg (2.2 mmol) of (5'-methylaminomethyl[1,1';3',1"]terphenyl-4"-yl)methanol and 1.9 g (22 mmol) of manganese dioxide in 30 ml of dichloromethane are introduced into a round-bottomed flask. The reaction medium is stirred for 24 hours at room temperature. It is then filtered through Celite and evaporated. 410 mg (62%) of the expected product are obtained in the form of a pale yellow solid. 10

(f) 5-(5'-Methylaminomethyl[1,1';3',1"]terphenyl-4"-ylmethylene)thiazolidine-2,4-dione In a manner similar to that of Example 1(f), by reacting 400 mg (1.3 mmol) of 5'-methylamino-methyl[1,1';3',1"]terphenyl-4"-carbaldehyde and 160 mg (1.3 mmol) of 2,4-thiazolidine dione, 530 mg (100%) of the expected product are obtained in the form of an orange powder.

(g) N-[4"-(2,4-dioxothiazolidin-5-ylidene-methyl)[1,1';3',1"]terphenyl-5'-ylmethyl]-N-methyl-octanamide In a manner similar to that of Example 37(e), by reacting 530 mg (1.3 mmol) of 5-(5'-methylamino-methyl[1,1';3',1"]terphenyl-4"-ylmethylene)-thiazolidine-2,4-dione with 230 μl (1.3 mmol) of octanoyl chloride, and after purification by chromatography on a column of silica eluted with a dichloromethane/methanol mixture (95/5), 390 mg (56%) of the expected product are obtained in the form of an orange oil.

(h) N-[4"-(2,4-dioxothiazolidin-5-ylmethyl)-[1,1';3',1"]terphenyl-5'-ylmethyl]-N-methyloctanamide In a manner similar to that of Example 1(g), starting with 370 mg (7 mmol) of N-[4"-(2,4-dioxothiazolidin-5-ylidenemethyl)[1,1';3',1"]terphenyl-5'-ylmethyl]-N-methyl-octanamide in 5 ml of dioxane and under 3 atm of hydrogen, and after purification by chromatography on a column of silica eluted with a heptane/ethyl acetate mixture (6/4), 170 mg (47%) of N-[4"-(2,4-dioxo-thiazolidin-5-ylmethyl)[1,1';3',1"]terphenyl-5'-yl-methyl]-N-methyloctanamide are obtained in the form of a pale yellow foam.

EXAMPLE 79

N-[4'-(2,4-Dioxothiazolidin-5-ylmethyl)-2'-methylbiphenyl-3-ylmethyl]-N-methyloctanamide (a) tert-Butyl (3-bromo benzyl)carbamate In a manner similar to that of Example 1(a), starting with 50 g (220 mmol) of 3-bromobenzylamine hydrochloride, 65.1 g (100%) of the expected product are obtained in the form of a pale brown solid.

(b) tert-Butyl (3-bromo benzyl)-N-methylcarbamate

In a manner similar to that of Example 1(b), starting with 85 g (297 mmol) of tert-butyl (3-bromo benzyl)carbamate, 92.5 g (100%) of the expected product are obtained.

(c) tert-Butyl (4'-formyl-2'-methylbiphenyl-3-ylmethyl)-N-methylcarbamate

In a manner similar to that of Example 1(e), by reacting 6.1 g (20.3 mmol) of tert-butyl (3-bromo benzyl)-N-methylcarbamate with 4.3 g (26.2 mmol) of 2-methyl-4-formylbenzene boronic acid, and after purification by chromatography on a column of silica eluted with a heptane/ethyl acetate mixture (8/2), 4 g (58%) of the expected product are obtained in the form of an orange oil.

(d) tert-Butyl [4'-(2,4-dioxothiazolidin-5-ylidenemethyl)-2'-methylbiphenyl-3-ylmethyl]-N-methylcarbamate In a manner similar to that of Example 1(f), by reacting 3.95 g (11.6 mmol) of tert-butyl (4'-formyl-2'-methylbiphenyl-3-ylmethyl)-N-methylcarbamate with 1.4 g (11.6 mmol) of 2,4-thiazolidine dione, and after purification by chromatography on a column of silica eluted with a heptane/ethyl acetate mixture (8/2), 3 g (59%) of the expected product are obtained in the form of a yellow solid with a melting point of 156° C.

(e) tert-Butyl [4'-(2,4-dioxothiazolidin-5-ylmethyl)-2'-methylbiphenyl-3-ylmethyl]-N-methylcarbamate.

In a manner similar to that of Example 1(g), starting with 1.5 g (3.4 mmol) of tert-butyl [4'-(2,4-dioxothiazolidin-5-ylidenemethyl)-2'-methylbiphenyl-3-ylmethyl]-N-methylcarbamate, and after purification by chromatography on a column of silica eluted with a heptane/ethyl acetate mixture (8/2), 1.2 g (82%) of the expected product are obtained in the form of a yellowish oil.

(f) 5-(2-Methyl-3'-methylaminomethylbiphenyl-4-ylmethyl)thiazolidine-2,4-dione

In a manner similar to that of Example 1(c), starting with 1.2 g (2.7 mmol) of tert-butyl [4'-(2,4-dioxothiazolidin-5-ylmethyl)-2'-methylbiphenyl-3-ylmethyl]-N-methylcarbamate, 720 mg (78%) of the expected product are obtained in the form of a white solid.

(g) N-[4'-(2,4-Dioxothiazolidin-5-ylmethyl)-2'-methylbiphenyl-3-ylmethyl]-N-methyloctanamide In a manner similar to that of Example 37(e), by reacting 300 mg (0.88 mol) of 5-(2-methyl-3'-methyl-aminomethylbiphenyl-4-ylmethyl)thiazolidine-2,4-dione with 140 mg (0.88 mmol) of octanoyl chloride, and after purification by chromatography on a column of silica eluted with a heptane/ethyl acetate mixture (6/4), 250 mg (63%) of N-[4'-(2,4-dioxothiazolidin-5-ylmethyl)-2'-methylbiphenyl-3-ylmethyl]-N-methyloctanamide are obtained in the form of a white solid with a melting point of 130° C.

EXAMPLE 80

N-[4'-(2,4-Dioxothiazolidin-5-ylmethyl)-3'-methylbiphenyl-3-ylmethyl]-N-methyloctanamide (a) tert-Butyl (4'-formyl-3'-methylbiphenyl-3-ylmethyl)-N-methylcarbamate In a manner similar to that of Example 1(e), by reacting 1.1 g (3.5 mmol) of tert-butyl (3-bromo-benzyl)-N-methylcarbamate obtained in Example 79(b) with 750 mg (4.6 mmol) of 3-methyl-4-formylbenzene-boronic acid, and after purification by chromatography on a column of silica eluted with a heptane/ethyl acetate mixture (7/3), 1 g (87%) of the expected product is obtained in the form of a yellow oil.

(b) tert-Butyl [4'-(2,4-dioxothiazolidin-5-ylidenemethyl)-3'-methylbiphenyl-3-ylmethyl]-N-methylcarbamate In a manner similar to that of Example 1(f) by reacting 1 g (2.9 mmol) of tert-butyl (4'-formyl-3'-methylbiphenyl-3-ylmethyl)-N-methylcarbamate with 350 mg (2.9 mmol) of 2,4-thiazolidine dione, and after purification by chromatography on a column of silica eluted with a heptane/ethyl acetate mixture (6/4), 740 mg (57%) of the expected product are obtained in the form of a yellow oil (c) tert-Butyl [4'-(2,4-dioxothiazolidin-5-ylmethyl)-3'-methylbiphenyl-3-ylmethyl]-N-methylcarbamate.

In a manner similar to that of Example 1(g), starting with 740 mg (1.7 mmol) of tert-butyl [4'-(2,4-dioxothiazolidin-5-ylidenemethyl)-3'-methylbiphenyl-3-ylmethyl]-N-methylcarbamate, 720 mg (97%) of the expected product are obtained in the form of a yellow oil.

(d) 5-(3-Methyl-3'-methylaminomethylbiphenyl-4-ylmethyl)thiazolidine-2,4-dione

In a manner similar to that of Example 1(c), starting with 720 mg (1.6 mmol) of tert-butyl [4'-(2,4-dioxothiazolidin-5-ylmethyl)-3'-methylbiphenyl-3-ylmethyl]-N-methylcarbamate, 320 mg (58%) of the expected product are obtained in the form of a white powder with a melting point of 135° C.

(e) N-[4'-(2,4-Dioxothiazolidin-5-ylmethyl)-3'-methylbiphenyl-3-ylmethyl]-N-methyloctanamide In a manner similar to that of Example 37(e), by reacting 310 mg (0.9 mmol) of 5-(3-methyl-3'-methyl-aminomethylbiphenyl-4-ylmethyl)thiazolidine-2,4-dione with 160 mg (0.9 mmol) of octanoyl chloride, and after purification by chromatography on a column of silica eluted with a heptane/ethyl acetate mixture (6/4), 230 mg (55%) of N-[4'-(2,4-dioxothiazolidin-5-ylmethyl)-3'-methylbiphenyl-3-ylmethyl]-N-methyl-octanamide are obtained in the form of a yellowish oil.

EXAMPLE 81

(S)-2-Ethoxy-3-{3'-[(methyloctanoylamino)methyl]-biphenyl-4-yl}propionic acid (a) tert-Butyl (4'-formylbiphenyl-3-ylmethyl)-N-methylcarbamate In a manner similar to that of Example 1(e), by reacting 38 g (127 mmol) of tert-butyl (3-bromo benzyl)-N- methylcarbamate obtained in Example 79(b) with 25.6 g (170 mmol) of 4-formylbenzene boronic acid, and after purification by chromatography on a column of silica eluted with a heptane/ethyl acetate mixture (9/1), 20 g (57%) of the expected product are obtained.

(b) Ethoxyacetyl Chloride (240 mmol) of ethoxyacetic acid in 300 ml of dichloromethane are introduced into a round-bottomed flask under a stream of nitrogen. 47.6 ml (239 mmol) of dicyclohexylamine are added. The medium is stirred for 1 hour at room temperature. 19.2 ml (265 mmol) of thionyl chloride are then added and the mixture is stirred for 3 hours. Ethyl ether is added to the reaction medium and the precipitate formed is filtered off and rinsed with ether. After evaporation of the filtrate, 29 g (100%) of the expected product are obtained in the form of a brown liquid.

(c) 3-(2-Ethoxyethanoyl)-4-benzyloxazolidin-2-one 36.7 g (207 mmol) of (S)-4-benzyloxazolidin-2-one in 800 ml of THF are introduced into a round-bottomed flask under a stream of nitrogen. The reaction medium is cooled to −78° C. and 83 ml (207 mmol) of 2.5M n-butyllithium hexane are added dropwise. 30 minutes later, 25.4 g (207 mmol) of ethoxyacetyl chloride obtained in Example 81(b) are added, at −78° C. The reaction medium is stirred for 24 hours and then poured into saturated aqueous sodium chloride solution and extracted with ethyl acetate. The organic phase is dried over magnesium sulfate, filtered and evaporated. After purification by chromatography on a column of silica eluted with a heptane/ethyl acetate mixture (6/4), 30.6 g (56%) of the expected product are obtained in the form of an orange-colored oil.

(d) Methyl (2S,3R)-3-({3'-[(tert-butoxycarbonylmethylamino) methyl]biphenyl-4-yl}-2-ethoxy-3-hydroxypriopionate In a manner similar to that of Example 13(a), by reacting 23.5 g (69 mmol) of tert-butyl (4'-formyl-biphenyl-3-ylmethyl)-N-methylcarbamate prepared in Example 81(a) with 21.9 g (83 mmol) of 3-(2-ethoxy-ethanoyl)-4-benzyloxazolidin-2-one, and after purification by chromatography on a column of silica eluted with a heptane/ethyl acetate mixture (7/3), 21 g (51%) of the expected product are obtained.

(e) Methyl (2S,3R)-2-ethoxy-3-hydroxy-3-(3'-methylaminomethylbiphenyl-4-yl)propionate 21 g (47.3 mmol) of methyl (2S,3R)-3-{3'-[(tert-butoxycarbonylmethylamino)methyl]biphenyl-4-yl}-2-ethoxy-3-hydroxypriopionate and 8.76 ml (54.9 mmol) of triethylsilane in 300 ml of trifluoroacetic acid are introduced into a round-bottomed flask under a stream of nitrogen. The reaction medium is stirred at room temperature for 4 hours. Ethyl acetate is then added and the mixture is neutralized with sodium hydroxide. The organic phase is washed with saturated aqueous sodium chloride solution, dried over magnesium sulfate, filtered and evaporated. 19.6 g (100%) of crude deprotected but still hydroxylated product are obtained.

(f) Methyl (S)-2-ethoxy-3-(3'-methylaminomethyl-biphenyl-4-yl)propionate 19.6 g of the crude product obtained in Example 81(e) are dissolved in 200 ml of trifluoroacetic acid and 41.7 ml (297 mmol) of triethylamine are added. The reaction medium is stirred at room temperature for 48 h and then extracted with ethyl acetate. The organic phase is separated out after settling of the phases has taken place, washed with sodium hydroxide solution and then with saturated aqueous sodium chloride solution, dried over magnesium sulfate, filtered and evaporated. The residue obtained is purified by chromatography on a column of silica eluted with a dichloromethane/methanol mixture (95/5).1.6 g (10%) of the expected product are obtained.

(g) Methyl (S)-2-ethoxy-3-{3'-[(methyloctanoyl-amino) methyl]biphenyl-4-yl}propionate In a manner similar to that of Example 37(e), by reacting 500 mg (1.5 mmol) of methyl (S)-2-ethoxy-3-(3'-methylaminomethylbiphenyl-4-yl)propionate with 550 µl (3.18 mmol) of octanoyl chloride, and after purification by chromatography on a column of silica eluted with a heptane/ ethyl acetate mixture (70/30), 200 mg (29%) of the expected product are obtained.

(h) (S)-2-Ethoxy-3-{3'-[(methyloctanoyl-amino) methyl]biphenyl-4-yl}propionic acid In a manner similar to that of Example 13(c), by reacting 180 mg (0.4 mmol) of methyl (S)-2-ethoxy-3-{3'-[(methyloctanoylamino)methyl]biphenyl-4-yl}propionate with 17 mg (0.4 mmol) of lithium hydroxide monohydrate, and after purification by chromatography on a column of silica eluted with a heptane/ethyl acetate mixture (50/50), 130 mg (74%) of the expected product are obtained in the form of a colorless oil.

EXAMPLE 82

1-[4'-(2,4-Dioxothiazolidin-5-ylmethyl)biphenyl-3-yl]-1-ethyl-3-phenylurea (a) (3-Bromophenyl)ethylamine 5 g (29.1 mmol) of 3-bromoaniline in 500 ml of ether are introduced into a round-bottomed flask under a stream of nitrogen. 4.5 ml (32 mmol) of triethylamine and 15.2 ml (117 mmol) of diethyl sulfate are added. The medium is refluxed for 24 hours and then left for 8 days at room temperature. It is then poured into water and extracted with ether. The organic phase is washed with saturated aqueous sodium chloride solution and is then dried over magnesium sulfate, filtered and evaporated. The residue is purified by chromatography on a column of silica eluted with a heptane/ ethyl acetate mixture (95/5) and 2.5 g (43%) of the expected product are obtained.

(b) 3'-Ethylaminobiphenyl-4-carbaldehyde

In a manner similar to that of Example 1(e), by reacting 1.25 g (6.25 mmol) of (3-bromophenyl)ethyl-amine with 1.4 g (9.4 mmol) of 4-formylbenzene boronic acid, and after purification by chromatography on a column of silica with a heptane/ethyl acetate fluent mixture (75/25), 1 g (71%) of the expected product is obtained in the form of a yellow solid.

(c) 5-(3'-Ethylaminobiphenyl-4-ylmethylene)-thiazolidine-2,4-dione

In a manner similar to that of Example 1(f), by reacting 900 mg (4 mmol) of 3'-ethylaminobiphenyl-4-carbaldehyde with 470 mg (4 mmol) of 2,4-thiazolidine dione, 1 g (77%) of the expected product are obtained in the form of an orange solid.

(d) 1-[4'-(2,4-Dioxothiazolidin-5-ylidene-methyl)biphenyl-3-yl]-1-ethyl-3-phenylurea In a manner similar to that of Example 9(a), by reacting 500 mg (1.54 mmol) of 5-(3'-ethylamino-biphenyl-4-ylmethylene)thiazolidine-2,4-dione with 340 µl (3.1 mmol) of phenyl isocyanate, 650 mg (95%) of the expected product are obtained in the form of a yellow solid.

(e) 1-[4'-(2,4-Dioxothiazolidin-5-ylmethyl)bi-phenyl-3-yl]-1-ethyl-3-phenylurea

In a manner similar to that of Example 1(g), starting with 650 mg (1.4 mmol) of 1-[4'-(2,4-dioxothiazolidin-5-ylidenemethyl)biphenyl-3-yl]-1-ethyl-3-phenylurea, and after purification by chromatography on a column of silica eluted with a heptane/ethyl acetate mixture (70/30), 400 mg (61%) of 1-[4'-(2,4-dioxothiazolidin-5-ylmethyl)biphenyl-3-yl]-1-ethyl-3-phenylurea are obtained in the form of a white powder with a melting point of 186° C.

EXAMPLE 83

The agonist activity of the compounds according to the invention towards PPARγ receptors may be evaluated by binding tests and transactivation tests. The results obtained for the compounds according to the invention are collated in the table below:

TABLE 1

| Compounds | % of activation of PPARα | % of activation of PPARγ | Binding of PPAR-γ Kd in nM |
|---|---|---|---|
| Reference 1: Wy 14643 | 100* | n.a. | n.a. |
| Reference 2: SB 219994 | n.a. | 100 | 0.5 |
| Reference 3: BRL 49,653 | 3 | 83 | 23 |
| Example 1 | 8.2 | 102.2 | 55 |
| Example 2 | 8.2 | 42.9 | 263 |
| Example 10 | 0 | 22.1 | 800 |
| Example 11 | 2.4 | 74.5 | 289 |
| Example 12 | 0 | 60.4 | 7 |
| Example 13 | 0 | 70.2 | 24 |
| Example 21 | 14.9 | 90 | 190 |
| Example 22 | 7.5 | 95.3 | 76.6 |
| Example 24 | 8.7 | 95 | 72.3 |
| Example 26 | 2.1 | 88.6 | N.T. |
| Example 28 | 1.1 | 79.8 | N.T. |
| Example 30 | 8.9 | 80.3 | N.T. |
| Example 32 | 0 | 74.9 | N.T. |
| Example 34 | 17.6 | 102.5 | 2 |
| Example 35 | 11 | 56 | N.T. | n.a. means not active
N.T. means not tested.
* . . . % of activation at a concentration of 1 μM These results show the affinity of the compounds for PPAR-γ and their transactivation activity. These results more particularly show the specificity of the activation of the compounds of the invention for the PPAR-γ sub-type, compared with the activation of the compounds for the PPAR-α sub-type.

EXAMPLE 84

Various concrete formulations based on the compounds according to the invention are illustrated in this example.

A-ORAL ROUTE:

(a) 0.2 g tablet:

| | |
|---|---|
| Compound 1 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampules:

| | | |
|---|---|---|
| Compound 5 | | 0.001 g |
| Glycerol | | 0.500 g |
| 70% Sorbitol | | 0.500 g |
| Sodium saccharinate | | 0.010 g |
| Methyl para-hydroxybenzoate | | 0.040 g |
| Flavoring | qs | |
| Purified water | qs | 5 ml |

(c) 0.8 g tablet:

| | |
|---|---|
| Compound 2 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable suspension in 10 ml ampules:

| | | |
|---|---|---|
| Compound 4 | | 0.200 g |
| Glycerol | | 1.000 g |
| 70% Sorbitol | | 1.000 g |
| Sodium saccharinate | | 0.010 g |
| Methyl para-hydroxybenzoate | | 0.080 g |
| Flavoring | qs | |
| Purified water | qs | 10 ml |

B-TOPICAL ROUTE:

(a) Ointment:

| | |
|---|---|
| Compound 6 | 0.020 g |
| Isopropyl myristate | 81.700 g |
| Liquid petroleum jelly fluid | 9.100 g |
| Silica ("Aerosil 200" sold by Degussa) | 9.180 g |

(b) Ointment:

| | | |
|---|---|---|
| Compound 2 | | 0.300 g |
| White petroleum jelly codex | qs | 100 g |

(c) Nonionic water-in-oil cream:

| | | |
|---|---|---|
| Compound 1 | | 0.100 g |
| Mixture of emulsifying lanolin alcohols, waxes and oils ("Anhydrous Eucerin" sold by BDF) | | 39.900 g |
| Methyl para-hydroxybenzoate | | 0.075 g |
| Propyl para-hydroxybenzoate | | 0.075 g |
| Sterile demineralized water | qs | 100 g |

(d) Lotion 5:

| Compound 3 | 0.100 g |
|---|---|
| Polyethylene glycol (PEG 400) | 69.900 g |
| 95% Ethanol | 30.000 g |

(e) Hydrophobic ointment:

| Compound 5 | | 0.300 g |
|---|---|---|
| Isopropyl myristate | | 36.400 g |
| Silicone oil ("Rhodorsil 47 V 300") sold by Rhone-Poulenc | | 36.400 g |
| Beeswax | | 13.600 g |
| Silicone oil ("Abil 300,000 CST" sold by Goldschmidt) | qs | 100 g |

(f) Nonionic oil-in-water cream:

| Compound 2 | | 1.000 g |
|---|---|---|
| Cetyl alcohol | | 4.000 g |
| Glyceryl monostearate | | 2.500 g |
| PEG-50 stearate | | 2.500 g |
| Karite butter | | 9.200 g |
| Propylene glycol | | 2.000 g |
| Methyl para-hydroxybenzoate | | 0.075 g |
| Propyl para-hydroxybenzoate | | 0.075 g |
| Sterile demineralized water | qs | 100 g |

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the following structural formula (I):

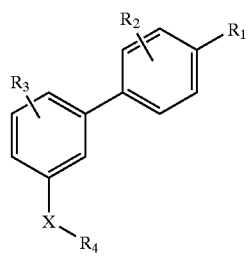

in which $R_1$ is a radical of formula (a) below:

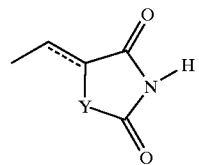

wherein Y is as defined below; $R_2$ and $R_3$, which may be identical or different, are each a hydrogen atom, an alkyl radical having from 1 to 12 carbon atoms, an aryl radical, a halogen atom, a radical —$OR_7$, a polyether radical, a nitro group or an amino group which may optionally be substituted with one or more alkyl radicals having from 1 to 12 carbon atoms, wherein $R_7$ is as defined below; X is the structural linkage below:

$$-(CH_2)_m-(Z)_n-(CO)_p-(W)_q-$$

wherein said structural linkage can be read from left to right or vice versa, and Z, W, m, n, p and q are as defined below; $R_4$ is an alkyl radical having from 1 to 12 carbon atoms, an aryl radical, an aralkyl radical, or a 9-fluorenylmethyl radical; Y is a sulfur atom ; $R_7$ is a hydrogen atom, an alkyl radical having from 1 to 12 carbon atoms or an aralkyl radical; Z is an oxygen or sulfur atom or a radical —N—$R_{12}$, wherein $R_{12}$ is as defined below; W is an oxygen or sulfur atom, a radical —$NR_{13}$ or a =$CH_2$ radical, wherein $R_{13}$ is as defined below; m, n, p and q, which may be identical or different, are each 0 or 1, with the proviso that the sum m+n+p+q is greater than or equal to 2 and that when p is 0 then n or q is equal to 0; $R_{12}$ is a hydrogen atom or an alkyl radical having from 1 to 12 carbon atoms; $R_{13}$ is a hydrogen atom or an alkyl radical having from 1 to 12 carbon atoms; or an optical or geometrical isomer or salt thereof.

2. A compound as defined by claim 1, comprising an alkali metal or alkaline earth metal salt, zinc salt or organoamine salt thereof.

3. A compound as defined by either of claim 1 or 2, wherein and at least one of $R_2$, $R_3$, $R_4$, $R_7$, $R_{12}$, $R_{13}$ is an alkyl radical substituent having from 1 to 12 carbon atoms and selected from the group consisting of methyl, ethyl, isopropyl, butyl, tert-butyl, hexyl, octyl, decyl and dodecyl radicals.

4. A compound as defined by either of claim 1 or 2, wherein at least one of $R_2$ and $R_3$ is polyether radical substituent having from 1 to 6 carbon atoms interrupted with at least one oxygen atom.

5. A compound as defined by either of claim 1 or 2, wherein at least one of $R_2$ and $R_3$ is halogen selected from the group consisting of a fluorine atom, a chlorine atom and a bromine atom.

6. A compound as defined by either of claim 1 or 2, wherein at least one of $R_2$ and $R_3$ is —$OR_7$ wherein $R_7$ is an alkyl radical having from 1 to 6 carbon atoms.

7. A compound as defined by either of claim 1 or 2, wherein at least one of $R_2$, $R_3$, and $R_4$ is an aryl radical substituent, wherein the aryl radical substituent is a phenyl radical which is optionally monosubstituted or disubstituted with a halogen atom, a $CF_3$ radical, an alkyl radical having from 1 to 12 carbon atoms, an alkoxy radical having from 1 to 6 carbon atoms, a nitro group, a polyether radical, a hydroxyl radical optionally protected with an acetyl or benzoyl group or an amino group optionally protected with an acetyl or benzoyl group or optionally substituted with at least one alkyl radical having from 1 to 12 carbon atoms.

8. A compound as defined by either of claim 1 or 2, wherein at least one of $R_4$ and $R_7$ is an aralkyl radical substituent wherein the aralkyl radical substituent is a benzyl or phenethyl radical which is optionally monosubstituted or disubstituted with a halogen atom, a $CF_3$ radical, an alkyl radical having from 1 to 12 carbon atoms, a hydroxyl radical, an alkoxy radical having from 1 to 6 carbon atoms, a nitro group, a polyether radical, a hydroxyl radical optionally protected with an acetyl or benzoyl group or an amino group optionally protected with an acetyl or benzoyl group or optionally substituted with at least one alkyl radical having from 1 to 12 carbon atoms.

9. A compound as defined by claim 1, selected from the group consisting of:
- N-[4'-(2,4-Dioxothiazolidin-5-ylmethyl)biphenyl-3-ylmethyl]-N-methylbenzamide;
- N-[4'-(2,4-Dioxothiazolidin-5-ylmethyl)biphenyl-3-ylmethyl]benzamide;
- 1-[4'-(2,4-Dioxothiazolidin-5-ylmethyl)biphenyl-3-ylmethyl]-3-phenylurea
- 1-[4'-(2,4-Dioxothiazolidin-5-ylmethyl)biphenyl-3-ylmethyl]-1-methyl-3-phenylurea;
- tert-Butyl [4'-(2,4-Dioxothiazolidin-5ylmethyl)-biphenyl-3-ylmethyl]methylcarbamate;
- N-[4'-(2,4-Dioxothiazolidin-5-ylmethyl)biphenyl-3-ylmethyl]-N-methylnonanamide;
- N-[4'-(2,4-Dioxothiazolidin-5-ylmethyl)biphenyl-3-ylmethyl]-N-ethylbenzamide;
- N-[4'-(2,4-Dioxothiazolidin-5-ylmethyl)biphenyl-3-ylmethyl]-N-pentylbenzamide;
- tert-Butyl [4'-(2,4-dioxothiazolidin-5ylmethyl)-biphenyl-3-ylmethyl]ethylcarbamate;
- tert-Butyl [4'-(2,4-dioxothiazolidin-5ylmethyl)-biphenyl-3-ylmethyl]propylcarbamate;
- 9H-Fluoren-9-ylmethyl [4'-(2,4-dioxothiazolidin-5-ylmethyl)biphenyl-3-ylmethyl]methylcarbamate;
- N-[4'-(2,4-Dioxothiazolidin-5-ylmethyl)biphenyl-3-ylmethyl]-2,2,N-trimethylpropionamide;
- N-Octyl-4'-(2,4-dioxothiazolidin-5-ylmethyl)biphenyl-3-carboxamide;
- N-[4'-(2,4-Dioxothiazolidin-5-ylmethyl)biphenyl-3-ylmethyl]-N-methyl-3-phenylpropionamide;
- 2-[4'-(2,4-Dioxothiazolidin-5-ylmethyl)biphenyl-3-yl]-N-methyl-N-phenylacetamide;
- N-[4'-(2,4-Dioxothiazolidin-5-ylidenemethyl)biphenyl-3-ylmethyl]-N-propylbenzamide;
- tert-Butyl [4'-(2,4-Dioxothiazolidin-5-ylmethyl)-biphenyl-3-yl]carbamate;
- N-[4'-(2,4-Dioxothiazolidin-5-ylmethyl)biphenyl-3-ylmethyl]-3,4-diethoxy-N-methylbenzamide;
- N-Benzyl-N-methyl-4'-(2,4-dioxothiazolidin-5-ylmethyl)-biphenyl-3-carboxamide;
- N-Benzyl-4'-(2,4-dioxothiazolidin-5-ylmethyl)biphenyl-3-carboxamide;
- N-[4'-(2,4-Dioxothiazolidin-5-ylmethyl)biphenyl-3-ylmethyl]-N-methyldecanamide;
- N-[4'-(2,4-Dioxothiazolidin-5-ylmethyl)biphenyl-3-yl]-2-phenylacetamide;
- N-[4'-(2,4-Dioxothiazolidin-5-ylmethyl)biphenyl-3-ylmethyl]-N-methyloctanamide;
- N-[4'-(2,4-Dioxothiazolidin-5-ylmethyl)biphenyl-3-ylmethyl]-N-methylheptanamide;
- N-[4'-(2,4-Dioxothiazolidin-5-ylmethyl)biphenyl-3-ylmethyl]-N-methyl-2-phenylacetamide;
- N-[4'-(2,4-Dioxothiazolidin-5-ylmethyl)biphenyl-3-ylmethyl]-4-methoxy-N-methylbenzamide;
- N-[4'-(2,4-Dioxothiazolidin-5-ylmethyl)biphenyl-3-ylmethyl]-3-methoxy-N-methylbenzamide;
- N-[4'-(2,4-Dioxothiazolidin-5-ylmethyl)biphenyl-3-ylmethyl]-3,N-dimethylbenzamide;
- N-[4'-(2,4-Dioxothiazolidin-5-ylmethyl)biphenyl-3-ylmethyl]-N-methyl-4-propylbenzamide;
- N-[4'-(2,4-Dioxothiazolidin-5-ylmethyl)biphenyl-3-ylmethyl]-4,N-dimethylbenzamide;
- N-[4'-(2,4-Dioxothiazolidin-5-ylmethyl)biphenyl-3-ylmethyl]-4-ethoxy-N-methylbenzamide;
- N-[4'-(2,4-Dioxothiazolidin-5-ylmethyl)biphenyl-3-ylmethyl]-4-fluoro-N-methylbenzamide;
- 4-Dimethylamino-N-[4'-(2,4-dioxothiazolidin-5-ylmethyl)biphenyl-3-ylmethyl]-N-methylbenzamide;
- 3,5-Dichloro-N-[4'-(2,4-dioxothiazolidin-5-ylmethyl)-biphenyl-3-ylmethyl]-N-methylbenzamide;
- N-[4'-(2,4-Dioxothiazolidin-5-ylmethyl)biphenyl-3-ylmethyl]-N-methylhexanamide;
- N-[4'-(2,4-Dioxothiazolidin-5-ylmethyl)biphenyl-3-ylmethyl]-2-methoxy-N-methylbenzamide;
- 4-Butoxy-N-[4'-(2,4-dioxothiazolidin-5-ylmethyl)biphenyl-3-ylmethyl]-N-methylbenzamide;
- 4-{[4'-(2,4-Dioxothiazolidin-5-ylmethyl)biphenyl-3-ylmethyl]methylcarbamoyl}phenyl acetate;
- N-[4'-(2,4-Dioxothiazolidin-5-ylmethyl)biphenyl-3-ylmethyl]-4-hydroxy-N-methylbenzamide;
- N-[4'-(2,4-Dioxothiazolidin-5-ylmethyl)biphenyl-3-ylmethyl]-2N-dimethylbenzamide;
- 2-Butyl-N-[4'-(2,4-dioxothiazolidin-5-ylmethyl)-biphenyl-3-ylmethyl]-N-methyloctanamide;
- 4-Acetylamino-N-[4'-(2,4-dioxothiazolidin-5-ylmethyl)-biphenyl-3-ylmethyl]-N-methylbenzamide;
- Hexyl N-[4'-(2,4-dioxothiazolidin-5-ylmethyl)biphenyl-3-ylmethyl]-N-methylcarbamate;
- 1-[4'-(2,4-Dioxothiazolidin-5-ylmethyl)biphenyl-3-yl]-3-phenylurea;
- N-[4'-(2,4-Dioxothiazolidin-5-ylmethyl)biphenyl-3-yl]-N-methyl-2-phenylacetamide;
- 1-[4'-(2,4-Dioxothiazolidin-5-ylmethyl)biphenyl-3-yl]-1-methyl-3-phenylurea;
- 1-[4'-(2,4-Dioxothiazolidin-5-ylmethyl)biphenyl-3-yl]-3-heptyl-1-methylurea;
- 3-[4'-(2,4-Dioxothiazolidin-5-ylidenemethyl)]biphenyl N-phenylcarbamate;
- 3-[4'-(2,4-Dioxothiazolidin-5-ylidenemethyl)]biphenyl N-heptylcarbamate;
- 3-[4'-(2,4-Dioxothiazolidin-5-ylmethyl)]biphenyl phenylacetate;
- 3-[4'-(2,4-Dioxothiazolidin-5-ylmethyl)]biphenyl nonanoate;
- 3-[4'-(2,4-Dioxothiazolidin-5-ylmethyl)]biphenyl N-heptylcarbamate;
- 3-[4'-(2,4-Dioxothiazolidin-5-ylmethyl)]biphenyl N-phenylcarbamate;
- N-[6-Benzyloxy-4'-(2,4-dioxothiazolidin-5-ylidenemethyl)biphenyl-3-ylmethyl]-N-methyloctanamide;
- N-[4'-(2,4-Dioxothiazolidin-5-ylmethyl)-6-hydroxybiphenyl-3-ylmethyl]-N-methyloctanamide;
- N-[4-Benzyloxy-4'-(2,4-dioxothiazolidin-5-ylidenemethyl)biphenyl-3-ylmethyl]-N-methyloctanamide;

N-[4"-(2,4-Dioxothiazolidin-5-ylmethyl)-[1,1';3',1"]terphenyl-5'-ylmethyl]-N-methyloctanamide;

N-[4'-(2,4-Dioxothiazolidin-5-ylmethyl)-2'-methylbiphenyl-3-ylmethyl]-N-methyloctanamide;

N-[4'-(2,4-Dioxothiazolidin-5-ylmethyl)-3'-methylbiphenyl-3-ylmethyl]-N-methyloctanamide;

1-[4'-(2,4-Dioxothiazolidin-5-ylmethyl)biphenyl-3-yl]-1-ethyl-3-phenylurea;

N-[4'-(2,4-Dioxothiazolidin-5-ylmethy)biphenyl-3-yl]-N-methyldecanamide;

N-[4'-(2,4-Dioxothiazolidin-5-ylmethyl)biphenyl-3-yl]-N-methylnonanamide;

N-[4'-(2,4-Dioxothiazolidin-5-ylmethyl)biphenyl-3-yl]-N-methyl-2-(4-butoxyphenyl)acetamide;

N-[4'-(2,4-Dioxothiazolidin-5-ylmethyl)biphenyl-3-yl]-N-methyl-2-(4-methoxyphenyl)acetamide;

N-[4'-(2,4-Dioxothiazolidin-5-ylmethyl)biphenyl-3-yl]-N-methyl-2-(4-ethoxyphenyl)acetamide;

N-[4'-(2,4-Dioxothiazolidin-5-ylmethyl)biphenyl-3-yl]-N-methyl-2-(4-hydroxyphenyl)acetamide;

1-[4'-(2,4-Dioxothiazolidin-5-ylmethyl)biphenyl-3-yl]-1-methyl-3-(4-butoxyphenyl)urea;

1-[4'-(2,4-Dioxothiazolidin-5-ylmethyl)biphenyl-3-yl]-1-methyl-3-(4-methoxyphenyl)urea;

1-[4'-(2,4-Dioxothiazolidin-5-ylmethyl)biphenyl-3-yl]-1-methyl-3-(4-ethoxyphenyl)urea;

1-[4'-(2,4-Dioxothiazolidin-5-ylmethyl)biphenyl-3-yl]-1-methyl-3-(4-hydroxy phenyl)urea;

5-{3'-[Methyl-(2-oxo-2-phenyl ethyl)amino]biphenyl-4-ylmethyl}thiazolidine-2,4-dione;

5-[3'-(Methylphenethylamino)biphenyl-4-ylmethyl]-thiazolidine-2,4-dione;

Phenyl [4'-(2,4-dioxothiazolidin-5-ylmethyl)biphenyl-3-yl]methylcarbamate; and tert-Butyl [4'-(2,4-dioxothiazolidin-5-ylmethyl)-biphenyl-3-yl]methylcarbamate or mixture thereof.

10. A compound as defined by claim 1, wherein formula (I), $R_1$ is the radical of formula (a) and X is a structural linkage —$CH_2$—N($R_{12}$)—CO—, —$NR_{12}$—(CO)—$NR_{13}$ or $NR_{12}$—(CO)—$CH_2$—, these linkages being read from left to right or vice versa.

11. A pharmaceutical composition, comprising at least one compound as defined by claim 1, formulated into a pharmaceutically acceptable support therefor.

12. The pharmaceutical composition as defined by claim 11, comprising from 0.001% to 10% by weight of said at least one compound.

13. The pharmaceutical composition as defined by claim 11, comprising from 0.01% to 1% by weight of said at least one compound.

14. A compound as defined by claim 6, wherein at least one of $R_2$ and $R_3$ is —$OR_7$, wherein —$OR_7$ is selected from the group consisting of methoxy, ethoxy, isopropyloxy, tert-butoxy and hexyloxy radicals.

* * * * *